US012806218B2

(12) United States Patent
Schneider

(10) Patent No.: US 12,806,218 B2

(45) Date of Patent: Nov. 24, 2026

(54) METHODS FOR TREATING NEURODEGENERATIVE DISORDERS

(71) Applicant: THOMAS JEFFERSON UNIVERSITY, Philadelphia, PA (US)

(72) Inventor: Jay S. Schneider, Cherry Hill, NJ (US)

(73) Assignee: Thomas Jefferson University, Philadelphia, PA (US)

( * ) Notice: Subject to any disclaimer, the term of this patent is extended or adjusted under 35 U.S.C. 154(b) by 1063 days.

(21) Appl. No.: 17/607,294

(22) PCT Filed: Apr. 29, 2020

(86) PCT No.: PCT/US2020/030409

§ 371 (c)(1),
(2) Date: Oct. 28, 2021

(87) PCT Pub. No.: WO2020/223310

PCT Pub. Date: Nov. 5, 2020

(65) Prior Publication Data

US 2022/0226357 A1 Jul. 21, 2022

Related U.S. Application Data

(60) Provisional application No. 62/840,235, filed on Apr. 29, 2019.

(51) Int. Cl.

*A61P 25/28* (2006.01)
*A61K 31/7032* (2006.01)
(Continued)

(52) U.S. Cl.

CPC .......... *A61K 31/7032* (2013.01); *A61K 38/45* (2013.01); *A61K 38/47* (2013.01);
(Continued)

(58) Field of Classification Search

CPC .. A61P 25/28; C12N 15/86; C12Y 302/01018
See application file for complete search history.

(56) References Cited

U.S. PATENT DOCUMENTS 10,874,749 B2 * 12/2020 Schneider .......... A61K 48/0075
2014/0187507 A1 7/2014 Defrees et al.
(Continued)

FOREIGN PATENT DOCUMENTS

JP 2013508366 A 3/2013
JP 2014523881 A 9/2014
(Continued)

OTHER PUBLICATIONS

Breiden, Bernadette, and Konrad Sandhoff. "Lysosomal Glycosphingolipid Storage Diseases." Annual Review of Biochemistry, vol. 88, No. 1, Jun. 20, 2019, pp. 461-485, https://doi.org/10.1146/annurev-biochem-013118-111518. (Year: 2019).*
(Continued)

*Primary Examiner* — Kimberly Chong
*Assistant Examiner* — Africa M Mcleod
(74) *Attorney, Agent, or Firm* — Saul Ewing LLP; Justin Crotty; Kathryn Doyle

(57) ABSTRACT

The present invention relates to methods of treating Lewy body dementia, multi-system atrophy or pure autonomic failure in a subject in need thereof. Also provided are compositions for treating Lewy body dementia, multi-system atrophy or pure autonomic failure.

1 Claim, 18 Drawing Sheets

Specification includes a Sequence Listing.

(51) Int. Cl.
*A61K 38/45* (2006.01)
*A61K 38/47* (2006.01)
*A61P 25/16* (2006.01)
*C12N 15/86* (2006.01)

(52) U.S. Cl.
CPC ............... *A61P 25/16* (2018.01); *A61P 25/28* (2018.01); *C12N 15/86* (2013.01); *C12Y 204/01062* (2013.01); *C12Y 302/01018* (2013.01); *C12N 2750/14143* (2013.01); *C12N 2750/14171* (2013.01)

(56) References Cited

U.S. PATENT DOCUMENTS

| | | | | |
|---|---|---|---|---|
| 2016/0082026 | A1 | 3/2016 | Schneider et al. | |
| 2018/0214573 | A1* | 8/2018 | Anderson | A61P 25/28 |
| 2021/0213142 | A1* | 7/2021 | Schneider | A61K 35/30 |

FOREIGN PATENT DOCUMENTS

| | | | |
|---|---|---|---|
| JP | 2017514515 | A | 6/2017 |
| WO | 2007018275 | A1 | 2/2007 |
| WO | 2009104649 | A1 | 8/2009 |
| WO | 2011049736 | A1 | 4/2011 |
| WO | 2012177997 | A1 | 12/2012 |
| WO | 2015155694 | A1 | 10/2015 |
| WO | 2017009312 | A1 | 1/2017 |
| WO | 2017015491 | A1 | 1/2017 |

OTHER PUBLICATIONS

Keiser, Megan S., et al. "Techniques for Intracranial Stereotaxic Injections of Adeno-Associated Viral Vectors in Adult Mice." Current Protocols in Mouse Biology, vol. 8, No. 4, Nov. 5, 2018, p. e57, https://doi.org/10.1002/cpmo.57. (Year: 2018).*

Martinez, Zak, et al. "GM1 Specifically Interacts with α-Synuclein and Inhibits Fibrillation." Biochemistry, vol. 46, No. 7, Jan. 25, 2007, pp. 1868-1877, https://doi.org/10.1021/bi061749a. Accessed Sep. 26, 2021. (Year: 2007).*

McGonigle, Paul, and Bruce Ruggeri. "Animal Models of Human Disease: Challenges in Enabling Translation." Biochemical Pharmacology, vol. 87, No. 1, Jan. 1, 2014, pp. 162-171, www.sciencedirect.com/science/article/pii/S0006295213004929, https://doi.org/10.1016/j.bcp.2013.08.006. (Year: 2014).*

Nuytemans, Karen, et al. "Genetic Etiology of Parkinson Disease Associated with Mutations in the SNCA, PARK2, PINK1, PARK7, and LRRK2 Genes: A Mutation Update." Human Mutation, vol. 31, No. 7, May 18, 2010, pp. 763-780, www.ncbi.nlm.nih.gov/pmc/articles/PMC3056147/, https://doi.org/10.1002/humu.21277. (Year: 2010).*

Schneider, Jay S., et al. "A Randomized, Controlled, Delayed Start Trial of GM1 Ganglioside in Treated Parkinson's Disease Patients." Journal of the Neurological Sciences, vol. 324, No. 1-2, Jan. 2013, pp. 140-148, https://doi.org/10.1016/j.jns.2012.10.024. Accessed Jan. 14, 2020. (Year: 2013).*

McGonigle P. Animal models of CNS disorders. Biochem Pharmacol. Jan. 1, 2014;87(1):140-9. doi: 10.1016/j.bcp.2013.06.016. Epub Jun. 26, 2013. PMID: 23811310. (Year: 2014).*

Zhou, Kai, et al. "Routes of Administration for Adeno-Associated Viruses Carrying Gene Therapies for Brain Diseases." Frontiers in Molecular Neuroscience, vol. 15, Oct. 26, 2022, https://doi.org/10.3389/fnmol.2022.988914. (Year: 2022).*

"Supplementary European Search Report dated Apr. 19, 2023 for European Patent Appln. No. 20 79 8336.2".

Verma , et al., "siRNA-mediated knockdown of B3GALT4 decreases GMI ganglioside expression and enhances vulnerability for neurodegeneration", Molecular and Cellular Neurosciences, vol. 95, Jan. 3, 2019, 25-30.

"Partial Supplementary Search Report dated Dec. 16, 2022 for EP Appln. No. EP 20 79 8336".

Ledeen , et al., "The multi-tasked life of GMI ganglioside, a true factotum of nature", Trends in Biochemical Sciences, Elsevier, Amsterdam, NL, vol. 40, No. 7, Jul. 1, 2015, 407-418.

Schneider , et al., "GMI ganglioside in Parkinson's disease: Results of a five year open study", Journal of Neurological Sciences., vol. 292, No. 1-2, Mar. 5, 2010, 45-51.

Takada, Mashiko, "Development of primate models for Parkinson's disease due to overexpression of α-synuclein", Japanese Journal of Biological Psychiatry, 2013, 24, 57-61, DOI: 10.11249/jsbpjjpp.24.1_57.

"International Search Report and Written Opinion dated Oct. 30, 2020 for International Application No. PCT/US20/30409".

Anderson, et al., "Phosphorylation of Ser-129 is the dominant pathological modification of alpha-synuclein in familial and sporadic Lewy body disease.", J Biol Chem 281, https://doi.org/10.1074/jbc.M600933200, 2006, 29739-29752.

Arawaka, et al., ". Mechanisms underlying extensive Ser129-phosphorylation in alpha-synuclein aggregates.", Acta Neuropathol Commun 5, 48, https://doi.org/10.1186/s40478-017-0452-6, 2017.

Baba, et al., "Aggregation of alpha-Synuclein in Lewy Bodies of Sporadic Parkinson's Disease and Dementia with Lewy Bodies", Am J Pathol, vol. 152, No. 4, 1998, pp. 879-884.

Bartels, et al., "N-alpha-acetylation of alpha-synuclein increases its helical folding propensity, GM1 binding specificity and resistance to aggregation", PLoS One, vol. 9, No. 7,, Jul. 30, 2014, e103727 1-10.

Cuervo, et al., "Impaired degradation of mutant alpha-synuclein by chaperone-mediated autophagy.", Science 305, https://doi.org/10.1126/science.1101738, 2004, 1292-1295.

Dai, et al., "Enhanced Autophagy Contributes to Protective Effects of GM1 Ganglioside Against Abeta1-42-Induced Neurotoxicity and Cognitive Deficits.", Neurochem Res 42, https://doi.org/10.1007/s11064-017-2266-0, 2017, 2417-2426.

Decressac, et al., "GDNF fails to exert neuroprotection in a rat alpha-synuclein model of Parkinson's disease.", Brain 134, https://doi.org/10.1093/brain/awr149, 2011, 2302-2311.

Decressac, et al., "TFEB-mediated autophagy rescues midbrain dopamine neurons from alpha-synuclein toxicity.", roc Natl Acad Sci USA 110, https://doi.org/10.1073/pnas.1305623110, 2013, E1817-1826.

Fujiwara, et al., "alpha-Synuclein is phosphorylated in synucleinopathy lesions.", Nat Cell Biol 4, https://doi.org/10.1038/ncb748, 2002, 160-164.

Goldberg, et al., "Is there a cause-and-effect relationship between a-synuclein fibrillization and Parkinson's disease?", Nature Cell Biology 2, 2000, 115-119.

Hadaczek, et al., "GDNF signaling implemented by GM1 ganglioside; failure in Parkinson's disease and GM1-deficient murine model.", Experimental neurology 263, https://doi.org/10.1016/j.expneurol.2014.10.010, 2015, 177-189.

Hadjiconstantinou, et al., "Administration of GM1 ganglioside restores the dopamine content in striatum after chronic treatment with MPTP.", Neuropharmacology 25, 1986, 1075-1077.

Hakomori, et al., "Gangliosides and glycosphingolipids as modulators of cell growth, adhesion, and transmembrane signaling", Adv Lipid Res 25, 1993, 147-162.

Hatano, et al., "Leucine-rich repeat kinase 2 associates with lipid rafts.", Hum Mol Genet 16, https://doi.org/10.1093/hmg/ddm013, 2007, 678-690.

Herrero GM-1, et al., "Mt ganglisoide promotes the recovery of surviving midbrain dopaminergic neurons in MPTP-treated monkeys.", Neuroscience 56, 1993, 965-972.

Ip, et al., "AAV1/2-induced overexpression of A53T-alpha-synuclein in the substantia nigra results in degeneration of the nigrostriatal system with Lewy-like pathology and motor impairment: a new mouse model for Parkinson's disease.", Acta Neuropathol Commun 5, 11, https://doi.org/10.1186/s40478-017-0416-x, 2017.

Jonsson, et al., "ffects of GM1 ganglioside on developing and mature serotonin and noradrenaline neurons lesioned by selective neurotoxins.", Journal of Neuroscience Research 12, https://doi.org/10.1002/jnr.490120229, 1984, 459-475.

(56) References Cited

OTHER PUBLICATIONS

Kirik, et al., “Nigrostriatal alpha-synucleinopathy induced by viral vector-mediated overexpression of human alpha-synuclein: a new primate model of Parkinson’s disease.”, Proc Natl Acad Sci USA 100, https://doi.org/10.1073/pnas.0536383100, 2003, 2884-2889.
Koprich, et al., “Expression of human A53T alpha-synuclein in the rat substantia nigra using a novel AAV1/2 vector produces a rapidly evolving pathology with protein aggregation, dystrophic neurite architecture and nigrostriatal degeneration with potential to model the”, pathology of Parkinson’s disease. Mol Neurodegener 5, 43, https://doi.org/10.1186/1750-1326-5-43, 2010.
Koprich, et al., “Progressive neurodegeneration or endogenous compensation in an animal model of Parkinson’s disease produced by decreasing doses of alpha-synuclein.”, PLoS One 6, e17698, https://doi.org/10.1371/journal.bone.0017698, 2011.
Lang, et al., “Disease Modification in Parkinson’s Disease: Current Approaches, Challenges, and Future Considerations.”, Mov Disord 33, https://doi.org/10.1002/mds.27360, 2018, 660-677.
Ledeen, et al., “Ganglioside function in calcium homeostasis and signaling.”, Neurochem Res 27, 2002, 637-647.
Li, et al., “Effect of familial Parkinson’s disease point mutations A30P and A53T on the structural properties, aggregation, and fibrillation of human alpha-synuclein.”, Biochemistry 40, 2001, 11604-11613.
Martinez, et al., “GM1 specifically interacts with alpha-synuclein and inhibits fibrillation.”, Biochemistry 46, https://doi.org/10.1021/bi061749a, 2007, 1868-1877.
Narhi, et al., “Both Familial Parkinson’s Disease Mutations Accelerate alpha-synuclein Aggregation”, J Biol Chem, vol. 274, No. 14, 1999, pp. 9843-9846.
Oderfeld-Nowak, et al., “Effect of GM1 ganglioside treatment on postlesion responses of cholinergic enzymes in rat hippocampus after various partial deafferentations.”, Journal of Neuroscience Research 12, https://doi.org/10.1002/inr.490120225, 1984, 409-420.
Pope-Coleman, et al., Neuroscience 56, Synapse 36, 120-128, doi: 10.1002/(SICI)1098-2396(200005)36:2<120 ::AID-SYN5>3.0.CO;2-Y (2000)., 1993, 965-972.
Pope-Coleman, et al., “Effects of Chronic GM1 Ganglioside Treatment on Cognitieve and Motor Deficits in a Slowly Progressing Model of Parkinsonism in Non-Human Primates.”, Restor Neurol Neurosci 12, 1998, 255-266.
Proia, R. L., “Gangliosides help stabilize the brain.”, Nat Genet 36, https://doi.org/10.1038/ng1104-1147, 2004, 1147-1148.
Pupyshev, et al., “Suppression of autophagy in the brain of transgenic mice with overexpression of capital A, Cyrillic53capital TE, Cyrillic-mutant alpha-synuclein as an early event at synucleinopathy progression.”, eurosci Lett 672, https://doi.org/10.1016/j.neulet.2017.12.001, 2018, 140-144.
Schengrund, C. L., “Gangliosides: glycosphingolipids essential for normal neural development and function.”, Trends Biochem Sci 40, https://doi.org/10.1016/j.tibs.2015.03.007, 2015, 397-406.
Schengrund, C. L., “Lipid rafts: keys to neurodegeneration”, Brain Res Bull 82, https://doi.org/10.1016/j.brainresbull.2010.02.013, 2010, 7-17.
Schengrund, C. L., “The role(s) of gangliosides in neural differentiation and repair: a perspective.”, Brain Res Bull 24, 1990, 131-141.
Schneider, et al., “A randomized, controlled, delayed start trial of GM1 ganglioside in treated Parkinson’s disease patients.”, J Neurol Sci 324, https://doi.org/10.1016/j.jns.2012.10.024, 2013, 140-148.
Schneider, J. S., “Altered expression of genes involved in ganglioside biosynthesis in substantia nigra neurons in Parkinson’s disease.”, PLoS One 13, e0199189, https://doi.org/10.1371/journal.pone.0199189, 2018.
Schneider, et al., “GM1 ganglioside in Parkinson’s disease: Pilot study of effects on dopamine transporter binding.”, J Neurol Sci 356, https://doi.org/10.1016/j.jns.2015.06.028, 2015, 118-123.
Schneider, et al., “GM1 ganglioside rescues substantia nigra pars compacta neurons and increases dopamine synthesis in residual nigrostriatal dopaminergic neurons in MPTP-treated mice.”, Journal of Neuroscience Research 42, 1995, 117-123.
Schneider, et al., “GM1 ganglioside treatment promotes recovery of striatal dopamine concentrations in the mouse model of MPTP-induced Parkinsonism.”, Experimental Neurology 105, 1989, 177-183.
Schneider, et al., “Parkinson’s disease: Improved function with GM1 ganglioside treatment in a randomized placebo-controlled study.”, Neurology 50, 1998, 1630-1636.
Schneider, et al., “Recovery from Experimental Parkinsonism in Primates with GM1 Ganglioside Treatment.”, Science 256, 1992, 843-846.
Seyfried, et al., “Sex-Related Abnormalities in Substantia Nigra Lipids in Parkinson’s Disease.”, ASN Neuro 10, 1759091418781889, https://doi.org/10.1177/1759091418781889, 2018.
Spillantini, et al., “Alpha-synuclein in Lewy Bodies”, Nature, vol. 388, No. 6645, 1987, pp. 839-840.
Stults, et al., “Glycosphingolipids: structure, biological source, and properties”, Methods Enzymol 179, 1989, 167-214.
Wei, et al., “Protective role of endogenous gangliosides for lysosomal pathology in a cellular model of synucleinopathies.”, Am J Pathol 174, https://doi.org/10.2353/ajpath.2009.080680, 2009, 1891-1909.
Wu, et al., “Deficiency of ganglioside GM1 correlates with Parkinson’s disease in mice and humans.”, Journal of Neuroscience Research 90, https://doi.org/10.1002/jnr.23090, 2012, 1997-2008.
Yacoubian, et al., “Targets for neuroprotection in Parkinson’s disease.”, Biochim Biophys Acta 1792, https://doi.org/10.1016/j.bbadis.2008.09.009, 2009, 676-687.
Schneider , et al., “GM1 Ganglioside Modifies α-Synuclein Toxicity and is Neuroprotective in a Rat α-Synuclein Model of Parkinson’s Disease”, Scientific Reports, 2019, 9, 8362, 1-12, DOI:10.1038/s41598-019-42847-x.
Wei , et al., “Gangliosides protection against lysosomal pathology of synucleinopathies,”, Autophagy, 2009, 5, 860-861, DOI:doi.org/10.4161/auto.8825.

* cited by examiner

SEQUENCE LISTING

<160> NUMBER OF SEQ ID NOS: 2

<210> SEQ ID NO 1
<211> LENGTH: 6779
<212> TYPE: DNA
<213> ORGANISM: Artificial Sequence
<220> FEATURE:
<223> OTHER INFORMATION: AAV-Syn-hB3GATL4-SynEGFP

<400> SEQUENCE: 1

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggccaat tcagtcgata actataacgg tcctaaggta    180

gcgatttaaa tacgcgctct cttaaggtag ccccgggacg cgtcaattcg cgcctgagtt    240

gaatatcaac actacaaacc gagtatctgc agagggccct gcgtatgagt gcaagtgggt    300

tttaggacca ggatgaggcg ggtgggggt  gcctacctga cgaccgaccc cgacccactg    360

gacaagcacc caacccccat tccccaaatt gcgcatcccc tatcagagag ggggagggga    420

aacaggatgc ggcgaggcgc gtgcgcactg ccagcttcag caccgcggac agtgccttcg    480

cccccgcctg gcggcgcgcg ccaccgccgc ctcagcactg aaggcgcgct gacgtcactc    540

gccggtcccc cgcaaactcc ccttcccggc caccttggtc gcgtccgcgc cgccgccggc    600

ccagccggac cgcaccacgc gaggcgcgag atagggggc  acgggcgcga ccatctgcgc    660

tgcggcgccg gcgactcagc gctgcctcag tctgcggtgg gcagcggagg agtcgtgtcg    720

tgcctgagag cgcagctgtg ctcctgggca ccgcgcagtc cgcccccgcg gctcctggcc    780

agaccacccc taggaccccc tgccccaagt cgcagccttc gaattcccac catgcagctc    840

aggctcttcc ggcgcctcct tctcgccgct ttgctgctgg tgatcgtctg gaccctcttc    900

gggccttcgg ggttgggggga ggagctgctg agcctctcac tagcctccct gctcccagcc    960

cccgcctcac cggggccgcc cctggccctg ccccgcctct tgatccccaa ccaggaagct   1020

tgcagtggtc ccggggcccc tcccttcctg ctcatcctgg tgtgcacggc tccggagaac   1080

ctgaaccaga gaaacgccat tcgggcttcg tggggcgggc tgcgcgaggc ccgggggctc   1140

agggtacaga cgctattctt gctgggagag ccgaacgcac agcaccccgt gtggggttcc   1200

caggggagtg acctggcctc ggagtcagca gcccaggggg atatcttgca ggccgccttc   1260

caggactcct accgcaacct caccctaaag accctcagcg ggctgaactg ggctgagaaa   1320

cactgcccca tggcccgata cgtcctcaag acggacgatg atgtgtatgt caacgtccct   1380

gaactggtat cagagctggt cttgcgaggg ggccgttggg ggcaatggga gagaagcacg   1440

gaaccccaga gagaggctga gcaggaagga ggccaggttt tgcacagcga ggaagtgcct   1500

cttctgtact tgggccgggt gcactggcgc gtgaacccct ctcggacacc ggggggcagg   1560

caccgcgtat cagaggagca gtggcctcac acctggggcc cctttccacc ctatgcctca   1620

ggcacggggt atgtgctgtc agcgtctgct gtgcagctca ttctcaaggt ggccagccgg   1680

gcaccccttc tcccattaga ggatgtcttt gtgggggtaa gtgcccgacg aggaggcctc   1740

gccccaacac agtgtgtcaa gctggctggt gccacccact acccgctaga ccggtgctgc   1800
```

```
tatgggaaat tcctgctgac gtcccacagg ctggacccct ggaagatgca ggaagcctgg   1860
aagctggtgg gtggctctga cggggaaagg actgcgccct tttgctcctg gttccaggga   1920
gtcctgggca tcctgcggtg tcgagcaata gcctggcttc agagctgagg atccaccgga   1980
tctagataac tgatcataat cagccatacc acatttgtag aggttttact tgctttaaaa   2040
aacctcccac acctccccct gaacctgaaa cataaaatga atgcaattgt tgttgttaac   2100
ttgtttattg cagcttataa tggttacaaa taaagcaata gcatcacaaa tttcacaaat   2160
aaagcatttt tttcactgca ttctagttgt ggtttgtcca aactcatcaa tgtatcttaa   2220
cgcccttccc aacagttgcg cagcctgaat ggcgaatgga cgcgccctgt agcggactag   2280
tagtatctgc agagggccct gcgtatgagt gcaagtgggt tttaggacca ggatgaggcg   2340
gggtgggggt gcctacctga cgaccgaccc cgacccactg gacaagcacc caacccccat   2400
tccccaaatt gcgcatcccc tatcagagag ggggagggga aacaggatgc ggcgaggcgc   2460
gtgcgcactg ccagcttcag caccgcggac agtgccttcg cccccgcctg gcggcgcgcg   2520
ccaccgccgc ctcagcactg aaggcgcgct gacgtcactc gccggtcccc cgcaaactcc   2580
ccttcccggc caccttggtc gcgtccgcgc cgccgccggc ccagccggac cgcaccacgc   2640
gaggcgcgag atagggggc acgggcgcga ccatctgcgc tgcggcgccg gcgactcagc   2700
gctgcctcag tctgcggtgg gcagcggagg agtcgtgtcg tgcctgagag cgcagctgtg   2760
ctcctgggca ccgcgcagtc cgcccccgcg gctcctggcc agaccacccc taggaccccc   2820
tgccccaagt cgcagccaag cttagaattg gagcttgctt ctatagatcc accggtcgcc   2880
accatggtga gcaagggcga ggagctgttc accggggtgg tgcccatcct ggtcgagctg   2940
gacggcgacg taaacggcca caagttcagc gtgtccggcg agggcgaggg cgatgccacc   3000
tacggcaagc tgaccctgaa gttcatctgc accaccggca agctgcccgt gccctggccc   3060
accctcgtga ccaccctgac ctacggcgtg cagtgcttca gccgctaccc cgaccacatg   3120
aagcagcacg acttcttcaa gtccgccatg cccgaaggct acgtccagga gcgcaccatc   3180
ttcttcaagg acgacggcaa ctacaagacc cgcgccgagg tgaagttcga gggcgacacc   3240
ctggtgaacc gcatcgagct gaagggcatc gacttcaagg aggacggcaa catcctgggg   3300
cacaagctgg agtacaacta caacagccac aacgtctata tcatggccga caagcagaag   3360
aacggcatca aggtgaactt caagatccgc cacaacatcg aggacggcag cgtgcagctc   3420
gccgaccact accagcagaa cacccccatc ggcgacggcc ccgtgctgct gcccgacaac   3480
cactacctga gcacccagtc cgccctgagc aaagacccca acgagaagcg cgatcacatg   3540
gtcctgctgg agttcgtgac cgccgccggg atcactctcg gcatggacga gctgtacaag   3600
taaagcggcc gctcgagtct agagggccct tcgaaggtaa gcctatccct aaccctctcc   3660
tcggtctcga ttctacgcgt accggtcatc atcaccatca ccattgagtt taaacccgct   3720
gatcagcctc gactgtgcct tctagttgcc agccatctgt tgtttgcccc tcccccgtgc   3780
cttccttgac cctggaaggt gccactccca ctgtcctttc ctaataaaat gaggaaattg   3840
catcgcattg tctgagtagg tgtcattcta ttctgggggg tggggtgggg caggacagca   3900
agggggagga ttgggaagac aatagcaggc atgctgggga tgcggtgggc tctatggctt   3960
ctgaggcgga aagaaccaga tcctctctta aggtagcatc gagatttaaa ttagggataa   4020
cagggtaatg gcgcgggccg caggaacccc tagtgatgga gttggccact ccctctctgc   4080
gcgctcgctc gctcactgag gccgggcgac caaaggtcgc ccgacgcccg ggctttgccc   4140
```

```
gggcggcctc agtgagcgag cgagcgcgca gctgcctgca ggggcgcctg atgcggtatt   4200
ttctccttac gcatctgtgc ggtatttcac accgcatacg tcaaagcaac catagtacgc   4260
gccctgtagc ggcgcattaa gcgcggcggg tgtggtggtt acgcgcagcg tgaccgctac   4320
acttgccagc gccctagcgc ccgctccttt cgctttcttc ccttcctttc tcgccacgtt   4380
cgccggcttt ccccgtcaag ctctaaatcg ggggctccct ttagggttcc gatttagtgc   4440
tttacggcac ctcgacccca aaaaacttga tttgggtgat ggttcacgta gtgggccatc   4500
gccctgatag acggtttttc gccctttgac gttggagtcc acgttcttta atagtggact   4560
cttgttccaa actggaacaa cactcaaccc tatctcgggc tattcttttg atttataagg   4620
gattttgccg atttcggcct attggttaaa aaatgagctg atttaacaaa aatttaacgc   4680
gaattttaac aaaatattaa cgtttacaat tttatggtgc actctcagta caatctgctc   4740
tgatgccgca tagttaagcc agccccgaca cccgccaaca cccgctgacg cgccctgacg   4800
ggcttgtctg ctcccggcat ccgcttacag acaagctgtg accgtctccg ggagctgcat   4860
gtgtcagagg ttttcaccgt catcaccgaa acgcgcgaga cgaaagggcc tcgtgatacg   4920
cctattttta taggttaatg tcatgataat aatggtttct tagacgtcag gtggcacttt   4980
tcggggaaat gtgcgcggaa cccctatttg tttatttttc taaatacatt caaatatgta   5040
tccgctcatg agacaataac cctgataaat gcttcaataa tattgaaaaa ggaagagtat   5100
gagtattcaa catttccgtg tcgcccttat tccctttttt gcggcatttt gccttcctgt   5160
ttttgctcac ccagaaacgc tggtgaaagt aaaagatgct gaagatcagt tgggtgcacg   5220
agtgggttac atcgaactgg atctcaacag cggtaagatc cttgagagtt ttcgccccga   5280
agaacgtttt ccaatgatga gcacttttaa agttctgcta tgtggcgcgg tattatcccg   5340
tattgacgcc gggcaagagc aactcggtcg ccgcatacac tattctcaga atgacttggt   5400
tgagtactca ccagtcacag aaaagcatct tacggatggc atgacagtaa gagaattatg   5460
cagtgctgcc ataaccatga gtgataacac tgcggccaac ttacttctga caacgatcgg   5520
aggaccgaag gagctaaccg cttttttgca caacatgggg gatcatgtaa ctcgccttga   5580
tcgttgggaa ccggagctga atgaagccat accaaacgac gagcgtgaca ccacgatgcc   5640
tgtagcaatg gcaacaacgt tgcgcaaact attaactggc gaactactta ctctagcttc   5700
ccggcaacaa ttaatagact ggatggaggc ggataaagtt gcaggaccac ttctgcgctc   5760
ggcccttccg gctggctggt ttattgctga taaatctgga gccggtgagc gtgggtctcg   5820
cggtatcatt gcagcactgg ggccagatgg taagccctcc cgtatcgtag ttatctacac   5880
gacggggagt caggcaacta tggatgaacg aaatagacag atcgctgaga taggtgcctc   5940
actgattaag cattggtaac tgtcagacca agtttactca tatatacttt agattgattt   6000
aaaacttcat ttttaattta aaaggatcta ggtgaagatc ctttttgata atctcatgac   6060
caaaatccct taacgtgagt tttcgttcca ctgagcgtca gaccccgtag aaaagatcaa   6120
aggatcttct tgagatcctt tttttctgcg cgtaatctgc tgcttgcaaa caaaaaaacc   6180
accgctacca gcggtggttt gtttgccgga tcaagagcta ccaactcttt ttccgaaggt   6240
aactggcttc agcagagcgc agataccaaa tactgtcctt ctagtgtagc cgtagttagg   6300
ccaccacttc aagaactctg tagcaccgcc tacatacctc gctctgctaa tcctgttacc   6360
agtggctgct gccagtggcg ataagtcgtg tcttaccggg ttggactcaa gacgatagtt   6420
accggataag gcgcagcggt cgggctgaac ggggggttcg tgcacacagc ccagcttgga   6480
gcgaacgacc tacaccgaac tgagatacct acagcgtgag ctatgagaaa gcgccacgct   6540
```

tcccgaaggg agaaaggcgg acaggtatcc ggtaagcggc agggtcggaa caggagagcg 6600
cacgagggag cttccagggg gaaacgcctg gtatctttat agtcctgtcg ggtttcgcca 6660
cctctgactt gagcgtcgat ttttgtgatg ctcgtcaggg gggcggagcc tatggaaaaa 6720
cgccagcaac gcggcctttt tacggttcct ggccttttgc tggccttttg ctcacatgt 6779

<210> SEQ ID NO 2
<211> LENGTH: 8046
<212> TYPE: DNA
<213> ORGANISM: Artificial Sequence
<220> FEATURE:
<223> OTHER INFORMATION: AAV-Syn-hNEU3-SynEGFP

<400> SEQUENCE: 2
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccaat tcagtcgata actataacgg tcctaaggta 180
gcgatttaaa tacgcgctct cttaaggtag ccccgggacg cgtcaattcg cgcctgagtt 240
gaatatcaac actacaaacc gagtatctgc agagggccct gcgtatgagt gcaagtgggt 300
tttaggacca ggatgaggcg ggtgggggt gcctacctga cgaccgaccc cgacccactg 360
gacaagcacc caaccccat tccccaaatt gcgcatcccc tatcagagag ggggagggga 420
aacaggatgc ggcgaggcgc gtgcgcactg ccagcttcag caccgcggac agtgccttcg 480
cccccgcctg gcggcgcgcg ccaccgccgc ctcagcactg aaggcgcgct gacgtcactc 540
gccggtcccc cgcaaactcc ccttcccggc caccttggtc gcgtccgcgc cgccgccggc 600
ccagccggac cgcaccacgc gaggcgcgag atagggggc acgggcgcga ccatctgcgc 660
tgcggcgccg gcgactcagc gctgcctcag tctgcggtgg gcagcggagg agtcgtgtcg 720
tgcctgagag cgcagctgtg ctcctgggca ccgcgcagtc cgcccccgcg gctcctggcc 780
agaccacccc taggaccccc tgccccaagt cgcagccttc gaattcgccc ttcccacgta 840
ggccttccaa agcgctgaga ttgtaggcat aagccaccag gcccagccta ttacctttac 900
gttgtactta gtcccagata aaaaatgacc ttagatcagt cctttcctct ttggctgggg 960 agagggggc ttaaattccg gtactgtgaa acagaagaat ggactcagtg ctatgtgaca 1020
aatctatgta tgtaaatgtg tgtatataca cacacataaa ttatatatat gaatatattt 1080
tcattttcat attttgcaag gagagtagcc aatgctctgg acctctggtc ctttttgtag 1140
ggtaccctct gaggccggga acctttgctc aactctcagg ctgtccaggg aagctttagg 1200
cggtgatacc gagctacaga ccaatataag agctcggggc tgtggcactg aagagaggag 1260
gcggccgttg ggaactgagt ctccccagcc ttggggccgg tgcctcttcc gggcttcggc 1320
gaatgagacc tgcggacctg cccccgcgcc ccatggaaga atccccggcg tccagctctg 1380
ccccgacaga gacggaggag ccggggtcca gtgcagaggt catggaagaa gtgacaacat 1440
gctccttcaa cagccctctg ttccggcagg aagatgacag agggattacc taccggatcc 1500
cagccctgct ctacataccc cccacccaca ccttcctggc ctttgcagag aagcgttcta 1560
cgaggagaga tgaggatgct ctccacctgg tgctgaggcg agggttgagg attgggcagt 1620
tggtacagtg gggccccctg aagccactga tggaagccac actaccgggg catcggacca 1680
tgaacccctg tcctgtatgg gagcagaaga gtggttgtgt gttcctgttc ttcatctgtg 1740
tgcggggcca tgtcacagag cgtcaacaga ttgtgtcagg caggaatgct gcccgccttt 1800

-continued gcttcatcta cagtcaggat gctggatgtt catggagtga ggtgagggac ttgactgagg 1860
aggtcattgg ctcagagctg aagcactggg ccacatttgc tgtgggccca ggtcatggca 1920
tccagctgca gtcagggaga ctggtcatcc ctgcgtatac ctactacatc ccttcctggt 1980
tcttttgctt ccagctacca tgtaaaacca ggcctcattc tctgatgatc tacagtgatg 2040
acctaggggt cacatggcac catggtagac tcattaggcc catggttaca gtagaatgtg 2100
aagtggcaga ggtgactggg agggctggcc accctgtgct atattgcagt gcccggacac 2160
caaacaggtg ccgggcagag gcgctcagca ctgaccatgg tgaaggcttt cagagactgg 2220
ccctgagtcg acagctctgt gagcccccac atggttgcca agggagtgtg gtaagtttcc 2280
ggcccctgga gatcccacat aggtgccagg actctagcag caaagatgca cccaccattc 2340
agcagagctc tccaggcagt tcactgaggc tggaggagga agctggaaca ccgtcagaat 2400
catggctctt gtactcacac ccaaccagta ggaaacagag ggttgaccta ggtatctatc 2460
tcaaccagac ccccttggag gctgcctgct ggtcccgccc ctggatcttg cactgtgggc 2520
cctgtggcta ctctgatctg gctgctctgg aggaggaggg cttgtttggg tgtttgtttg 2580
aatgtgggac caagcaagag tgtgagcaga ttgccttccg cctgtttaca caccgggaga 2640
tcctgagtca cctgcagggg gactgcacca gccctggtag gaacccaagc caattcaaaa 2700
gcaattaatt ggcttaggac ccaatttcca tagatgcaaa tggcagttac agacaggtta 2760
acagaagcta ctgaagtcta cagataatca aaaaacttaa tattctgttc cctacctttt 2820
ttcacttttc ctcctccaaa gagcaaaatg aaaattttgc cttagctact gcagtggaaa 2880
gagcactgaa ctaggagttg gaagacaagg atgtggtcct ggctctgcca ctggcttgct 2940
tttggacctt ggatgtgtca cctgaactct ctggacctca ggtttccatc tgtaaaatga 3000
gagtattggt tctaagattt ctcatcttct catccctagg acaagcatag tgcctgcatg 3060
cttcatgatc agtaagtcct ggctgcataa aggactctga tgtcaaaatg gaaaccaggg 3120
gacttacctt ttcacatgac ttacccctca tccgagtgtg aggttacaag caggtgtcat 3180
ggcaggaagg gctgccccaa gggcgaattc tgcagtcgac ggtaccgcgg gcccgggatc 3240
caccggatct agataactga tcataatcag ccataccaca tttgtagagg ttttacttgc 3300
tttaaaaaac ctcccacacc tccccctgaa cctgaaacat aaaatgaatg caattgttgt 3360
tgttaacttg tttattgcag cttataatgg ttacaaataa agcaatagca tcacaaattt 3420
cacaaataaa gcattttttt cactgcattc tagttgtggt ttgtccaaac tcatcaatgt 3480
atcttaacgc ccttcccaac agttgcgcag cctgaatggc gaatggacgc gccctgtagc 3540
ggactagtag tatctgcaga gggccctgcg tatgagtgca agtgggtttt aggaccagga 3600
tgaggcgggg tgggggtgcc tacctgacga ccgaccccga cccactggac aagcacccaa 3660
cccccattcc ccaaattgcg catcccctat cagagagggg gaggggaaac aggatgcggc 3720
gaggcgcgtg cgcactgcca gcttcagcac cgcggacagt gccttcgccc ccgcctggcg 3780
gcgcgcgcca ccgccgcctc agcactgaag gcgcgctgac gtcactcgcc ggtcccccgc 3840
aaactcccct tcccggccac cttggtcgcg tccgcgccgc cgccggccca gccggaccgc 3900
accacgcgag gcgcgagata ggggggcacg ggcgcgacca tctgcgctgc ggcgccggcg 3960
actcagcgct gcctcagtct gcggtgggca gcggaggagt cgtgtcgtgc ctgagagcgc 4020
agctgtgctc ctgggcaccg cgcagtccgc ccccgcggct cctggccaga ccacccctag 4080 gacccccctgc cccaagtcgc agccaagctt agaattggag cttgcttcta tagatccacc 4140
ggtcgccacc atggtgagca agggcgagga gctgttcacc ggggtggtgc ccatcctggt 4200

```
cgagctggac ggcgacgtaa acggccacaa gttcagcgtg tccggcgagg gcgagggcga   4260
tgccacctac ggcaagctga ccctgaagtt catctgcacc accggcaagc tgcccgtgcc   4320
ctggcccacc ctcgtgacca ccctgaccta cggcgtgcag tgcttcagcc gctaccccga   4380
ccacatgaag cagcacgact tcttcaagtc cgccatgccc gaaggctacg tccaggagcg   4440
caccatcttc ttcaaggacg acggcaacta caagacccgc gccgaggtga agttcgaggg   4500
cgacaccctg gtgaaccgca tcgagctgaa gggcatcgac ttcaaggagg acggcaacat   4560
cctggggcac aagctggagt acaactacaa cagccacaac gtctatatca tggccgacaa   4620
gcagaagaac ggcatcaagg tgaacttcaa gatccgccac aacatcgagg acggcagcgt   4680
gcagctcgcc gaccactacc agcagaacac ccccatcggc gacggccccg tgctgctgcc   4740
cgacaaccac tacctgagca cccagtccgc cctgagcaaa gaccccaacg agaagcgcga   4800
tcacatggtc ctgctggagt tcgtgaccgc cgccgggatc actctcggca tggacgagct   4860
gtacaagtaa agcggccgct cgagtctaga gggcccttcg aaggtaagcc tatccctaac   4920
cctctcctcg gtctcgattc tacgcgtacc ggtcatcatc accatcacca ttgagtttaa   4980
acccgctgat cagcctcgac tgtgccttct agttgccagc catctgttgt ttgcccctcc   5040
cccgtgcctt ccttgaccct ggaaggtgcc actcccactg tcctttccta ataaaatgag   5100
gaaattgcat cgcattgtct gagtaggtgt cattctattc tggggggtgg ggtggggcag   5160
gacagcaagg gggaggattg ggaagacaat agcaggcatg ctggggatgc ggtgggctct   5220
atggcttctg aggcggaaag aaccagatcc tctcttaagg tagcatcgag atttaaatta   5280
gggataacag ggtaatggcg cggccgcag gaacccctag tgatggagtt ggccactccc   5340
tctctgcgcg ctcgctcgct cactgaggcc gggcgaccaa aggtcgcccg acgcccgggc   5400
tttgcccggg cggcctcagt gagcgagcga gcgcgcagct gcctgcaggg gcgcctgatg   5460
cggtattttc tccttacgca tctgtgcggt atttcacacc gcatacgtca aagcaaccat   5520
agtacgcgcc ctgtagcggc gcattaagcg cggcgggtgt ggtggttacg cgcagcgtga   5580
ccgctacact tgccagcgcc ctagcgcccg ctcctttcgc tttcttccct tcctttctcg   5640
ccacgttcgc cggctttccc cgtcaagctc taaatcgggg gctcccttta gggttccgat   5700
ttagtgcttt acggcacctc gaccccaaaa aacttgattt gggtgatggt tcacgtagtg   5760
ggccatcgcc ctgatagacg gtttttcgcc ctttgacgtt ggagtccacg ttctttaata   5820
gtggactctt gttccaaact ggaacaacac tcaaccctat ctcgggctat tcttttgatt   5880
tataagggat tttgccgatt tcggcctatt ggttaaaaaa tgagctgatt taacaaaaat   5940
ttaacgcgaa ttttaacaaa atattaacgt ttacaatttt atggtgcact ctcagtacaa   6000
tctgctctga tgccgcatag ttaagccagc cccgacaccc gccaacaccc gctgacgcgc   6060
cctgacgggc ttgtctgctc ccggcatccg cttacagaca agctgtgacc gtctccggga   6120
gctgcatgtg tcagaggttt tcaccgtcat caccgaaacg cgcgagacga aagggcctcg   6180
tgatacgcct atttttatag gttaatgtca tgataataat ggtttcttag acgtcaggtg   6240
gcacttttcg gggaaatgtg cgcggaaccc ctatttgttt atttttctaa atacattcaa   6300
atatgtatcc gctcatgaga caataaccct gataaatgct tcaataatat tgaaaaagga   6360
agagtatgag tattcaacat ttccgtgtcg cccttattcc cttttttgcg gcattttgcc   6420
ttcctgtttt tgctcaccca gaaacgctgg tgaaagtaaa agatgctgaa gatcagttgg   6480
gtgcacgagt gggttacatc gaactggatc tcaacagcgg taagatcctt gagagttttc   6540
```

-continued

```
gccccgaaga acgttttcca atgatgagca cttttaaagt tctgctatgt ggcgcggtat   6600

tatcccgtat tgacgccggg caagagcaac tcggtcgccg catacactat tctcagaatg   6660

acttggttga gtactcacca gtcacagaaa agcatcttac ggatggcatg acagtaagag   6720

aattatgcag tgctgccata accatgagtg ataacactgc ggccaactta cttctgacaa   6780

cgatcggagg accgaaggag ctaaccgctt ttttgcacaa catgggggat catgtaactc   6840

gccttgatcg ttgggaaccg gagctgaatg aagccatacc aaacgacgag cgtgacacca   6900

cgatgcctgt agcaatggca acaacgttgc gcaaactatt aactggcgaa ctacttactc   6960

tagcttcccg gcaacaatta atagactgga tggaggcgga taaagttgca ggaccacttc   7020

tgcgctcggc ccttccggct ggctggttta ttgctgataa atctggagcc ggtgagcgtg   7080

ggtctcgcgg tatcattgca gcactggggc cagatggtaa gccctcccgt atcgtagtta   7140

tctacacgac ggggagtcag gcaactatgg atgaacgaaa tagacagatc gctgagatag   7200

gtgcctcact gattaagcat tggtaactgt cagaccaagt ttactcatat atactttaga   7260

ttgatttaaa acttcatttt taatttaaaa ggatctaggt gaagatcctt tttgataatc   7320

tcatgaccaa aatcccttaa cgtgagtttt cgttccactg agcgtcagac cccgtagaaa   7380

agatcaaagg atcttcttga gatccttttt ttctgcgcgt aatctgctgc ttgcaaacaa   7440

aaaaaccacc gctaccagcg gtggtttgtt tgccggatca agagctacca actctttttc   7500

cgaaggtaac tggcttcagc agagcgcaga taccaaatac tgtccttcta gtgtagccgt   7560

agttaggcca ccacttcaag aactctgtag caccgcctac atacctcgct ctgctaatcc   7620

tgttaccagt ggctgctgcc agtggcgata agtcgtgtct taccgggttg gactcaagac   7680

gatagttacc ggataaggcg cagcggtcgg gctgaacggg gggttcgtgc acacagccca   7740

gcttggagcg aacgacctac accgaactga gatacctaca gcgtgagcta tgagaaagcg   7800

ccacgcttcc cgaagggaga aaggcggaca ggtatccggt aagcggcagg gtcggaacag   7860

gagagcgcac gagggagctt ccagggggaa acgcctggta tctttatagt cctgtcgggt   7920

ttcgccacct ctgacttgag cgtcgatttt tgtgatgctc gtcagggggg cggagcctat   7980

ggaaaaacgc cagcaacgcg gcctttttac ggttcctggc cttttgctgg ccttttgctc   8040

acatgt                                                              8046
```

METHODS FOR TREATING NEURODEGENERATIVE DISORDERS

CROSS-REFERENCE TO RELATED APPLICATIONS

The present application is a 35 U.S.C. § 371 national phase application from, and claims priority to, International Application No. PCT/US2020/030409, filed Apr. 29, 2020, which claims priority under 35 U.S.C. § 119 (e) to U.S. Provisional Application No. 62/840,235, filed Apr. 29, 2019, all of which applications are incorporated by reference herein in their entireties.

REFERENCE TO AN ELECTRONIC SEQUENCE LISTING

The present application contains a Sequence Listing which has been submitted in ASCII format via EFS Web and is hereby incorporated by reference in its entirety. Said txt file, created on Apr. 28, 2020, is named 205961-7042WO1 (00175) SequenceListing.txt and is 20,480 bytes in size.

BACKGROUND OF THE INVENTION

Parkinson's disease (PD) is a neurodegenerative disorder characterized by loss of dopamine (DA)-producing neurons in the substantia nigra pars compacta (SNc), decreased levels of DA primarily in the caudate nucleus and putamen, accumulation of insoluble α-synuclein aggregates (i.e., Lewy bodies and Lewy neurites), and a slowly progressive worsening of clinical symptoms. Current pharmacotherapies for PD improve many of the motor signs and symptoms of the disease but no drug has yet been identified that definitively slows or stops the progression of PD. Disease modifying therapies that can alter clinical progression are sorely needed, however, efforts at finding such therapies have been limited in part due to uncertainty regarding the pathogenic processes contributing to DA neuron degeneration in PD that should be targeted by a disease modifying therapy. Parkinson's disease is one of several neurodegenerative diseases, including dementia with Lewy bodies, multiple system atrophy, and other rarer diseases, that are characterized by abnormal α-synuclein metabolism, accumulation, and aggregation.

There remains a need for disease modifying therapies for neurodegenerative disorders such as PD, Lewy body dementia, multi-system atrophy and pure autonomic failure. The present application addresses this need.

SUMMARY OF THE INVENTION

As described herein, the present invention relates to compositions and methods for treating synucleinopathies including Lewy body dementia, multi-system atrophy, or pure autonomic failure.

In one aspect, the invention includes a method of treating Lewy body dementia in a subject in need thereof. The method comprises administering a composition comprising GM1 or a derivative thereof to the subject.

In another aspect, the invention includes a method of treating multi-system atrophy in a subject in need thereof. The method comprises administering a composition comprising GM1 or a derivative thereof to the subject.

In another aspect, the invention includes a method of treating pure autonomic failure in a subject in need thereof.

The method comprises administering a composition comprising GM1 or a derivative thereof to the subject.

In another aspect, the invention includes a method of treating a disease or disorder in a subject in need thereof, wherein the disease or disorder is selected from the group consisting of inherited forms of Parkinson's disease with synuclein gene mutations, lysosomal storage disorders associated with abnormal alpha synuclein deposits in the brain, Sanfilippo syndrome and related Mucopolysaccaridoses, GlcCerase (GBA) mutations accompanied by abnormal synuclein accumulation. The method comprises administering a composition comprising GM1 or a derivative thereof to the subject.

In various embodiments of the above aspects or any other aspect of the invention delineated herein, the GM1 or derivative thereof is administered by injection, orally or intranasally. In certain embodiments, the injection is intraperitoneal.

In certain embodiments, the GM1 or derivative thereof is conjugated or engineered.

In certain embodiments, the composition further comprises a pharmaceutically acceptable carrier.

In certain embodiments, the GM1 or derivative thereof is administered in a nanoparticle or exosome.

In certain embodiments, the composition comprising GM1 is administered to the subject after Lewy body dementia has become advanced. In certain embodiments, the composition comprising GM1 is administered to the subject at an early stage of Lewy body dementia.

In certain embodiments, the composition comprising GM1 is administered to the subject after multi-system atrophy has become advanced. In certain embodiments, the composition comprising GM1 is administered to the subject at an early stage of multi-system atrophy.

In certain embodiments, the composition comprising GM1 is administered to the subject after pure autonomic failure has become advanced. In certain embodiments, the composition comprising GM1 is administered to the subject at an early stage of autonomic failure.

In certain embodiments, the composition comprising GM1 is administered to the subject after the disease or disorder has become advanced. In certain embodiments, the composition comprising GM1 is administered to the subject at an early stage of the disease or disorder.

In certain embodiments, the GM1 is synthetic. In certain embodiments, the GM1 is porcine or ovine. In certain embodiments, the GM1 is derived from pig brain or from sheep brain.

In another aspect, the invention includes a method of treating a disease or disorder in a subject in need thereof, wherein the disease or disorder is selected from the group consisting of Lewy body dementia, multi-system atrophy, pure autonomic failure, inherited forms of Parkinson's disease with synuclein gene mutations, lysosomal storage disorders associated with abnormal alpha synuclein deposits in the brain, Sanfilippo syndrome and related Mucopolysaccaridoses, GlcCerase (GBA) mutations accompanied by abnormal synuclein accumulation. The method comprises administering a nucleic acid encoding sialidase Neu3 to the subject.

In another aspect, the invention includes a method of treating a disease or disorder in a subject in need thereof, wherein the disease or disorder is selected from the group consisting of Lewy body dementia, multi-system atrophy, pure autonomic failure, inherited forms of Parkinson's disease with synuclein gene mutations, lysosomal storage disorders associated with abnormal alpha synuclein deposits in the brain, Sanfilippo syndrome and related Mucopolysaccaridoses, GlcCerase (GBA) mutations accompanied by abnormal synuclein accumulation. The method comprises administering a nucleic acid encoding B3GalT4 to the subject.

In various embodiments of the above aspects or any other aspect of the invention delineated herein, the nucleic acid is comprised in an engineered virus, a plasmid or a non-viral vector. In certain embodiments, the engineered virus is an adeno-associated virus (AAV).

In certain embodiments, expression of sialidase Neu3 is under control of a neuron specific promoter. In certain embodiments, expression of B3GalT4 or is under control of a neuron specific promoter.

In certain embodiments, the nucleic acid comprises a nucleotide sequence that is at least 85%, 90%, 91%, 92%, 93%, 94%, 95%, 96%, 97%, 98%, 99%, or 100% identical to SEQ ID NO: 2. In certain embodiments, the nucleic acid comprises a nucleotide sequence that is at least 85%, 90%, 91%, 92%, 93%, 94%, 95%, 96%, 97%, 98%, 99%, or 100% identical to SEQ ID NO: 1.

In certain embodiments, the engineered virus is administered to the subject by intracranial stereotaxic injection.

In certain embodiments, the nucleic acid is administered in a nanoparticle or exosome.

In certain embodiments, the nucleic acid is administered to the subject after the disease or disorder has become advanced. In certain embodiments, the nucleic acid is administered to the subject at an early stage of the disease or disorder.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A shows that at 3 weeks following AAV-A53T α-synuclein injection, saline-treated animals (N=15) favored the use of the limb ipsilateral to the injection and this response continued to be observed at 6 weeks post virus injection. In animals that received GM1 administration beginning 24 hours after AAV-A53T α-synuclein injection (N=21), use of the limb ipsilateral to the injection was also favored at 3 weeks post injection, but with continued GM1 use, this response was reduced by 6 weeks post virus injection. **P<0.0001 vs. baseline (Bx); *P=0.0005; ^^^P=0.0003 vs. Bx; ^^^P=0.0055 vs. 3 wk. FIG. 1B shows striatal DA levels were significantly higher in GM1-treated animals vs. saline-treated animals (P=0.0072). FIG. 1C shows that striatal DOPAC/DA ratios were significantly higher in saline-treated animas vs. GM1-treated animals (P=0.0040).

FIGS. 2A-2B show that when assessed 1 week following AAV-A53T α-synuclein injection, levels of striatal α-synuclein were no different in saline (N=6) vs. GM1-treated animals (N=6), suggesting no influence of GM1 on AAV-A53T α-synuclein transduction or transport of α-synuclein to the striatum. Representative Western blots (obtained using Protein Simple Wes system) are shown after cropping (full length images of blots are presented as FIG. 8). FIG. 2C shows that double label immunofluorescence 1 week after AAV-A53T α-synuclein injection showed no differences between saline and GM1-treated animals in α-synuclein accumulation in TH+ neurons in the SNc.

FIG. 3A shows that there was a significant protective effect of early start GM1 administration (N=17) on the number of TH+ cells (*P=0.0002) FIG. 3B shows that there was a significant protective effect of early start GM1 administration on the number of Nissl-stained cells (*P=0.0004 vs. saline-treated) in the SNc, compared to saline-treated animals (N=13). FIG. 3C shows immunohistochemical staining of TH+ cells in the SNc showed significant cell loss in a saline-treated animal. FIG. 3D shows a partial sparing of TH+ cells in a GM1-treated animal.

FIG. 4A shows that at 3 weeks following AAV-A53T α-synuclein injection, saline-treated animals (N=11) showed a significant preference for using the limb ipsilateral to the injection that bias continued to be observed at 8 weeks post virus injection (**P<0.0001 vs. baseline (Bx). FIG. 4B shows that in the delayed start GM1 group (N=17), animals also showed a significant preference for using the limb ipsilateral to the injection at 3 weeks post virus injection (**P<0.0001 vs. Bx) but after 5 weeks of GM1 use (starting immediately after 3 week testing), limb use asymmetry was significantly reduced (*P=0.0075 vs. 3 weeks). FIG. 4C shows striatal DA levels were significantly higher in GM1-treated animals (N=17) vs. saline-treated animals (N=11) (P=0.0013 vs. saline-treated). FIG. 4**D shows that DOPAC/DA ratios were lower in the GM1-treated (N=17) but not significantly reduced compared to saline-treated animals (N=11).

FIG. 5A shows that there was a significant protective effect of delayed start GM1 administration (N=17) on the number of TH+ cells (P=0.0013). FIG. 5B shows that there was a significant protective effect of delayed start GM1 administration on the number of Nissl-stained cells (*P=0.0008 vs. saline-treated) in the SNc, compared to saline-treated animals (N=12). FIG. 5C shows immunohistochemical staining of TH+ cells in the SNc showed significant cell loss in a saline-treated animal. FIG. 5D shows that TH+ cells in the SNc showed a partial sparing of TH+ cells in a GM1-treated animal.

FIG. 6A shows that the size distributions of striatal α-synuclein-positive aggregates in saline-treated (N=6) (dark grey bars) compared to early start GM1-treated (light grey bars) animals (N=6) were significantly different (Kolmogorov-Smirnov D=0.2945, P<0.0001), with a clear shift to larger numbers of smaller sized aggregates and fewer larger sized aggregates in the early GM1 group compared to the saline-treated group.

FIG. 6B shows that the size distributions of striatal α-synuclein positive aggregates in the delayed GM1-treated group (N=8) (light grey bars) was also significantly different (Kolmogorov-Smirnov D=0.154, P<0.0001) than size distribution of aggregates in the saline-treated group (N=7)

(dark grey bars), with greater numbers of larger sized aggregates in the saline-treated group compared to the GM1 group. FIG. 6C shows photomicrographs of α-synuclein immunohistochemical staining in the striatum of saline treated (left) and early start GM1-treated (right) animals. Sizes of aggregates are notably smaller in the GM1-treated animals. Arrow points to large α-synuclein-positive aggregate. FIG. 6D shows photomicrographs of α-synuclein immunohistochemical staining in the striatum of saline-treated (left) and delayed start GM1-treated (right) animals. Sizes of aggregates are smaller in the delayed start GM1-treated animal, but the effect was not as dramatic as in the early-start GM1 animals. Arrow points to large α-synuclein-positive aggregate.

DETAILED DESCRIPTION

Definitions

Figure 1B:
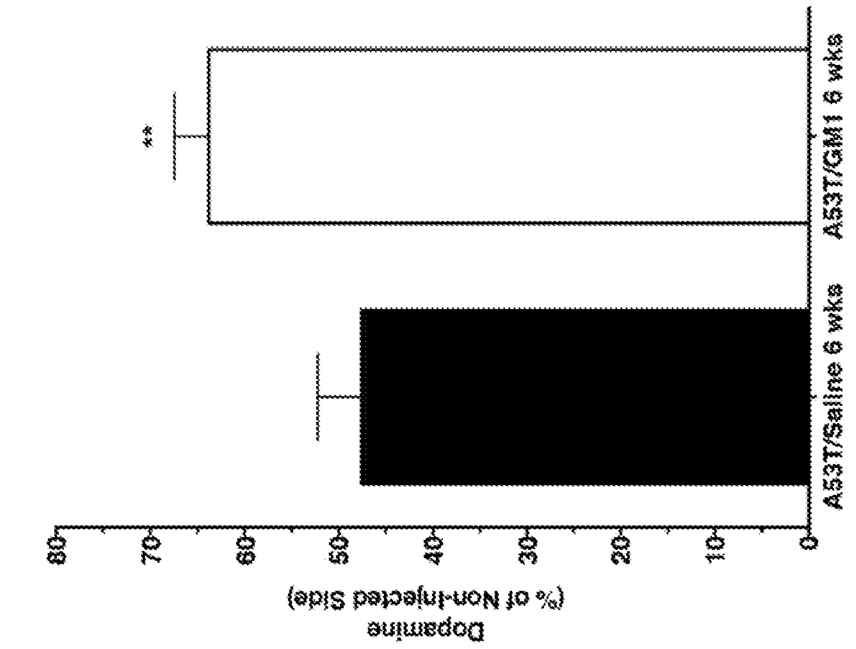
FIGS. 1A-1C illustrate the protective effect of early start GM1 administration (beginning 24 hours after AAV-A53T α-synuclein injection) on spontaneous forelimb use and striatal dopamine levels.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "cleavage" refers to the breakage of covalent bonds, such as in the backbone of a nucleic acid molecule. Cleavage can be initiated by a variety of methods, including, but not limited to, enzymatic or chemical hydrolysis of a phosphodiester bond. Both single-stranded cleavage and double-stranded cleavage are possible. Double-stranded cleavage can occur as a result of two distinct single-stranded cleavage events. DNA cleavage can result in the production of either blunt ends or staggered ends. In certain embodiments, fusion polypeptides may be used for targeting cleaved double-stranded DNA.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for the ability to bind antigens using the functional assays described herein.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of a composition includes, e.g., subcutaneous (s.c.), intravenous (i.v.), intramuscular (i.m.), or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

A "target site" or "target sequence" refers to a genomic nucleic acid sequence that defines a portion of a nucleic acid to which a binding molecule may specifically bind under conditions sufficient for binding to occur.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "transgene" refers to the genetic material that has been or is about to be artificially inserted into the genome of an animal, particularly a mammal and more particularly a mammalian cell of a living animal.

To "treat" a disease as the term is used herein, means to reduce the frequency or severity of at least one sign or symptom of a disease or disorder experienced by a subject.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates to compositions and methods for treating synucleinopathies including but not limited to Lewy body dementia, multi-system atrophy, pure autonomic failure, inherited forms of Parkinson's disease with synuclein gene mutations, lysosomal storage disorders associated with abnormal alpha synuclein deposits in the brain (including disorders such as Sanfilippo syndrome and related Mucopolysaccaridoses), GlcCerase (GBA) mutations accompanied by abnormal synuclein accumulation, in a subject in need thereof.

In one aspect, the invention provides a method of treating Lewy body dementia in a subject in need thereof, the method comprising administering a composition comprising GM1 or a derivative thereof to the subject.

In another aspect, the invention provides a method of treating multi-system atrophy in a subject in need thereof, the method comprising administering a composition comprising GM1 or a derivative thereof to the subject.

In another aspect, the invention provides a method of treating pure autonomic failure in a subject in need thereof, the method comprising administering a composition comprising GM1 or a derivative thereof to the subject. In some embodiments, the administration is systemic.

In some embodiments, the administration of the GM1 or derivative thereof is systemic. In some embodiments, the GM1 or derivative thereof is administered by injection, orally or intranasally. In some embodiments, the injection is intraperitoneal.

In some embodiments, the GM1 or derivative thereof is administered via nanoparticles.

In some embodiments, the GM1 or derivative thereof is conjugated or engineered.

In some embodiments, the composition further comprises a pharmaceutically acceptable carrier.

In some embodiments, the composition comprising GM1 is administered to the subject after the Lewy body dementia has become advanced. In some embodiments, the composition comprising GM1 is administered to the subject after the multi-system atrophy has become advanced. In some embodiments, the composition comprising GM1 is administered to the subject after the pure autonomic failure has become advanced.

In certain aspects, the invention provides a method of treating a synucleinopathy selected from the group consisting of Lewy body dementia, multi-system atrophy, pure autonomic failure, inherited forms of Parkinson's disease with synuclein gene mutations, lysosomal storage disorders associated with abnormal alpha synuclein deposits in the brain (including disorders such as Sanfilippo syndrome and related Mucopolysaccaridoses), GlcCerase (GBA) mutations with abnormal synuclein accumulation. The method comprises administering a nucleic acid encoding sialidase Neu3 to the subject. Administering a nucleic acid encoding sialidase Neu3 would in effect increase GM1 levels in the subject. In some embodiments, the nucleic acid is comprised in an engineered virus, a plasmid or a non-viral vector. In some embodiments, the engineered virus is an adeno-associated virus (AAV). In some embodiments, expression of sialidase Neu3 is under control of a neuron specific promoter. In some embodiments, the engineered virus is administered to the subject by intracranial stereotaxic injection.

In certain aspects, the invention provides a method of treating a synucleinopathy selected from the group consisting of Lewy body dementia, multi-system atrophy, pure autonomic failure, inherited forms of Parkinson's disease with synuclein gene mutations, lysosomal storage disorders associated with abnormal alpha synuclein deposits in the brain (including disorders such as Sanfilippo syndrome and related Mucopolysaccaridoses), GlcCerase (GBA) mutations with abnormal synuclein accumulation. The method comprises administering a nucleic acid encoding B3GalT4 to the subject. Administering a nucleic acid encoding B3GalT4 would in effect increase GM1 levels in the subject. In some embodiments, the nucleic acid is comprised in an engineered virus, a plasmid or a non-viral vector. In some embodiments, the engineered virus is an adeno-associated virus (AAV). In some embodiments, expression of B3GalT4 is under control of a neuron specific promoter. In some embodiments, the engineered virus is administered to the subject by intracranial stereotaxic injection.

Without wishing to be bound by theory, one potential pathogenic mechanism contributing to PD and other synucleinopathies may involve dysregulation of ganglioside synthesis and expression that may contribute to abnormal metabolism, accumulation, and aggregation of α-synuclein as well as contribute to the overall vulnerability and degeneration of DA neurons in PD and other neuron types in other synucleinopathies. Gangliosides are glycosphingolipids bearing a ceramide anchor, an oligosaccharide, and one or more sialic acid residues. The major ganglioside species in brain are GM1, GD1a, GD1b, and GT1b, all contributing to the lipid composition of plasma and intracellular membranes. GM1 and other gangliosides are components of membrane signaling domains called lipid rafts, and in this regard, GM1 contributes to regulating signal transduction for directing neuronal development and cell survival and for modulating a wide variety of cell functions. Further, at least four proteins associated with PD (LRRK2, Parkin, PINK1, and α-synuclein), have been found to associate with lipid rafts and some co-localize with GM1 (along with other raft markers) suggesting that alterations of the GM1-raft association could influence cellular functions dependent on these proteins. In addition to effects exerted at the plasma membrane, GM1 also acts intracellularly where it influences $Ca^{2+}$ homeostasis, mitochondrial function, and lysosomal integrity, among other processes critical for normal cell function and survival. Lysosomal dysfunction can result in neurodegeneration and increased α-synuclein accumulation has been linked to lysosomal dysfunction. Preclinical studies have shown that treatment with GM1 can be neurotrophic or neuroprotective following different types of lesions resulting in significant biochemical and behavioral recovery. In particular, GM1 rescued damaged SNc DA neurons, increased striatal DA levels and enhanced DA synthetic capacity in residual DA neurons in neurotoxin (MPTP)-induced models of PD. Clinical studies of GM1 in PD patients have also provided evidence for slowing of symptom progression with GM1 use. Despite the positive preclinical and clinical findings related to GM1 and PD, the mechanisms through which GM1 exerts its potential neuroprotective effects are still uncertain.

Alpha-synuclein fibrillation and aggregation are considered to be important contributors to PD pathophysiology, with α-synuclein-containing cytoplasmic inclusions a histological hallmark of the disease. Alpha-synuclein accumulation and aggregation (i.e., synucleiopathy) also occurs in synucleinopathies other than PD as well as across of range of storage disorders, such as in Sanfilippo syndrome (mucopolysaccharidosis type III). Recent development of animal models of PD and other synucleinopathies that reproduce this aspect of the disease have been achieved in transgenic animals expressing human α-synuclein under control of a variety of promoters or using viral vector delivery of α-synuclein directly to SNc DA neurons or into other neuron types in other brain regions. In particular, several studies have demonstrated PD-relevant and progressive neuropathological (including development of insoluble α-synuclein aggregates) and behavioral features in mice, rats, and non-human primates following SNc-targeted AAV-driven overexpression of human mutant A53T α-synuclein. Binding of α-synuclein to GM1, in vitro, inhibits fibril formation, dependent upon the amount of GM1 present, with a similar effect of GM1 on the A53T mutant of α-synuclein. Additionally, the interaction of GM1 and α-synuclein in vitro led to a complete resistance to fibrillar aggregation of acetylated α-synuclein, raising the possibility that binding to GM1-rich membranes could protect monomeric α-synuclein from pathogenic aggregation. Using the AAV-A53T α-synuclein rat model, a study was conducted to investigate the extent to which GM1 ganglioside administration in vivo could protect against α-synuclein toxicity and development of PD-relevant pathological changes and behavioral deficits.

Vectors

Provided in the invention are vectors. In certain embodiments, the vector is an adeno-associated viral (AAV) vector. In certain embodiments, the vector (e.g. AAV vector) encodes the B3GALT4 gene, which is involved in GM1 ganglioside biosynthesis.

AAV, a parvovirus belonging to the genus Dependovirus, has several features that make it particularly well suited for gene therapy applications. For example, AAV can infect a wide range of host cells, including non-dividing cells. Furthermore, AAV can infect cells from a variety of species. Importantly, AAV has not been associated with any human or animal disease, and does not appear to alter the physiological properties of the host cell upon integration. Finally, AAV is stable at a wide range of physical and chemical conditions, which lends itself to production, storage, and transportation requirements.

The AAV genome, which is a linear, single-stranded DNA molecule containing approximately 4,700 nucleotides (the AAV-2 genome consists of 4,681 nucleotides, the AAV-4 genome 4,767), generally comprises an internal non-repeating segment flanked on each end by inverted terminal repeats (ITRs). The ITRs are approximately 145 nucleotides in length (AAV-1 has ITRs of 143 nucleotides) and have multiple functions, including serving as origins of replication, and as packaging signals for the viral genome.

The internal non-repeated portion of the genome includes two large open reading frames (ORFs), known as the AAV replication (rep) and capsid (cap) regions. These ORFs encode replication and capsid gene products, which allow for the replication, assembly, and packaging of a complete AAV virion. More specifically, a family of at least four viral proteins are expressed from the AAV rep region: Rep 78, Rep 68, Rep 52, and Rep 40, all of which are named for their apparent molecular weights. The AAV cap region encodes at least three proteins: VP1, VP2, and VP3.

AAV is a helper-dependent virus, that is, it requires co-infection with a helper virus (e.g., adenovirus, herpesvirus, or vaccinia virus) in order to form functionally complete AAV virions. In the absence of co-infection with a helper virus, AAV establishes a latent state in which the viral genome inserts into a host cell chromosome or exists in an episomal form, but infectious virions are not produced. Subsequent infection by a helper virus "rescues" the integrated genome, allowing it to be replicated and packaged into viral capsids, thereby reconstituting the infectious virion. While AAV can infect cells from different species, the helper virus must be of the same species as the host cell. Thus, for example, human AAV replicates in canine cells that have been co-infected with a canine adenovirus.

To produce infectious recombinant AAV (rAAV) containing a heterologous nucleic acid sequence, a suitable host cell line can be transfected with an AAV vector containing the heterologous nucleic acid sequence, but lacking the AAV helper function genes, rep and cap. The AAV-helper function genes can then be provided on a separate vector. Also, only the helper virus genes necessary for AAV production (i.e., the accessory function genes) can be provided on a vector, rather than providing a replication-competent helper virus (such as adenovirus, herpesvirus, or vaccinia).

Collectively, the AAV helper function genes (i.e., rep and cap) and accessory function genes can be provided on one or more vectors. Helper and accessory function gene products can then be expressed in the host cell where they will act in trans on rAAV vectors containing the heterologous nucleic acid sequence. The rAAV vector containing the heterologous nucleic acid sequence will then be replicated and packaged as though it were a wild-type (wt) AAV genome, forming a recombinant virion. When a patient's cells are infected with the resulting rAAV virions, the heterologous nucleic acid sequence enters and is expressed in the patient's cells. Because the patient's cells lack the rep and cap genes, as well as the accessory function genes, the rAAV cannot further replicate and package their genomes. Moreover, without a source of rep and cap genes, wtAAV cannot be formed in the patient's cells.

There are eleven known AAV serotypes, AAV-1 through AAV-11 (Mori, et al., 2004, Virology 330 (2): 375-83). AAV-2 is the most prevalent serotype in human populations; one study estimated that at least 80% of the general population has been infected with wt AAV-2 (Berns and Linden, 1995, Bioessays 17:237-245). AAV-3 and AAV-5 are also prevalent in human populations, with infection rates of up to 60% (Georg-Fries, et al., 1984, Virology 134:64-71). AAV-1 and AAV-4 are simian isolates, although both serotypes can transduce human cells (Chiorini, et al., 1997, J Virol 71:6823-6833; Chou, et al., 2000, Mol Ther 2:619-623). Of the six known serotypes, AAV-2 is the best characterized. For instance, AAV-2 has been used in a broad array of in vivo transduction experiments, and has been shown to transduce many different tissue types including: mouse (U.S. Pat. Nos. 5,858,351; 6,093,392), dog muscle; mouse liver (Couto, et al., 1999, Proc. Natl. Acad. Sci. USA 96:12725-12730; Couto, et al., 1997, J. Virol. 73:5438-5447; Nakai, et al., 1999, J. Virol. 73:5438-5447; and, Snyder, et al., 1997, Nat. Genet. 16:270-276); mouse heart (Su, et al., 2000, Proc. Natl. Acad. Sci. USA 97:13801-13806); rabbit lung (Flotte, et al., 1993, Proc. Natl. Acad. Sci. USA 90:10613-10617); and rodent photoreceptors (Flannery et al., 1997, Proc. Natl. Acad. Sci. USA 94:6916-6921).

The broad tissue tropism of AAV-2 may be exploited to deliver tissue-specific transgenes. For example, AAV-2 vectors have been used to deliver the following genes: the cystic fibrosis transmembrane conductance regulator gene to rabbit lungs (Flotte, et al., 1993, Proc. Natl. Acad. Sci. USA 90:10613-10617); Factor NIII gene (Burton, et al., 1999, Proc. Natl. Acad. Sci. USA 96:12725-12730) and Factor IX gene (Nakai, et al., 1999, J. Virol. 73:5438-5447; Snyder, et al., 1997, Nat. Genet. 16:270-276; U.S. Pat. No. 6,093,392) to mouse liver, dog, and mouse muscle (U.S. Pat. No. 6,093,392); erythropoietin gene to mouse muscle (U.S. Pat. Nos. 5,858,351); vascular endothelial growth factor (VEGF) gene to mouse heart (Su, et al., 2000, Proc. Natl. Acad. Sci. USA 97:13801-13806); and aromatic 1-amino acid decarboxylase gene to monkey neurons. Expression of certain rAAV-delivered transgenes has therapeutic effect in laboratory animals; for example, expression of Factor IX was reported to have restored phenotypic normalcy in dog models of hemophilia B (U.S. Pat. No. 6,093,392). Moreover, expression of rAAV-delivered NEGF to mouse myocardium resulted in neovascular formation (Su, et al., 2000, Proc. Natl. Acad. Sci. USA 97:13801-13806), and expression of rAAV-delivered AADC to the brains of parkinsonian monkeys resulted in the restoration of dopaminergic function.

Delivery of a protein of interest to the cells of a mammal is accomplished by first generating an AAV vector comprising DNA encoding the protein of interest and then administering the vector to the mammal. Thus, the invention should be construed to include AAV vectors comprising DNA encoding the polypeptide(s) of interest. Once armed with the present invention, the generation of AAV vectors comprising DNA encoding this/these polypeptide(s) s will be apparent to the skilled artisan.

In certain embodiments, the rAAV vector of the invention comprises several essential DNA elements. In certain embodiments, these DNA elements include at least two copies of an AAV ITR sequence, a promoter/enhancer element, a transcription termination signal, any necessary 5' or 3' untranslated regions which flank DNA encoding the protein of interest or a biologically active fragment thereof. The rAAV vector of the invention may also include a portion of an intron of the protein on interest. Also, optionally, the rAAV vector of the invention comprises DNA encoding a mutated polypeptide of interest.

In certain embodiments, the vector comprises a promoter/regulatory sequence that comprises a promiscuous promoter which is capable of driving expression of a heterologous gene to high levels in many different cell types. Such promoters include, but are not limited to the cytomegalovirus (CMV) immediate early promoter/enhancer sequences, the Rous sarcoma virus promoter/enhancer sequences and the like. In certain embodiments, the promoter/regulatory sequence in the rAAV vector of the invention is the CMV immediate early promoter/enhancer. However, the promoter sequence used to drive expression of the heterologous gene may also be an inducible promoter, for example, but not limited to, a steroid inducible promoter, or may be a tissue specific promoter, such as, but not limited to, the skeletal α-actin promoter which is muscle tissue specific and the muscle creatine kinase promoter/enhancer, and the like.

In certain embodiments, the rAAV vector of the invention comprises a transcription termination signal. While any transcription termination signal may be included in the vector of the invention, in certain embodiments, the transcription termination signal is the SV40 transcription termination signal.

In certain embodiments, the rAAV vector of the invention comprises isolated DNA encoding the polypeptide of interest, or a biologically active fragment of the polypeptide of interest. The invention should be construed to include any mammalian sequence of the polypeptide of interest, which is either known or unknown. Thus, the invention should be construed to include genes from mammals other than humans, which polypeptide functions in a substantially similar manner to the human polypeptide. Preferably, the nucleotide sequence comprising the gene encoding the polypeptide of interest is about 50% homologous, more preferably about 70% homologous, even more preferably about 80% homologous and most preferably about 90% homologous to the gene encoding the polypeptide of interest.

Further, the invention should be construed to include naturally occurring variants or recombinantly derived mutants of wild type protein sequences, which variants or mutants render the polypeptide encoded thereby either as therapeutically effective as full-length polypeptide, or even more therapeutically effective than full-length polypeptide in the gene therapy methods of the invention.

The invention should also be construed to include DNA encoding variants which retain the polypeptide's biological activity. Such variants include proteins or polypeptides which have been or may be modified using recombinant DNA technology, such that the protein or polypeptide possesses additional properties which enhance its suitability for use in the methods described herein, for example, but not limited to, variants conferring enhanced stability on the protein in plasma and enhanced specific activity of the protein. Analogs can differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function.

The invention is not limited to the specific rAAV vector exemplified in the experimental examples; rather, the invention should be construed to include any suitable AAV vector, including, but not limited to, vectors based on AAV-1, AAV-2, AAV-3, AAV-4, AAV-5, AAV-6, AAV-9, and the like.

Also included in the invention is a method of treating a mammal having a disease or disorder in an amount effective to provide a therapeutic effect. The method comprises administering to the mammal an rAAV vector encoding the polypeptide of interest. Preferably, the mammal is a human.

Typically, the number of viral vector genomes/mammal which are administered in a single injection ranges from about $1\times10^{8}$ to about $5\times10^{16}$. Preferably, the number of viral vector genomes/mammal which are administered in a single injection is from about $1\times10^{10}$ to about $1\times10^{15}$; more preferably, the number of viral vector genomes/mammal which are administered in a single injection is from about $5\times10^{10}$ to about $5\times10^{15}$; and, most preferably, the number of viral vector genomes which are administered to the mammal in a single injection is from about $5\times10^{11}$ to about $5\times10^{14}$.

When the method of the invention comprises multiple site simultaneous injections, or several multiple site injections comprising injections into different sites over a period of several hours (for example, from about less than one hour to about two or three hours) the total number of viral vector genomes administered may be identical, or a fraction thereof or a multiple thereof, to that recited in the single site injection method.

For administration of the rAAV vector of the invention in a single site injection, in certain embodiments a composition comprising the virus is injected directly into an organ of the subject (such as, but not limited to, the liver of the subject).

For administration to the mammal, the rAAV vector may be suspended in a pharmaceutically acceptable carrier, for example, HEPES buffered saline at a pH of about 7.8. Other useful pharmaceutically acceptable carriers include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The rAAV vector of the invention may also be provided in the form of a kit, the kit comprising, for example, a freeze-dried preparation of vector in a dried salts formulation, sterile water for suspension of the vector/salts composition and instructions for suspension of the vector and administration of the same to the mammal.

In certain embodiments, the vector is an AAV-2 vector. In certain embodiments, the vector comprises an AAV backbone and a human B3GALT4 gene. In certain embodiments, the vector comprises the nucleotide sequence set forth in SEQ ID NO: 1. In certain embodiments, the vector is at least 70%, 80%, 85%, 90%, 91%, 92%, 93%, 94%, 95%, 96%, 97%, 98%, 99%, or 100% identical to SEQ ID NO: 1. In certain embodiments, the vector comprises an AAV backbone and a Neu3 (sialidase) gene. In certain embodiments, the vector comprises the nucleotide sequence set forth in SEQ ID NO: 2. In certain embodiments, the vector is at least 70%, 80%, 85%, 90%, 91%, 92%, 93%, 94%, 95%, 96%, 97%, 98%, 99%, or 100% identical to SEQ ID NO: 2.

AAV-Syn-hB3GATL4-SynEGFP (SEQ ID NO: 1)

```
   1 CCTGCAGGCA GCTGCGCGCT CGCTCGCTCA CTGAGGCCGC CCGGGCAAAG
  51 CCCGGGCGTC GGGCGACCTT TGGTCGCCCG GCCTCAGTGA GCGAGCGAGC
 101 GCGCAGAGAG GGAGTGGCCA ACTCCATCAC TAGGGGTTCC TGCGGCCAAT
 151 TCAGTCGATA ACTATAACGG TCCTAAGGTA GCGATTTAAA TACGCGCTCT
 201 CTTAAGGTAG CCCCGGGACG CGTCAATTCG CGCCTGAGTT GAATATCAAC
 251 ACTACAAACC GAGTATCTGC AGAGGGCCCT GCGTATGAGT GCAAGTGGGT
 301 TTTAGGACCA GGATGAGGCG GGGTGGGGGT GCCTACCTGA CGACCGACCC
 351 CGACCCACTG GACAAGCACC CAACCCCCAT TCCCCAAATT GCGCATCCCC
 401 TATCAGAGAG GGGGAGGGGA AACAGGATGC GGCGAGGCGC GTGCGCACTG
 451 CCAGCTTCAG CACCGCGGAC AGTGCCTTCG CCCCCGCCTG GCGGCGCGCG
 501 CCACCGCCGC CTCAGCACTG AAGGCGCGCT GACGTCACTC GCCGGTCCCC
 551 CGCAAACTCC CCTTCCCGGC CACCTTGGTC GCGTCCGCGC CGCCGCCGGC
 601 CCAGCCGGAC CGCACCACGC GAGGCGCGAG ATAGGGGGGC ACGGGCGCGA
 651 CCATCTGCGC TGCGGCGCCG GCGACTCAGC GCTGCCTCAG TCTGCGGTGG
 701 GCAGCGGAGG AGTCGTGTCG TGCCTGAGAG CGCAGCTGTG CTCCTGGGCA
 751 CCGCGCAGTC CGCCCCCGCG GCTCCTGGCC AGACCACCCC TAGGACCCCC
 801 TGCCCCAAGT CGCAGCCTTC GAATTCCCAC CATGCAGCTC AGGCTCTTCC
 851 GGCGCCTCCT TCTCGCCGCT TTGCTGCTGG TGATCGTCTG GACCCTCTTC
 901 GGGCCTTCGG GGTTGGGGGA GGAGCTGCTG AGCCTCTCAC TAGCCTCCCT
 951 GCTCCCAGCC CCCGCCTCAC CGGGGCCGCC CCTGGCCCTG CCCCGCCTCT
1001 TGATCCCCAA CCAGGAAGCT TGCAGTGGTC CCGGGGCCCC TCCCTTCCTG
1051 CTCATCCTGG TGTGCACGGC TCCGGAGAAC CTGAACCAGA GAAACGCCAT
1101 TCGGGCTTCG TGGGGCGGGC TGCGCGAGGC CCGGGGGCTC AGGGTACAGA
1151 CGCTATTCTT GCTGGGAGAG CCGAACGCAC AGCACCCCGT GTGGGGTTCC
1201 CAGGGGAGTG ACCTGGCCTC GGAGTCAGCA GCCCAGGGGG ATATCTTGCA
1251 GGCCGCCTTC CAGGACTCCT ACCGCAACCT CACCCTAAAG ACCCTCAGCG
1301 GGCTGAACTG GGCTGAGAAA CACTGCCCCA TGGCCCGATA CGTCCTCAAG
1351 ACGGACGATG ATGTGTATGT CAACGTCCCT GAACTGGTAT CAGAGCTGGT
1401 CTTGCGAGGG GGCCGTTGGG GGCAATGGGA GAGAAGCACG GAACCCCAGA
1451 GAGAGGCTGA GCAGGAAGGA GGCCAGGTTT TGCACAGCGA GGAAGTGCCT
1501 CTTCTGTACT TGGGCCGGGT GCACTGGCGC GTGAACCCCT CTCGGACACC
1551 GGGGGGCAGG CACCGCGTAT CAGAGGAGCA GTGGCCTCAC ACCTGGGGCC
1601 CCTTTCCACC CTATGCCTCA GGCACGGGGT ATGTGCTGTC AGCGTCTGCT
1651 GTGCAGCTCA TTCTCAAGGT GGCCAGCCGG GCACCCCTTC TCCCATTAGA
1701 GGATGTCTTT GTGGGGGTAA GTGCCCGACG AGGAGGCCTC GCCCCAACAC
1751 AGTGTGTCAA GCTGGCTGGT GCCACCCACT ACCCGCTAGA CCGGTGCTGC
1801 TATGGGAAAT TCCTGCTGAC GTCCCACAGG CTGGACCCCT GGAAGATGCA
1851 GGAAGCCTGG AAGCTGGTGG GTGGCTCTGA CGGGGAAAGG ACTGCGCCCT
1901 TTTGCTCCTG GTTCCAGGGA GTCCTGGGCA TCCTGCGGTG TCGAGCAATA
1951 GCCTGGCTTC AGAGCTGAGG ATCCACCGGA TCTAGATAAC TGATCATAAT
```

-continued

2001 CAGCCATACC ACATTTGTAG AGGTTTTACT TGCTTTAAAA AACCTCCCAC
2051 ACCTCCCCCT GAACCTGAAA CATAAAATGA ATGCAATTGT TGTTGTTAAC
2101 TTGTTTATTG CAGCTTATAA TGGTTACAAA TAAAGCAATA GCATCACAAA
2151 TTTCACAAAT AAAGCATTTT TTTCACTGCA TTCTAGTTGT GGTTTGTCCA
2201 AACTCATCAA TGTATCTTAA CGCCCTTCCC AACAGTTGCG CAGCCTGAAT
2251 GGCGAATGGA CGCGCCCTGT AGCGGACTAG TAGTATCTGC AGAGGGCCCT
2301 GCGTATGAGT GCAAGTGGGT TTTAGGACCA GGATGAGGCG GGGTGGGGGT
2351 GCCTACCTGA CGACCGACCC CGACCCACTG GACAAGCACC CAACCCCCAT
2401 TCCCCAAATT GCGCATCCCC TATCAGAGAG GGGGAGGGGA AACAGGATGC
2451 GGCGAGGCGC GTGCGCACTG CCAGCTTCAG CACCGCGGAC AGTGCCTTCG
2501 CCCCCGCCTG GCGGCGCGCG CCACCGCCGC CTCAGCACTG AAGGCGCGCT
2551 GACGTCACTC GCCGGTCCCC CGCAAACTCC CCTTCCCGGC CACCTTGGTC
2601 GCGTCCGCGC CGCCGCCGGC CCAGCCGGAC CGCACCACGC GAGGCGCGAG
2651 ATAGGGGGGC ACGGGCGCGA CCATCTGCGC TGCGGCGCCG GCGACTCAGC
2701 GCTGCCTCAG TCTGCGGTGG GCAGCGGAGG AGTCGTGTCG TGCCTGAGAG
2751 CGCAGCTGTG CTCCTGGGCA CCGCGCAGTC CGCCCCCGCG GCTCCTGGCC
2801 AGACCACCCC TAGGACCCCC TGCCCCAAGT CGCAGCCAAG CTTAGAATTG
2851 GAGCTTGCTT CTATAGATCC ACCGGTCGCC ACCATGGTGA GCAAGGGCGA
2901 GGAGCTGTTC ACCGGGGTGG TGCCCATCCT GGTCGAGCTG GACGGCGACG
2951 TAAACGGCCA CAAGTTCAGC GTGTCCGGCG AGGGCGAGGG CGATGCCACC
3001 TACGGCAAGC TGACCCTGAA GTTCATCTGC ACCACCGGCA AGCTGCCCGT
3051 GCCCTGGCCC ACCCTCGTGA CCACCCTGAC CTACGGCGTG CAGTGCTTCA
3101 GCCGCTACCC CGACCACATG AAGCAGCACG ACTTCTTCAA GTCCGCCATG
3151 CCCGAAGGCT ACGTCCAGGA GCGCACCATC TTCTTCAAGG ACGACGGCAA
3201 CTACAAGACC CGCGCCGAGG TGAAGTTCGA GGGCGACACC CTGGTGAACC
3251 GCATCGAGCT GAAGGGCATC GACTTCAAGG AGGACGGCAA CATCCTGGGG
3301 CACAAGCTGG AGTACAACTA CAACAGCCAC AACGTCTATA TCATGGCCGA
3351 CAAGCAGAAG AACGGCATCA AGGTGAACTT CAAGATCCGC CACAACATCG
3401 AGGACGGCAG CGTGCAGCTC GCCGACCACT ACCAGCAGAA CACCCCCATC
3451 GGCGACGGCC CCGTGCTGCT GCCCGACAAC CACTACCTGA GCACCCAGTC
3501 CGCCCTGAGC AAAGACCCCA ACGAGAAGCG CGATCACATG GTCCTGCTGG
3551 AGTTCGTGAC CGCCGCCGGG ATCACTCTCG GCATGGACGA GCTGTACAAG
3601 TAAAGCGGCC GCTCGAGTCT AGAGGGCCCT TCGAAGGTAA GCCTATCCCT
3651 AACCCTCTCC TCGGTCTCGA TTCTACGCGT ACCGGTCATC ATCACCATCA
3701 CCATTGAGTT TAAACCCGCT GATCAGCCTC GACTGTGCCT TCTAGTTGCC
3751 AGCCATCTGT TGTTTGCCCC TCCCCCGTGC CTTCCTTGAC CCTGGAAGGT
3801 GCCACTCCCA CTGTCCTTTC CTAATAAAAT GAGGAAATTG CATCGCATTG
3851 TCTGAGTAGG TGTCATTCTA TTCTGGGGGG TGGGGTGGGG CAGGACAGCA
3901 AGGGGGAGGA TTGGGAAGAC AATAGCAGGC ATGCTGGGGA TGCGGTGGGC
3951 TCTATGGCTT CTGAGGCGGA AAGAACCAGA TCCTCTCTTA AGGTAGCATC

-continued

4001 GAGATTTAAA TTAGGGATAA CAGGGTAATG GCGCGGGCCG CAGGAACCCC

4051 TAGTGATGGA GTTGGCCACT CCCTCTCTGC GCGCTCGCTC GCTCACTGAG

4101 GCCGGGCGAC CAAAGGTCGC CCGACGCCCG GGCTTTGCCC GGGCGGCCTC

4151 AGTGAGCGAG CGAGCGCGCA GCTGCCTGCA GGGGCGCCTG ATGCGGTATT

4201 TTCTCCTTAC GCATCTGTGC GGTATTTCAC ACCGCATACG TCAAAGCAAC

4251 CATAGTACGC GCCCTGTAGC GGCGCATTAA GCGCGGCGGG TGTGGTGGTT

4301 ACGCGCAGCG TGACCGCTAC ACTTGCCAGC GCCCTAGCGC CCGCTCCTTT

4351 CGCTTTCTTC CCTTCCTTTC TCGCCACGTT CGCCGGCTTT CCCCGTCAAG

4401 CTCTAAATCG GGGGCTCCCT TTAGGGTTCC GATTTAGTGC TTTACGGCAC

4451 CTCGACCCCA AAAAACTTGA TTTGGGTGAT GGTTCACGTA GTGGGCCATC

4501 GCCCTGATAG ACGGTTTTTC GCCCTTTGAC GTTGGAGTCC ACGTTCTTTA

4551 ATAGTGGACT CTTGTTCCAA ACTGGAACAA CACTCAACCC TATCTCGGGC

4601 TATTCTTTTG ATTTATAAGG GATTTTGCCG ATTTCGGCCT ATTGGTTAAA

4651 AAATGAGCTG ATTTAACAAA AATTTAACGC GAATTTTAAC AAAATATTAA

4701 CGTTTACAAT TTTATGGTGC ACTCTCAGTA CAATCTGCTC TGATGCCGCA

4751 TAGTTAAGCC AGCCCCGACA CCCGCCAACA CCCGCTGACG CGCCCTGACG

4801 GGCTTGTCTG CTCCCGGCAT CCGCTTACAG ACAAGCTGTG ACCGTCTCCG

4851 GGAGCTGCAT GTGTCAGAGG TTTTCACCGT CATCACCGAA ACGCGCGAGA

4901 CGAAAGGGCC TCGTGATACG CCTATTTTTA TAGGTTAATG TCATGATAAT

4951 AATGGTTTCT TAGACGTCAG GTGGCACTTT TCGGGGAAAT GTGCGCGGAA

5001 CCCCTATTTG TTTATTTTTC TAAATACATT CAAATATGTA TCCGCTCATG

5051 AGACAATAAC CCTGATAAAT GCTTCAATAA TATTGAAAAA GGAAGAGTAT

5101 GAGTATTCAA CATTTCCGTG TCGCCCTTAT TCCCTTTTTT GCGGCATTTT

5151 GCCTTCCTGT TTTTGCTCAC CCAGAAACGC TGGTGAAAGT AAAAGATGCT

5201 GAAGATCAGT TGGGTGCACG AGTGGGTTAC ATCGAACTGG ATCTCAACAG

5251 CGGTAAGATC CTTGAGAGTT TTCGCCCCGA AGAACGTTTT CCAATGATGA

5301 GCACTTTTAA AGTTCTGCTA TGTGGCGCGG TATTATCCCG TATTGACGCC

5351 GGGCAAGAGC AACTCGGTCG CCGCATACAC TATTCTCAGA ATGACTTGGT

5401 TGAGTACTCA CCAGTCACAG AAAAGCATCT TACGGATGGC ATGACAGTAA

5451 GAGAATTATG CAGTGCTGCC ATAACCATGA GTGATAACAC TGCGGCCAAC

5501 TTACTTCTGA CAACGATCGG AGGACCGAAG GAGCTAACCG CTTTTTTGCA

5551 CAACATGGGG GATCATGTAA CTCGCCTTGA TCGTTGGGAA CCGGAGCTGA

5601 ATGAAGCCAT ACCAAACGAC GAGCGTGACA CCACGATGCC TGTAGCAATG

5651 GCAACAACGT TGCGCAAACT ATTAACTGGC GAACTACTTA CTCTAGCTTC

5701 CCGGCAACAA TTAATAGACT GGATGGAGGC GGATAAAGTT GCAGGACCAC

5751 TTCTGCGCTC GGCCCTTCCG GCTGGCTGGT TTATTGCTGA TAAATCTGGA

5801 GCCGGTGAGC GTGGGTCTCG CGGTATCATT GCAGCACTGG GGCCAGATGG

5851 TAAGCCCTCC CGTATCGTAG TTATCTACAC GACGGGGAGT CAGGCAACTA

5901 TGGATGAACG AAATAGACAG ATCGCTGAGA TAGGTGCCTC ACTGATTAAG

5951 CATTGGTAAC TGTCAGACCA AGTTTACTCA TATATACTTT AGATTGATTT

6001 AAAACTTCAT TTTTAATTTA AAAGGATCTA GGTGAAGATC CTTTTTGATA

-continued

6051 ATCTCATGAC CAAAATCCCT TAACGTGAGT TTTCGTTCCA CTGAGCGTCA

6101 GACCCCGTAG AAAAGATCAA AGGATCTTCT TGAGATCCTT TTTTTCTGCG

6151 CGTAATCTGC TGCTTGCAAA CAAAAAAACC ACCGCTACCA GCGGTGGTTT

6201 GTTTGCCGGA TCAAGAGCTA CCAACTCTTT TTCCGAAGGT AACTGGCTTC

6251 AGCAGAGCGC AGATACCAAA TACTGTCCTT CTAGTGTAGC CGTAGTTAGG

6301 CCACCACTTC AAGAACTCTG TAGCACCGCC TACATACCTC GCTCTGCTAA

6351 TCCTGTTACC AGTGGCTGCT GCCAGTGGCG ATAAGTCGTG TCTTACCGGG

6401 TTGGACTCAA GACGATAGTT ACCGGATAAG GCGCAGCGGT CGGGCTGAAC

6451 GGGGGGTTCG TGCACACAGC CCAGCTTGGA GCGAACGACC TACACCGAAC

6501 TGAGATACCT ACAGCGTGAG CTATGAGAAA GCGCCACGCT TCCCGAAGGG

6551 AGAAAGGCGG ACAGGTATCC GGTAAGCGGC AGGGTCGGAA CAGGAGAGCG

6601 CACGAGGGAG CTTCCAGGGG GAAACGCCTG GTATCTTTAT AGTCCTGTCG

6651 GGTTTCGCCA CCTCTGACTT GAGCGTCGAT TTTTGTGATG CTCGTCAGGG

6701 GGGCGGAGCC TATGGAAAAA CGCCAGCAAC GCGGCCTTTT TACGGTTCCT

6751 GGCCTTTTGC TGGCCTTTTG CTCACATGT

Annotation of AAV-Syn-hB3GATL4-SynEGFP (SEQ ID NO: 1): Left inverted terminal repeat 1-141, Synapsin promoter-I: 262-817, hB3gALT4: 832-1968, SV40 poly(A): 1993-2221, Synapsin promoter-II: 2282-2837, EGFP CDS: 2884-3601, BGH polyadenylation sequence: 3730-3957, right inverted terminal repeat 4042-4182, ampicillin resistance (bla) ORF 5099-5956, pUC origin 6107-6774.

AAV-Syn-hNEU3-SynEGFP (SEQ ID NO: 2)

1 CCTGCAGGCA GCTGCGCGCT CGCTCGCTCA CTGAGGCCGC CCGGGCAAAG

51 CCCGGGCGTC GGGCGACCTT TGGTCGCCCG GCCTCAGTGA GCGAGCGAGC

101 GCGCAGAGAG GGAGTGGCCA ACTCCATCAC TAGGGGTTCC TGCGGCCAAT

151 TCAGTCGATA ACTATAACGG TCCTAAGGTA GCGATTTAAA TACGCGCTCT

201 CTTAAGGTAG CCCCGGGACG CGTCAATTCG CGCCTGAGTT GAATATCAAC

251 ACTACAAACC GAGTATCTGC AGAGGGCCCT GCGTATGAGT GCAAGTGGGT

301 TTTAGGACCA GGATGAGGCG GGGTGGGGGT GCCTACCTGA CGACCGACCC

351 CGACCCACTG GACAAGCACC CAACCCCCAT TCCCCAAATT GCGCATCCCC

401 TATCAGAGAG GGGGAGGGGA AACAGGATGC GGCGAGGCGC GTGCGCACTG

451 CCAGCTTCAG CACCGCGGAC AGTGCCTTCG CCCCCGCCTG GCGGCGCGCG

501 CCACCGCCGC CTCAGCACTG AAGGCGCGCT GACGTCACTC GCCGGTCCCC

551 CGCAAACTCC CCTTCCCGGC CACCTTGGTC GCGTCCGCGC CGCCGCCGGC

601 CCAGCCGGAC CGCACCACGC GAGGCGCGAG ATAGGGGGGC ACGGGCGCGA

651 CCATCTGCGC TGCGGCGCCG GCGACTCAGC GCTGCCTCAG TCTGCGGTGG

701 GCAGCGGAGG AGTCGTGTCG TGCCTGAGAG CGCAGCTGTG CTCCTGGGCA

751 CCGCGCAGTC CGCCCCCGCG GCTCCTGGCC AGACCACCCC TAGGACCCCC

801 TGCCCCAAGT CGCAGCCTTC GAATTCGCCC TTCCCACGTA GGCCTTCCAA

851 AGCGCTGAGA TTGTAGGCAT AAGCCACCAG GCCCAGCCTA TTACCTTTAC

-continued

```
 901 GTTGTACTTA GTCCCAGATA AAAAATGACC TTAGATCAGT CCTTTCCTCT
 951 TTGGCTGGGG AGAGGGGGGC TTAAATTCCG GTACTGTGAA ACAGAAGAAT
1001 GGACTCAGTG CTATGTGACA AATCTATGTA TGTAAATGTG TGTATATACA
1051 CACACATAAA TTATATATAT GAATATATTT TCATTTTCAT ATTTTGCAAG
1101 GAGAGTAGCC AATGCTCTGG ACCTCTGGTC CTTTTTGTAG GGTACCCTCT
1151 GAGGCCGGGA ACCTTTGCTC AACTCTCAGG CTGTCCAGGG AAGCTTTAGG
1201 CGGTGATACC GAGCTACAGA CCAATATAAG AGCTCGGGGC TGTGGCACTG
1251 AAGAGAGGAG GCGGCCGTTG GGAACTGAGT CTCCCCAGCC TTGGGGCCGG
1301 TGCCTCTTCC GGGCTTCGGC GAATGAGACC TGCGGACCTG CCCCCGCGCC
1351 CCATGGAAGA ATCCCCGGCG TCCAGCTCTG CCCCGACAGA GACGGAGGAG
1401 CCGGGGTCCA GTGCAGAGGT CATGGAAGAA GTGACAACAT GCTCCTTCAA
1451 CAGCCCTCTG TTCCGGCAGG AAGATGACAG AGGGATTACC TACCGGATCC
1501 CAGCCCTGCT CTACATACCC CCCACCCACA CCTTCCTGGC CTTTGCAGAG
1551 AAGCGTTCTA CGAGGAGAGA TGAGGATGCT CTCCACCTGG TGCTGAGGCG
1601 AGGGTTGAGG ATTGGGCAGT TGGTACAGTG GGGGCCCCTG AAGCCACTGA
1651 TGGAAGCCAC ACTACCGGGG CATCGGACCA TGAACCCCTG TCCTGTATGG
1701 GAGCAGAAGA GTGGTTGTGT GTTCCTGTTC TTCATCTGTG TGCGGGGCCA
1751 TGTCACAGAG CGTCAACAGA TTGTGTCAGG CAGGAATGCT GCCCGCCTTT
1801 GCTTCATCTA CAGTCAGGAT GCTGGATGTT CATGGAGTGA GGTGAGGGAC
1851 TTGACTGAGG AGGTCATTGG CTCAGAGCTG AAGCACTGGG CCACATTTGC
1901 TGTGGGCCCA GGTCATGGCA TCCAGCTGCA GTCAGGGAGA CTGGTCATCC
1951 CTGCGTATAC CTACTACATC CCTTCCTGGT TCTTTTGCTT CCAGCTACCA
2001 TGTAAAACCA GGCCTCATTC TCTGATGATC TACAGTGATG ACCTAGGGGT
2051 CACATGGCAC CATGGTAGAC TCATTAGGCC CATGGTTACA GTAGAATGTG
2101 AAGTGGCAGA GGTGACTGGG AGGGCTGGCC ACCCTGTGCT ATATTGCAGT
2151 GCCCGGACAC CAAACAGGTG CCGGGCAGAG GCGCTCAGCA CTGACCATGG
2201 TGAAGGCTTT CAGAGACTGG CCCTGAGTCG ACAGCTCTGT GAGCCCCCAC
2251 ATGGTTGCCA AGGGAGTGTG GTAAGTTTCC GGCCCCTGGA GATCCCACAT
2301 AGGTGCCAGG ACTCTAGCAG CAAAGATGCA CCCACCATTC AGCAGAGCTC
2351 TCCAGGCAGT TCACTGAGGC TGGAGGAGGA AGCTGGAACA CCGTCAGAAT
2401 CATGGCTCTT GTACTCACAC CCAACCAGTA GGAAACAGAG GGTTGACCTA
2451 GGTATCTATC TCAACCAGAC CCCCTTGGAG GCTGCCTGCT GGTCCCGCCC
2501 CTGGATCTTG CACTGTGGGC CCTGTGGCTA CTCTGATCTG GCTGCTCTGG
2551 AGGAGGAGGG CTTGTTTGGG TGTTTGTTTG AATGTGGGAC CAAGCAAGAG
2601 TGTGAGCAGA TTGCCTTCCG CCTGTTTACA CACCGGGAGA TCCTGAGTCA
2651 CCTGCAGGGG GACTGCACCA GCCCTGGTAG GAACCCAAGC CAATTCAAAA
2701 GCAATTAATT GGCTTAGGAC CCAATTTCCA TAGATGCAAA TGGCAGTTAC
2751 AGACAGGTTA ACAGAAGCTA CTGAAGTCTA CAGATAATCA AAAAACTTAA
2801 TATTCTGTTC CCTACCTTTT TTCACTTTTC CTCCTCCAAA GAGCAAAATG
2851 AAAATTTTGC CTTAGCTACT GCAGTGGAAA GAGCACTGAA CTAGGAGTTG
2901 GAAGACAAGG ATGTGGTCCT GGCTCTGCCA CTGGCTTGCT TTTGGACCTT
```

-continued

2951 GGATGTGTCA CCTGAACTCT CTGGACCTCA GGTTTCCATC TGTAAAATGA

3001 GAGTATTGGT TCTAAGATTT CTCATCTTCT CATCCCTAGG ACAAGCATAG

3051 TGCCTGCATG CTTCATGATC AGTAAGTCCT GGCTGCATAA AGGACTCTGA

3101 TGTCAAAATG GAAACCAGGG GACTTACCTT TTCACATGAC TTACCCCTCA

3151 TCCGAGTGTG AGGTTACAAG CAGGTGTCAT GGCAGGAAGG GCTGCCCCAA

3201 GGGCGAATTC TGCAGTCGAC GGTACCGCGG GCCCGGGATC CACCGGATCT

3251 AGATAACTGA TCATAATCAG CCATACCACA TTTGTAGAGG TTTTACTTGC

3301 TTTAAAAAAC CTCCCACACC TCCCCCTGAA CCTGAAACAT AAAATGAATG

3351 CAATTGTTGT TGTTAACTTG TTTATTGCAG CTTATAATGG TTACAAATAA

3401 AGCAATAGCA TCACAAATTT CACAAATAAA GCATTTTTTT CACTGCATTC

3451 TAGTTGTGGT TTGTCCAAAC TCATCAATGT ATCTTAACGC CCTTCCCAAC

3501 AGTTGCGCAG CCTGAATGGC GAATGGACGC GCCCTGTAGC GGACTAGTAG

3551 TATCTGCAGA GGGCCCTGCG TATGAGTGCA AGTGGGTTTT AGGACCAGGA

3601 TGAGGCGGGG TGGGGGTGCC TACCTGACGA CCGACCCCGA CCCACTGGAC

3651 AAGCACCCAA CCCCCATTCC CCAAATTGCG CATCCCCTAT CAGAGAGGGG

3701 GAGGGGAAAC AGGATGCGGC GAGGCGCGTG CGCACTGCCA GCTTCAGCAC

3751 CGCGGACAGT GCCTTCGCCC CCGCCTGGCG GCGCGCGCCA CCGCCGCCTC

3801 AGCACTGAAG GCGCGCTGAC GTCACTCGCC GGTCCCCCGC AAACTCCCCT

3851 TCCCGGCCAC CTTGGTCGCG TCCGCGCCGC CGCCGGCCCA GCCGGACCGC

3901 ACCACGCGAG GCGCGAGATA GGGGGGCACG GGCGCGACCA TCTGCGCTGC

3951 GGCGCCGGCG ACTCAGCGCT GCCTCAGTCT GCGGTGGGCA GCGGAGGAGT

4001 CGTGTCGTGC CTGAGAGCGC AGCTGTGCTC CTGGGCACCG CGCAGTCCGC

4051 CCCCGCGGCT CCTGGCCAGA CCACCCCTAG GACCCCCTGC CCCAAGTCGC

4101 AGCCAAGCTT AGAATTGGAG CTTGCTTCTA TAGATCCACC GGTCGCCACC

4151 ATGGTGAGCA AGGGCGAGGA GCTGTTCACC GGGGTGGTGC CCATCCTGGT

4201 CGAGCTGGAC GGCGACGTAA ACGGCCACAA GTTCAGCGTG TCCGGCGAGG

4251 GCGAGGGCGA TGCCACCTAC GGCAAGCTGA CCCTGAAGTT CATCTGCACC

4301 ACCGGCAAGC TGCCCGTGCC CTGGCCCACC CTCGTGACCA CCCTGACCTA

4351 CGGCGTGCAG TGCTTCAGCC GCTACCCCGA CCACATGAAG CAGCACGACT

4401 TCTTCAAGTC CGCCATGCCC GAAGGCTACG TCCAGGAGCG CACCATCTTC

4451 TTCAAGGACG ACGGCAACTA CAAGACCCGC GCCGAGGTGA AGTTCGAGGG

4501 CGACACCCTG GTGAACCGCA TCGAGCTGAA GGGCATCGAC TTCAAGGAGG

4551 ACGGCAACAT CCTGGGGCAC AAGCTGGAGT ACAACTACAA CAGCCACAAC

4601 GTCTATATCA TGGCCGACAA GCAGAAGAAC GGCATCAAGG TGAACTTCAA

4651 GATCCGCCAC AACATCGAGG ACGGCAGCGT GCAGCTCGCC GACCACTACC

4701 AGCAGAACAC CCCCATCGGC GACGGCCCCG TGCTGCTGCC CGACAACCAC

4751 TACCTGAGCA CCCAGTCCGC CCTGAGCAAA GACCCCAACG AGAAGCGCGA

4801 TCACATGGTC CTGCTGGAGT TCGTGACCGC CGCCGGGATC ACTCTCGGCA

4851 TGGACGAGCT GTACAAGTAA AGCGGCCGCT CGAGTCTAGA GGGCCCTTCG

4901 AAGGTAAGCC TATCCCTAAC CCTCTCCTCG GTCTCGATTC TACGCGTACC

-continued

```
4951 GGTCATCATC ACCATCACCA TTGAGTTTAA ACCCGCTGAT CAGCCTCGAC
5001 TGTGCCTTCT AGTTGCCAGC CATCTGTTGT TTGCCCCTCC CCCGTGCCTT
5051 CCTTGACCCT GGAAGGTGCC ACTCCCACTG TCCTTTCCTA ATAAAATGAG
5101 GAAATTGCAT CGCATTGTCT GAGTAGGTGT CATTCTATTC TGGGGGGTGG
5151 GGTGGGGCAG GACAGCAAGG GGGAGGATTG GGAAGACAAT AGCAGGCATG
5201 CTGGGGATGC GGTGGGCTCT ATGGCTTCTG AGGCGGAAAG AACCAGATCC
5251 TCTCTTAAGG TAGCATCGAG ATTTAAATTA GGGATAACAG GGTAATGGCG
5301 CGGGCCGCAG GAACCCCTAG TGATGGAGTT GGCCACTCCC TCTCTGCGCG
5351 CTCGCTCGCT CACTGAGGCC GGGCGACCAA AGGTCGCCCG ACGCCCGGGC
5401 TTTGCCCGGG CGGCCTCAGT GAGCGAGCGA GCGCGCAGCT GCCTGCAGGG
5451 GCGCCTGATG CGGTATTTTC TCCTTACGCA TCTGTGCGGT ATTTCACACC
5501 GCATACGTCA AAGCAACCAT AGTACGCGCC CTGTAGCGGC GCATTAAGCG
5551 CGGCGGGTGT GGTGGTTACG CGCAGCGTGA CCGCTACACT TGCCAGCGCC
5601 CTAGCGCCCG CTCCTTTCGC TTTCTTCCCT TCCTTTCTCG CCACGTTCGC
5651 CGGCTTTCCC CGTCAAGCTC TAAATCGGGG GCTCCCTTTA GGGTTCCGAT
5701 TTAGTGCTTT ACGGCACCTC GACCCCAAAA AACTTGATTT GGGTGATGGT
5751 TCACGTAGTG GGCCATCGCC CTGATAGACG GTTTTTCGCC CTTTGACGTT
5801 GGAGTCCACG TTCTTTAATA GTGGACTCTT GTTCCAAACT GGAACAACAC
5851 TCAACCCTAT CTCGGGCTAT TCTTTTGATT TATAAGGGAT TTTGCCGATT
5901 TCGGCCTATT GGTTAAAAAA TGAGCTGATT TAACAAAAAT TTAACGCGAA
5951 TTTTAACAAA ATATTAACGT TTACAATTTT ATGGTGCACT CTCAGTACAA
6001 TCTGCTCTGA TGCCGCATAG TTAAGCCAGC CCCGACACCC GCCAACACCC
6051 GCTGACGCGC CCTGACGGGC TTGTCTGCTC CCGGCATCCG CTTACAGACA
6101 AGCTGTGACC GTCTCCGGGA GCTGCATGTG TCAGAGGTTT TCACCGTCAT
6151 CACCGAAACG CGCGAGACGA AAGGGCCTCG TGATACGCCT ATTTTTATAG
6201 GTTAATGTCA TGATAATAAT GGTTTCTTAG ACGTCAGGTG GCACTTTTCG
6251 GGGAAATGTG CGCGGAACCC CTATTTGTTT ATTTTTCTAA ATACATTCAA
6301 ATATGTATCC GCTCATGAGA CAATAACCCT GATAAATGCT TCAATAATAT
6351 TGAAAAAGGA AGAGTATGAG TATTCAACAT TTCCGTGTCG CCCTTATTCC
6401 CTTTTTTGCG GCATTTTGCC TTCCTGTTTT TGCTCACCCA GAAACGCTGG
6451 TGAAAGTAAA AGATGCTGAA GATCAGTTGG GTGCACGAGT GGGTTACATC
6501 GAACTGGATC TCAACAGCGG TAAGATCCTT GAGAGTTTTC GCCCCGAAGA
6551 ACGTTTTCCA ATGATGAGCA CTTTTAAAGT TCTGCTATGT GGCGCGGTAT
6601 TATCCCGTAT TGACGCCGGG CAAGAGCAAC TCGGTCGCCG CATACACTAT
6651 TCTCAGAATG ACTTGGTTGA GTACTCACCA GTCACAGAAA AGCATCTTAC
6701 GGATGGCATG ACAGTAAGAG AATTATGCAG TGCTGCCATA ACCATGAGTG
6751 ATAACACTGC GGCCAACTTA CTTCTGACAA CGATCGGAGG ACCGAAGGAG
6801 CTAACCGCTT TTTTGCACAA CATGGGGGAT CATGTAACTC GCCTTGATCG
6851 TTGGGAACCG GAGCTGAATG AAGCCATACC AAACGACGAG CGTGACACCA
6901 CGATGCCTGT AGCAATGGCA ACAACGTTGC GCAAACTATT AACTGGCGAA
6951 CTACTTACTC TAGCTTCCCG GCAACAATTA ATAGACTGGA TGGAGGCGGA
```

-continued

```
7001 TAAAGTTGCA GGACCACTTC TGCGCTCGGC CCTTCCGGCT GGCTGGTTTA
7051 TTGCTGATAA ATCTGGAGCC GGTGAGCGTG GGTCTCGCGG TATCATTGCA
7101 GCACTGGGGC CAGATGGTAA GCCCTCCCGT ATCGTAGTTA TCTACACGAC
7151 GGGGAGTCAG GCAACTATGG ATGAACGAAA TAGACAGATC GCTGAGATAG
7201 GTGCCTCACT GATTAAGCAT TGGTAACTGT CAGACCAAGT TTACTCATAT
7251 ATACTTTAGA TTGATTTAAA ACTTCATTTT TAATTTAAAA GGATCTAGGT
7301 GAAGATCCTT TTTGATAATC TCATGACCAA AATCCCTTAA CGTGAGTTTT
7351 CGTTCCACTG AGCGTCAGAC CCCGTAGAAA AGATCAAAGG ATCTTCTTGA
7401 GATCCTTTTT TTCTGCGCGT AATCTGCTGC TTGCAAACAA AAAAACCACC
7451 GCTACCAGCG GTGGTTTGTT TGCCGGATCA AGAGCTACCA ACTCTTTTTC
7501 CGAAGGTAAC TGGCTTCAGC AGAGCGCAGA TACCAAATAC TGTCCTTCTA
7551 GTGTAGCCGT AGTTAGGCCA CCACTTCAAG AACTCTGTAG CACCGCCTAC
7601 ATACCTCGCT CTGCTAATCC TGTTACCAGT GGCTGCTGCC AGTGGCGATA
7651 AGTCGTGTCT TACCGGGTTG GACTCAAGAC GATAGTTACC GGATAAGGCG
7701 CAGCGGTCGG GCTGAACGGG GGGTTCGTGC ACACAGCCCA GCTTGGAGCG
7751 AACGACCTAC ACCGAACTGA GATACCTACA GCGTGAGCTA TGAGAAAGCG
7801 CCACGCTTCC CGAAGGGAGA AAGGCGGACA GGTATCCGGT AAGCGGCAGG
7851 GTCGGAACAG GAGAGCGCAC GAGGGAGCTT CCAGGGGGAA ACGCCTGGTA
7901 TCTTTATAGT CCTGTCGGGT TTCGCCACCT CTGACTTGAG CGTCGATTTT
7951 TGTGATGCTC GTCAGGGGGG CGGAGCCTAT GGAAAAACGC CAGCAACGCG
8001 GCCTTTTTAC GGTTCCTGGC CTTTTGCTGG CCTTTTGCTC ACATGT
```

Annotation of AAV-Syn-hNEU3-SynEGFP (SEQ ID NO: 2): left inverted terminal repeat: 1-141, Synapsin promoter-I: 262-817, hNEU3: 833-3190, SV40 poly(A): 3260-3488, Synapsin promoter-II: 3549-4104, EGFP CDS: 4151-4868, BGH polyadenylation sequence: 4997-5224, right inverted terminal repeat 5309-5449, ampicillin resistance (bla) ORF 6366-7223, pUC origin 7374-8041.

Pharmaceutical Compositions and Formulations

Also provided are compositions comprising GM1 or a derivative thereof. Among the compositions are pharmaceutical compositions and formulations for administration, such as for treatments of synucleinopathies including but not limited to Lewy body dementia, multi-system atrophy, or pure autonomic failure, inherited forms of Parkinson's disease with synuclein gene mutations, lysosomal storage disorders associated with abnormal alpha synuclein deposits in the brain (including disorders such as Sanfilippo syndrome and related Mucopolysaccaridoses), GlcCerase (GBA) mutations accompanied by abnormal synuclein accumulation in a subject (e.g patient) in need thereof. The GM1 can be derived from any source known to one of ordinary skill in the art including but not limited to animal-derived (e.g. pig, cow, sheep, human, etc.) or synthetically derived (e.g. man-made, synthesized, engineered, conjugated etc.). In certain embodiments, the GM1 is derived from an animal brain. The GM1 can be the entire GM1 molecule including the oligosaccharide portion and the lipid moiety or the GM1 oligosaccharide portion alone.

The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered. A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. In some aspects, the choice of carrier is determined in part by the particular composition and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated, preferably those with activities complementary to the composition, where the respective activities do not adversely affect one another. Such active ingredients are suitably present in combination in amounts that are effective for the purpose intended. Thus, in some embodiments, the pharmaceutical composition further includes other pharmaceutically active agents or drugs. The pharmaceutical composition in some embodiments contains amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the composition, by multiple bolus administrations of the composition, or by continuous infusion administration of the composition.

Formulations include those for oral, intravenous, intraperitoneal, subcutaneous, pulmonary, transdermal, intramuscular, intranasal, buccal, sublingual, or suppository administration. In some embodiments, the composition are administered parenterally. The term "parenteral," as used herein, includes intravenous, intramuscular, subcutaneous, rectal, vaginal, and intraperitoneal administration. In some embodiments, the composition is administered to the subject using peripheral systemic delivery by intravenous, intraperitoneal, or subcutaneous injection. Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

GM1 or derivatives can be administered as nanoparticle formulations or in exosomes. Nanoparticles include but are not limited to liposomes, pegylated liposomes, functionalized polymersomes, polymeric microspheres, or nanomicelles. Nanoparticles can be ones that target brain in general or target and deliver GM1 or derivatives at specific sites in the brain. Naturally occurring or manufactured exosomes can be used as delivery vehicles for GM1 ganglioside or derivatives for delivery to brain, preferably via an intranasal delivery route or oral delivery route. Exosomes may be functionalized to target specific cell types in the brain.

Sterile injectable solutions can be prepared by incorporating the composition in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

Experimental Examples

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Methods

Vector

Full details of AAV-A53T alpha synuclein vector design can be found in Koprich et al. Mol Neurodegener 5:43 (2010). Briefly, a chimeric adeno-associated vector (AAV) of a 1/2 serotype (capsid expresses AAV1 and AAV2 serotype proteins in a 1:1 ratio) with human A53T alpha synuclein expression driven by a chicken beta actin (CBA) promoter hybridized with the cytomegalovirus (CMV) immediate early enhancer sequence was used. A woodchuck post-transcriptional regulatory element (WPRE) and a bovine growth hormone polyadenylation sequence (bGH-polyA) were also incorporated to further enhance transcription following transduction. The vectors (AAV1/2-A53T and empty vector control) were produced by GeneDetect Ltd., Auckland, New Zealand. Viral titers were determined by quantitative PCR (Applied Biosystems 7900 QPCR) with primers directed to the WPRE region, thus representing the number of functional physical particles of AAV in the solution containing the genome to be delivered.

Animals and Vector Delivery

All animal procedures were approved by the Thomas Jefferson University Institutional Animal Care and Use Committee and conducted in accordance with the National Institutes of Health Guide for the Care and Use of Laboratory Animals. Adult male Sprague-Dawley rats (Envigo), 250 to 300 g at the time of surgery, were housed three per cage with ad libitum access to food and water during a 12-hour light/dark cycle. All surgeries were performed under general anesthesia using a mixture of ketamine (100 mg/kg, i.p.) and xylazine (10 mg/kg, i.p.). Once animals were anesthetized, the head was shaved and surgically prepped with Betadine solution and alcohol before being placed in a Kopf stereotaxic frame with the incisor bar set at approximately 3.5 mm below horizontal zero to achieve a flat skull position. The skin on the top of the skull was cut along the midline and retracted. Using coordinates AP: −5.3, L: 2.2, D: 7.5 below skull, derived from bregma, a small burr hole was created over the SN on one side and a 36 gauge needle attached to a Hamilton syringe loaded with AAV-A53T-synuclein or empty vector control virus was slowly lowered into the brain and 2.0 μl was injected above the SN at a rate of 0.2 μl/min using a motorized syringe pump. Following a 5 minute wait period after completion of the injection, the needle was slowly withdrawn, the skin wound was closed, and post-surgery analgesia (meloxicam 1 mg/kg) was administered. Some rats were randomly assigned to receive daily GM1 ganglioside (porcine brain derived GM1, 30 mg/kg, i.p., Qilu Pharmaceutical Co., Ltd.) or similar volume saline injections beginning 24 hours after AAV-A53T-synuclein surgery and lasting for 6 weeks (early start group). Other animals were randomly assigned to receive daily GM1 ganglioside (porcine brain derived GM1, 30 mg/kg, i.p., Qilu Pharmaceutical Co.) or similar volume saline injections beginning 3 weeks after AAV-A53T-synuclein surgery and lasting for 5 weeks (delayed start group). The dose of 30 mg/kg was selected based on the following information: this dose of GM1 was previously found to be effective in MPTP lesion models in mice; this dose was shown to be effective in stimulating regenerative responses in numerous rodent studies spanning a variety of central and peripheral lesion models. At the conclusion of the study, animals were euthanized, fresh brains were rapidly removed, and two to three striatal samples from both sides were dissected and immediately frozen for later analyses. The remainder of the brain (including the striatum beginning at the level of the decussation of the anterior commissure) was submersion fixed in 4% paraformaldehyde.

Behavioral Testing

Forelimb use during explorative activity was analyzed using the cylinder test. The test apparatus consisted of a clear Plexiglass cylinder of approximately 33 cm diameter and 50 cm height placed in a dimly lit room in front of a mirror in order to visualize limb use from all angles. Each session was videotaped for later analysis by an observer blind to the animal's experimental group. The paw contralateral to the side of the AAV-A53T-α-synuclein injection was marked prior to the start of each test session to definitively determine laterality on videotapes. The test was performed in the late afternoon prior to the onset of the dark cycle. At each test session, the animal was gently placed in the cylinder and movements were videotaped for 10 minutes. Forelimb use was assessed by scoring weight-bearing contacts on the cylinder wall with the ipsilateral, contralateral (relative to the AAV-A53T-α-synuclein-injected side), and both paws. Twenty observations of the paw placements on the cylinder wall were scored. Limb placement on the wall was scored only if it occurred after the animal returned to a resting position and reared again to touch the cylinder wall. Percent ipsilateral (ipsi) and contralateral (contra) paw touches were calculated as [(ipsi+1/2 both)/total #observations]*100 and [(contra+1/2 both)/total #observations]*100, respectively. The cylinder test was performed prior to surgery (baseline) and at 3 and 6 weeks after surgery for the immediate start GM1 groups and at 3 and 8 weeks after surgery for the delayed start GM1 groups.

Measurement of Striatal Dopamine and Metabolite Levels

Striatal samples were sonicated cold in 0.4 M perchloric acid for 10 seconds and centrifuged at 13,000 rpm for 10 min at 4° C. The supernatant was removed and was diluted 1:4 with Milli-Q ultrapure water (resistivity 18.2 M (2 cm) containing internal standard (isoproterenol, 4 ng). The diluted samples were centrifuged again at 13,000 rpm for 5 min at 4° C. Samples were kept on ice prior to loading into the refrigerated (4° C.) autosampler integrated with the HPLC system. An ALEXYS UHPLC system (Antec Scientific) with electrochemical detection (Decade Elite electrochemical detector with a glassy carbon electrode) was used for the analyses. Separations were achieved at 37° C. using an Aquity UPLC column 1.0×100 mm BEH C18 1.7 μm (Waters Corporation). The mobile phase (pH 3.0) consisted of 100 mM phosphoric acid, 100 mM citric acid, 0.1 mM EDTA.Na2, 600 mg/L octanesulfonic acid sodium salt, and 8% acetonitrile. Pump flow rate was 50 μl/min. The analytes were detected at an oxidation potential of 600 mV against a reference electrode at 0 mV. Data were acquired and processed using Clarity software (v7.4.1) (DataApex). Peak heights were compared against internal standard curves to determine the concentrations of DA and metabolites in each sample.

Immunohistochemistry and Stereological Cell Counting

Fixed tissue blocks were immersed in 30% sucrose for cryoprotection and sectioned frozen on a sliding microtome (30 μm section thickness for striatal sections; 40 μm section thickness for SN sections). Sections through the rostro-caudal extent of the SN were collected and every sixth section from the SN was processed for tyrosine hydroxylase (TH) immunohistochemistry to be used for stereological cell counting. Three striatal sections from approximately the level of the decussation of the anterior commissure in each case were processed for α-synuclein immunohistochemistry. For immunohistochemistry, sections were washed and permeabilized with PBS containing 0.2% Triton X-100. Endogenous peroxidase activity was quenched using 3% hydrogen peroxide in PBS containing 0.2% Triton X-100. Sections were then blocked in PBS/triton X-100 containing 10% normal goat serum and 2% BSA, followed by primary antibody incubation (TH (rabbit anti-TH, 1:2,000, Pel-Freez); α-synuclein (mouse anti-α-synuclein clone 211; 1:2000, Millipore) overnight at 4° C. The following day, sections were washed in PBS and incubated in biotinylated secondary antibody (goat-anti-rabbit 1:4000 for TH; goat-anti-mouse 1:2000 for α-synuclein 1:2000, VECTOR Laboratories), followed by additional washes and incubation in avidin biotin complex (VECTASTAIN Elite ABC system, VECTOR Laboratories). The reaction product was visualized with 3,3'-diaminobenzidine (DAB) (Immpact DAB, VECTOR Laboratories). Sections were then mounted, dehydrated, cleared and coverslipped. Sections stained for visualization of TH and to be used for stereological cell counting were counterstained with cresyl violet prior to coverslipping. Stereological estimates of the numbers of TH and cresyl violet-stained neurons in the SNc on both sides of the brain were obtained using StereoInvestigator software (MBF Bioscience) and an Olympus BX-60 microscope equipped with a Ludl motorized stage. Slides were coded and analyzed blindly. The SNc was outlined under low magnification (4×) and a grid measuring 195 μm×85 μm was randomly placed over the region. Cells were then counted at high power (100×) using a counting frame measuring 60 $\mu m^2$. A cell was counted only if a nucleus was clearly identifiable and the cell was within the counting frame and did not contact the left or bottom boundary of the counting frame. This process was repeated for each section in the series for a given animal, and a total of 7-8 sections/animal were analyzed. Nissl-stained cells were counted concurrently in the same sections using the same sampling parameters. Cell counts were considered acceptable with a Gundersen CE<0.1.

Analysis of α-Synuclein and α-Synuclein Positive Aggregates

Immunoblotting for α-synuclein expression was performed using the Wes western blot system (ProteinSimple). Tissue lysates were prepared in standard RIPA buffer supplemented with protease inhibitors and were resolved using the 12-230 KDa Wes separation module according to the manufacturer's recommendations. α-synuclein levels were assayed using anti-α-synuclein antibody (Syn204) (Cat. No. 2647S, Cell Signaling) and normalized to β-actin levels (anti-beta-actin antibody, NB600-503, Novus Biologicals). Recent in vitro studies suggest that GM1 and α-synuclein interact in a way that protects monomeric α-synuclein from potentially pathogenic aggregation. We investigated the extent to which GM1 treatment in vivo might affect the aggregation of α-synuclein by measuring the size of α-synuclein-positive aggregates in the striatum of AAV-A53T animals treated with saline or GM1. The sizes of α-synuclein-positive swelling/aggregates were measured in 3 fields (one medial, one central and one lateral) from 1 coronal section (at the approximate level of the decussation of the anterior commissure). Photographs were captured using a 40× objective on a Nikon Eclipse Ni microscope and α-synuclein-positive structures with an area >5 μm2 were considered as aggregates and were measured using Nikon NIS Elements AR software. Data are presented as the distribution of aggregate sizes in the three striatal regions measured.

Immunoblotting

Immunoblotting for analyzing α-synuclein and β-actin expression was performed using the Wes automated Western blot system based on capillary electrophoresis and immunodetection (ProteinSimple) for enhanced sensitivity and reproducibility at low sample concentrations. Tissue lysates were prepared in RIPA buffer supplemented with protease inhibitors (Halt Protease and Phosphatase Inhibitor Cocktail, Thermo Fisher Scientific) and quantified using the Micro BCA Protein Assay Kit (Thermo Fisher Scientific). For each sample, sufficient volume of mastermix was prepared for loading two capillary wells enabling assay of target (α-synuclein) and control (β-actin) signals, from equal sample amounts, in individual capillaries to minimize any interference in chemiluminescence signal generated by target and control proteins. Sample lysate mastermix was prepared by combining tissue sample lysate (4 μg per well), 0.1× sample buffer and 5× fluorescent mix (200 mM DTT, 5× sample buffer, 5× fluorescent standards) and denaturing at 70° C. for 10 minutes. For each sample, equal amount of denatured lysate mastermix was loaded in two capillary wells of a 12-230 KDa Wes separation module plate and resolved according to the manufacturer's recommendations. α-synuclein levels were assayed using anti-α-synuclein antibody (Syn204) diluted 1:25 (Cat. No. 2647S, Cell Signaling) and β-actin levels were assayed using anti-beta-actin antibody diluted 1:50 (NB600-503, Novus Biologicals). HRP conjugated anti-mouse (Cat no. 042-205) and anti-rabbit secondary antibodies and luminol detection reagents (Cat no. DM-001) were obtained from ProteinSimple. The expression levels of α-synuclein and β-actin were determined by calculating the area under the curve for α-synuclein and β-actin chemiluminescence signals using the Gaussian distribution function of Compass Software (Protein Simple). Finally, α-synuclein signal was normalized to β-actin signal and presented. The Wes Western Immunoblot images were prepared using Compass Software (ProteinSimple).

Exclusion of Animals from Analysis

A total of nine animals from all surgery groups were excluded from analysis due to no evidence of a successful lesion produced by AAV1/2-A53T α-synuclein injection. For technical reasons or for lack of sufficient tissue available for processing, two animals from the early start A-53T-α-synuclein/saline group and four animals from the early start A-53T-α-synuclein/GM1 group were excluded from analysis of stereological cell counts. Also, for technical reasons or for lack of sufficient tissue available for processing, one animal from the delayed start A-53T-α-synuclein/saline group was excluded from the cylinder test analysis and from the analysis of DOPAC levels; two animals from the delayed start A-53T-α-synuclein/GM1 group were excluded from analysis of stereological cell counts and from analysis of DOPAC levels.

Statistical Analyses

All statistics were performed using the GraphPad Prism software (v7). Values are presented as means±SEM. Comparisons between experimental groups were performed using Student's t test or when comparisons involved more than two groups, one-way analysis of variance followed by post hoc comparisons using Bonferroni's multiple comparison test. All analyses were two-sided. The nonparametric Kolmogorov Smirnov test was used to test whether samples of α-synuclein aggregate sizes from saline and GM1-treated animals came from the same distribution or not (i.e., HO: the two samples come from a common distribution; Ha: the two samples do not come from a common distribution). In all cases, statistical significance was set at P<0.05.

Figure 1A:
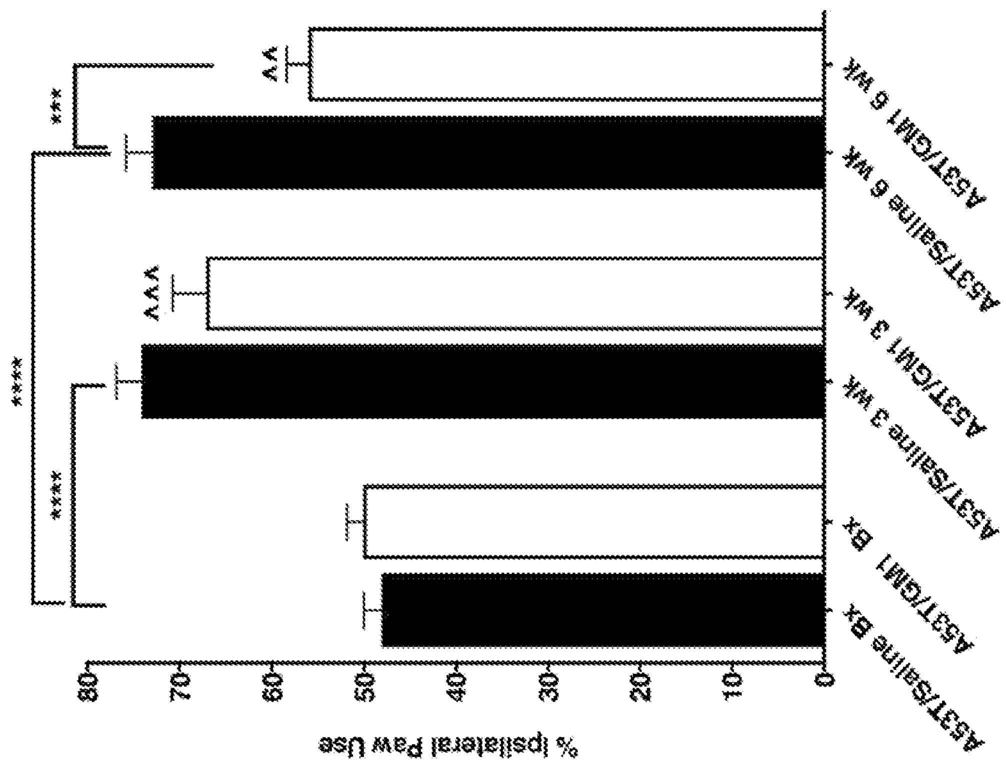

Example 1—Early Start GM1 Administration Partially Protects Motor Behavior and Striatal DA Levels The cylinder test was used to assess spontaneous forelimb use in AAV-A53T α-synuclein-transduced animals and there was significant main effect of treatment, with a protective effect observed in GM1-treated animals (F(5,102)=16.59, P<0.0001). Animals that received AAV-A53T α-synuclein followed by saline for 6 weeks developed a significant asymmetry in paw use with preference for making contact with the cylinder with ipsilateral forepaw relative to the side of virus injection. At 3 weeks following AAV-A53T α-synuclein injection, saline-treated animals already showed a significant increase in percent ipsilateral limb use that continued to be observed at 6 weeks post virus injection (mean±SEM: baseline: 48.1±1.9%; 3 weeks: 74.2±2.7%, 6 weeks: 72.9±2.9%) (FIG. 1A). In animals that received GM1 administration beginning 24 hours after AAV-A53T α-synuclein injection, limb use asymmetry (percent ipsilateral limb use) was also increased at 3 weeks and 6 weeks after AAV-A53T α-synuclein injection but this increase was only significantly different from baseline at 3 weeks (mean±SEM: baseline: 50.1±1.8%; 3 weeks: 67.1±3.7%, 6 weeks: 56.0±2.5%) (FIG. 1A). The amount of limb use asymmetry was significantly less in GM1-treated animals at 6 weeks compared to saline-treated animals at 6 weeks (P<0.0001) (FIG. 1A). Animals that received AAV empty vector injections had no significant changes in limb use (% ipsilateral limb use: baseline: 48.8±2.3%; 3 weeks: 53.7±4.2%; 6 weeks: 58.5±4.1%; (F(2,9)=2.521, P=0.1173).

Figure 1C:
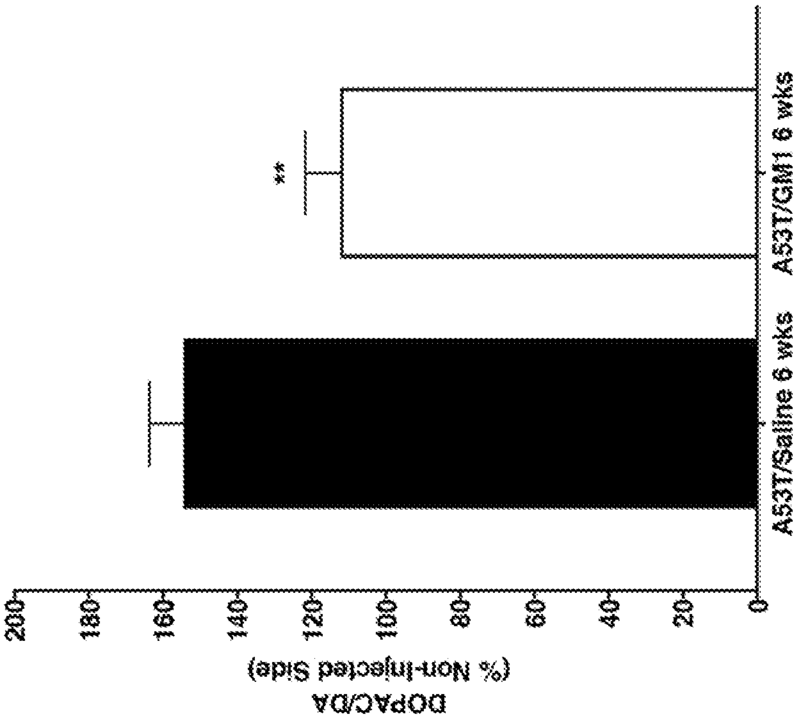

Six weeks following AAV-A53T α-synuclein injection, striatal DA levels on the side ipsilateral to the injection in saline-treated animals were 47.8±4.5% of the DA levels on the side contralateral to the injection (i.e., the non-injected side). In animals that began receiving GM1 administration 24 hours after surgery, striatal DA levels on the side ipsilateral to the injection were 64.0±3.5% of the DA levels on the side contralateral to the injection (t(34)=2.858, P=0.0072 vs. saline-treated) (FIG. 1B, Table 1). DOPAC/DA ratios on the side ipsilateral to the injection in the saline-treated animals were 154.5±9.2% of the contralateral (non-injected) side while in GM1-treated animals, DOPAC/DA ratios on the side ipsilateral to the injection were 112.3±9.5% of the contralateral (non-injected) side (t(34)=3.092, P=0.0040 vs. saline-treated) (FIG. 1C). Injection of the AAV empty vector had no significant effects on striatal DA levels (non-injected side: 10.57±0.47 μg/g wet weight; injected side: 11.04±0.69 μg/g wet weight, N=9, P=0.5775).

TABLE 1

Effects of AAV-A53T-α-synuclein and GM1 ganglioside administration on striatal dopamine (DA) and dihydroxyphenylacetic acid (DOPAC) levels

| Treatment | n | DA (μg/g wet tissue) | DOPAC (μg/g wet tissue) |
|---|---|---|---|
| AAV-A53T/Saline: Non-Injected Side (6 wks) | 15 | 10.34 ± 0.47 | 1.02 ± 0.08 |
| AAV-A53T/Saline: Injected Side (6 wks) | 15 | 4.99 ± 0.55 | 0.79 ± 0.09 |
| AAV-A53T/Early GM1: Non-Injected Side | 21 | 11.43 ± 0.32 | 1.33 ± 0.10 |
| AAV-A53T/Early GM1: Injected Side | 21 | 7.29 ± 0.45[a] | 0.85 ± 0.09 |
| AAV-A53T/Saline: Non-Injected Side (8 wks) | 12 | 11.44 ± 0.59 | 1.43 ± 0.18^ |
| AAV-A53T/Saline: Injected Side (8 wks) | 12 | 3.62 ± 0.54 | 0.85 ± 0.09^ |
| AAV-A53T/Delayed GM1: Non-Injected Side | 19 | 10.73 ± 0.54 | 1.18 ± 0.10^ |
| AAV-A53T/Delayed GM1: Injected Side | 19 | 5.87 ± 0.47[b] | 0.93 ± 0.12^ |

[a]P = 0.0026 vs. AAV-A53T/Saline;
[b]P = 0.004 vs. AAV-A53T/Saline;
^Two samples were determined to be extreme outliers by Grubbs' test and were removed from the analysis.

Figure 2B:
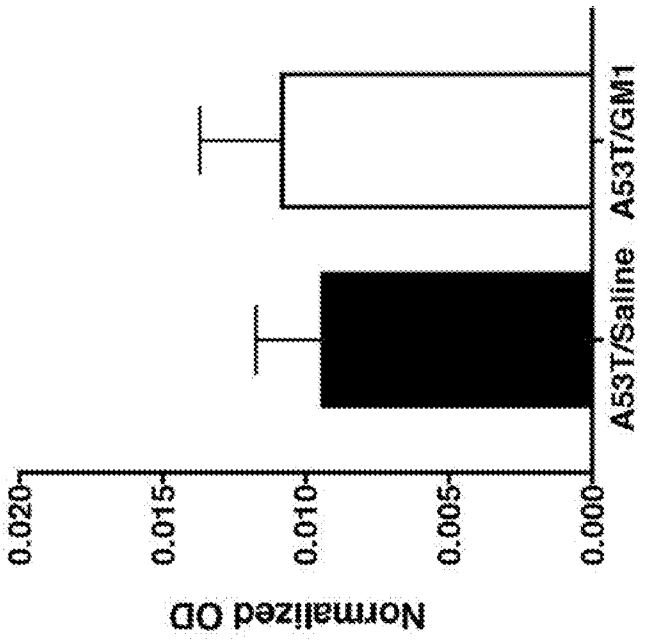
FIGS. 2A-2C illustrate early start GM1 administration did not affect α-synuclein expression or transport to the striatum.
Figure 2A:
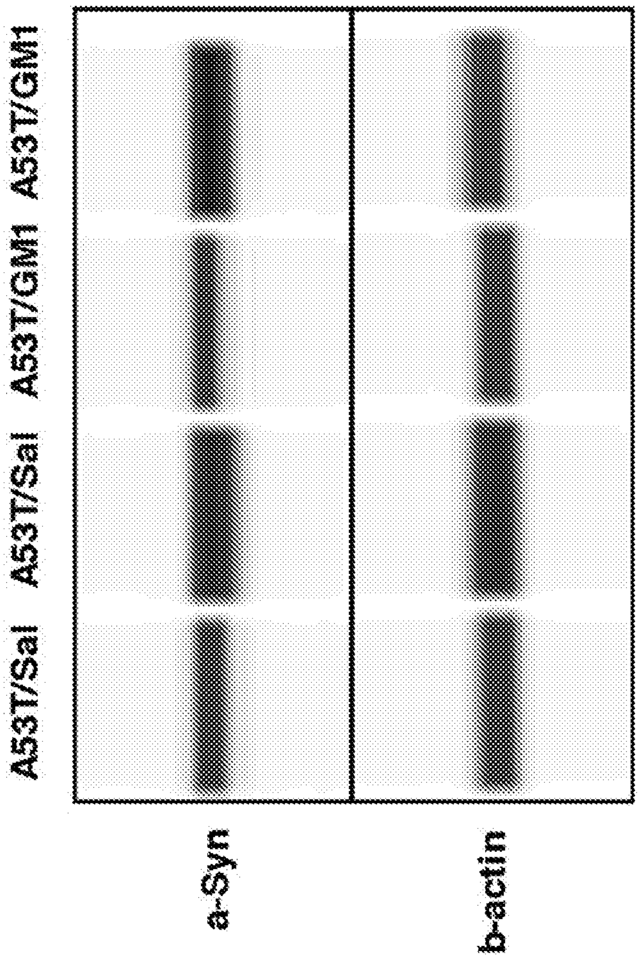
Figure 2C:
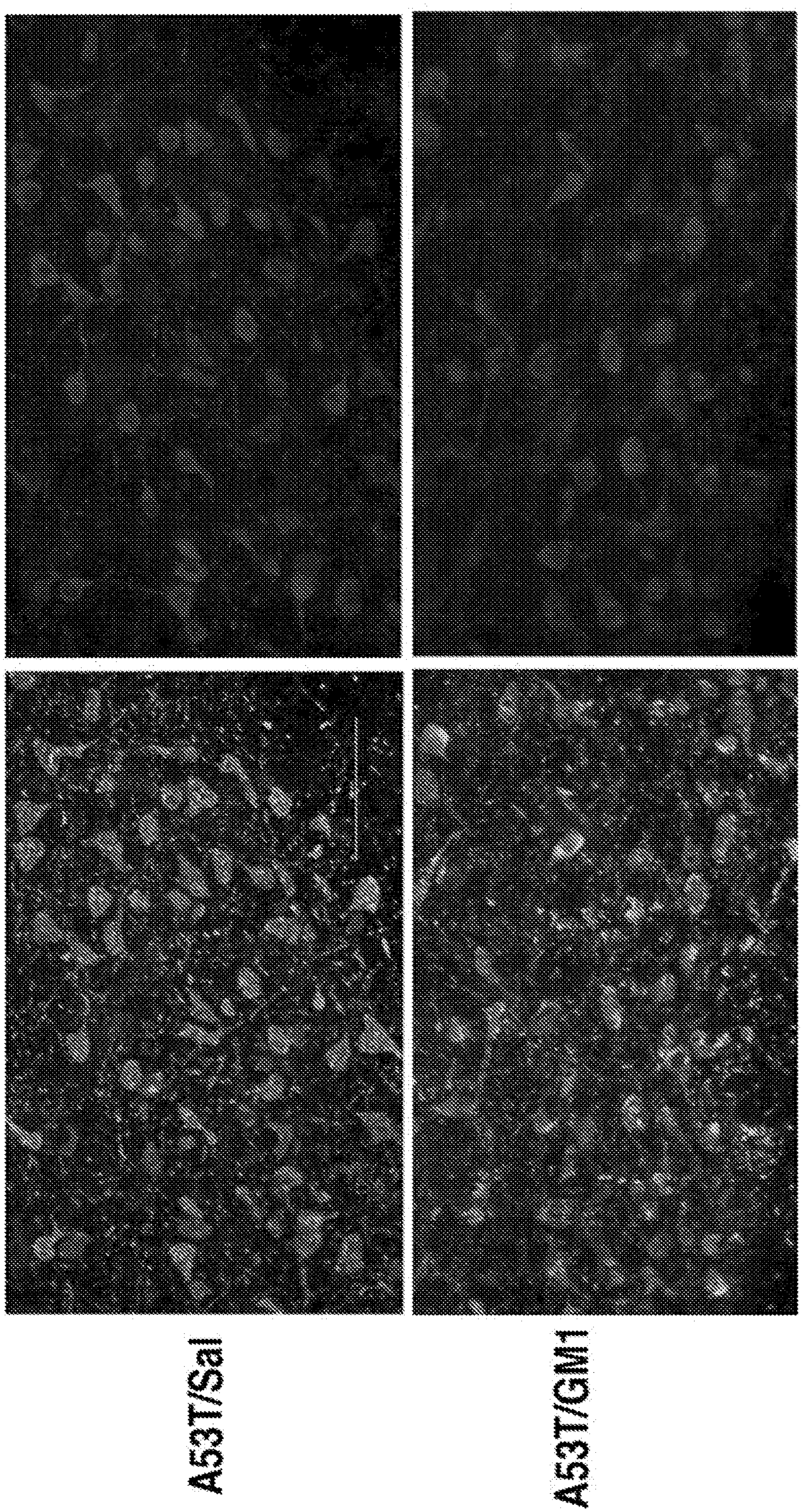

The positive effects observed with GM1 administration beginning 24 hours after AAV-A53T α-synuclein injection cannot be explained by GM1 interfering with the transduction of the A53T α-synuclein gene by the AAV vector and expression of α-synuclein protein. When assessed at 1 week following AAV-A53T α-synuclein injection, levels of striatal α-synuclein were no different in saline vs. GM1-treated animals, suggesting no influence of GM1 on A53T α-synuclein transduction or transport to the striatum (normalized OD: 0.014±0.004 and 0.017±0.007, respectively, t (12)=0.4412, P=0.6669) (FIGS. 2A-2B). Immunohistochemical evaluation of the SNc 1 week after AAV-A53T α-synuclein injection also showed no differences between saline and GM1-treated animals in α-synuclein accumulation in TH+ neurons (FIGS. 2C-2D).

Figure 3B:
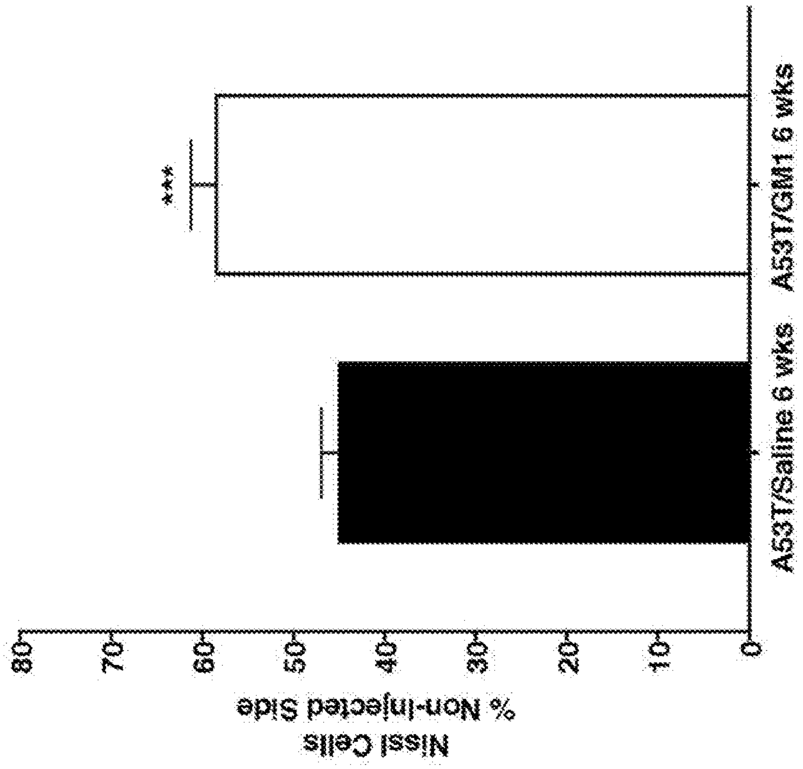
FIGS. 3A-3D illustrate that early start GM1 administration partially protected against loss of SNc dopaminergic neurons.
Figure 3A:
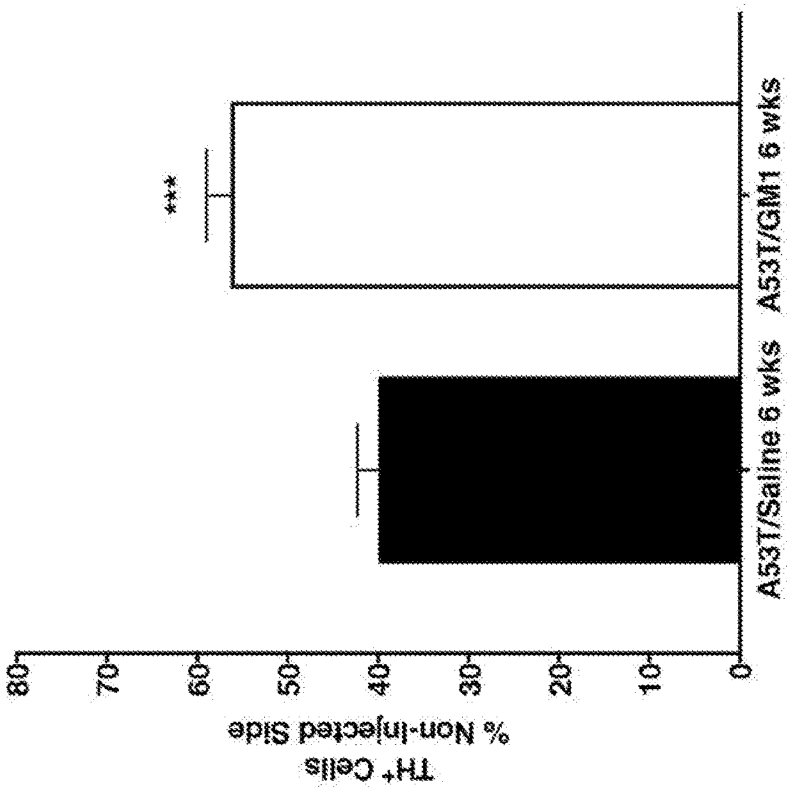
Figure 3D:
Figure 3C:
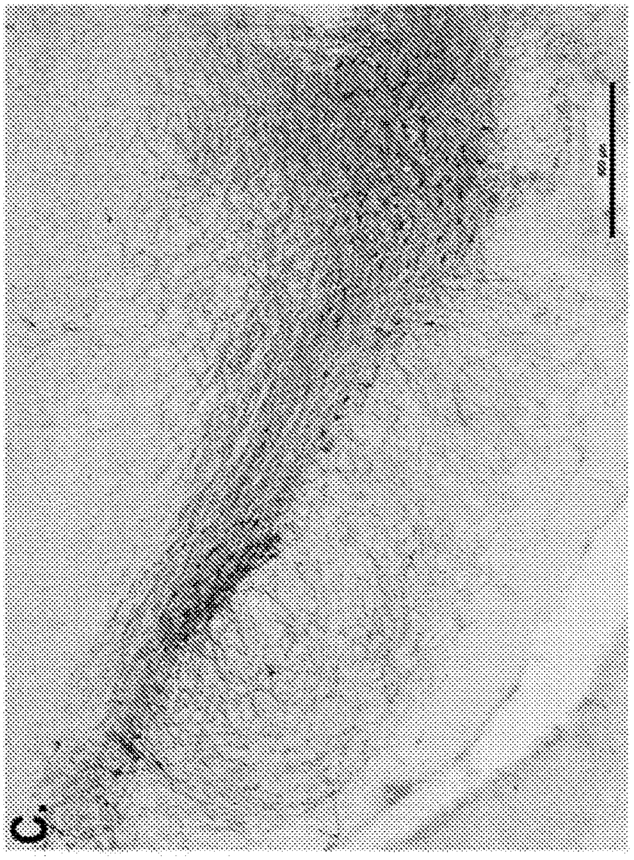

Example 2—Early Start GM1 Administration Partially Protects SN Neurons Against α-Synuclein-Induced Toxicity To investigate the potential protective role of GM1 in the context of PD-relevant pathology, the extent to which GM1 administration affected survival of A53T α-synuclein-overexpressing nigral DA neurons was examined. The number of TH+ cells in the SNc was significantly decreased on the side ipsilateral to the injection: AAV-A53T-α-synuclein injection resulted in a 60.0±2.3% loss of TH+ neurons, compared to the contralateral (non-injected) side (FIGS. 3A-3B). Animals that received early start GM1 administration had 43.7±2.7% loss of TH+ neurons, compared to the non-injected side (t(28)=4.379, P=0.0002) (FIGS. 3A-3B; Table 2). Similarly, the number of cresyl violet-stained cells in the SNc was significantly influenced by AAV-A53T-α-synuclein injection and by GM1 treatment. AAV-A53T-α-synuclein injection caused a 54.9±1.8% loss of cresyl violet-stained neurons, compared to the contralateral side. GM1-treated animals had only a 41.9±2.5% loss of cresyl violet-stained neurons, compared to the contralateral side (t(28)=3.997, P=0.0004) (Table 2). Injection of the AAV empty vector had no significant effects on SN neurons: counts of TH+ neurons were 95.4±1.1% of the non-injected side; counts of cresyl violet-stained neurons were 95.6±1.3% of the non-injected side.

TABLE 2

Effects of AAV-A53T-a-synuclein and GM1 ganglioside administration on substantia nigra pars compacta dopamine neurons

| Treatment | n | $TH^+$ Cells | $Nissl^+$ Cells |
|---|---|---|---|
| AAV-A53T/Saline: Non-Injected Side (6 wks) | 13 | 5831 ± 189 | 6174 ± 157 |
| AAV-A53T/Saline: Injected Side (6 wks) | 13 | 2314 ± 140 | 2784 ± 128 |
| AAV-A53T/Early GM1: Non-Injected Side | 17 | 5601 ± 135 | 6074 ± 174 |
| AAV-A53T/Early GM1: Injected Side | 17 | 3144 ± 159[a] | 3557 ± 172[b] |
| AAV-A53T/Saline: Non-Injected Side (8 wks) | 12 | 5621 ± 183 | 5972 ± 172 |
| AAV-A53T/Saline: Injected Side (8 wks) | 12 | 2052 ± 177 | 2480 ± 159 |
| AAV-A53T/Delayed GM1: Non-Injected Side | 17 | 5685 ± 143 | 6113 ± 132 |
| AAV-A53T/Delayed GM1: Injected Side | 17 | 2814 ± 134[c] | 3335 ± 148[d] |

[a]P = 0.0008 vs. AAV/A53T/Saline;
[b]P = 0.002 vs. AAV-A53T/Saline;
[c]P = 0.0017 vs. AAV-A53T/Saline;
[d]P = 0.0006 vs. AAV-A53T/Saline.

Figure 4A:
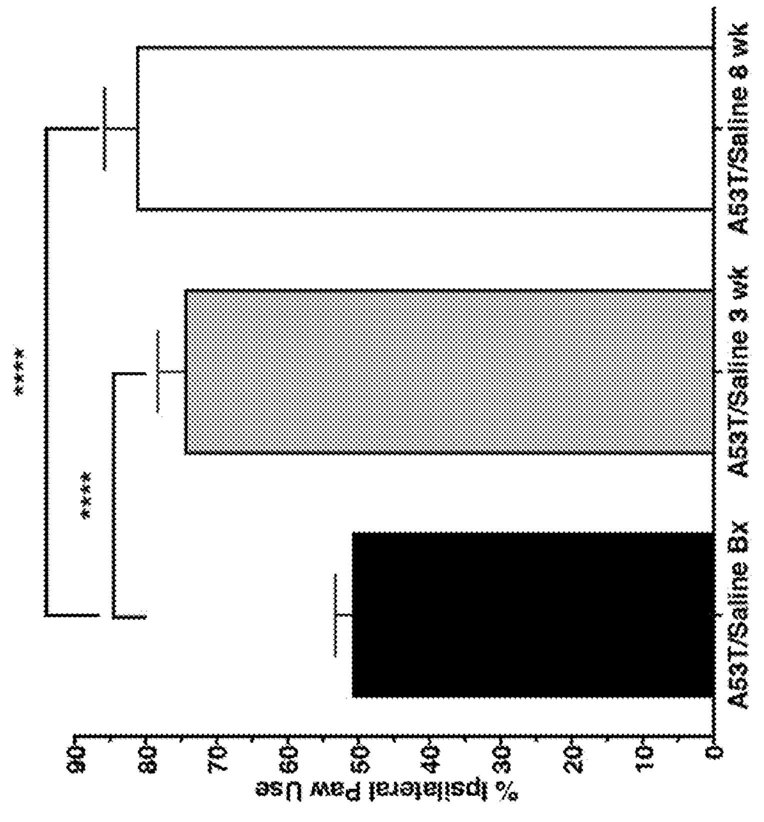
FIGS. 4A-4D illustrate that delayed start GM1 administration (beginning 3 weeks after AAV-A53T α-synuclein injection) partially restores motor function and partially protects striatal dopamine levels.
Figure 4B:
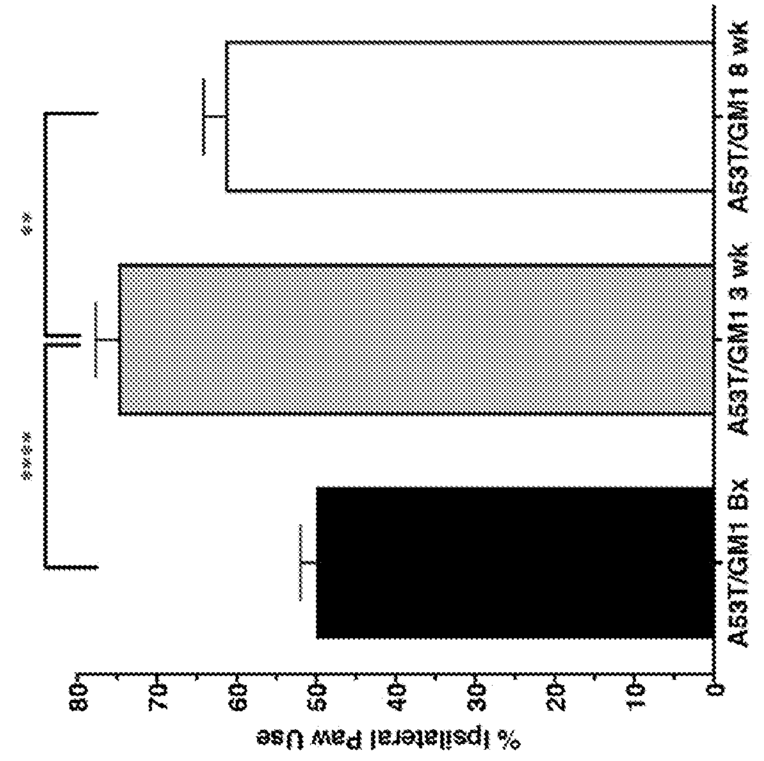

Example 3—Delayed Start Gm1 Administration Partially Restores Motor Behavior and Protects Striatal DA Levels Animals that received AAV-A53T α-synuclein followed by saline for 8 weeks also developed a significant asymmetry in paw use with preference for making contact with the cylinder with the forepaw ipsilateral to the virus injection (FIG. 4A). When tested at 3 weeks following AAV-A53T α-synuclein injection, saline-treated animals showed a significant increase in percent ipsilateral limb use, similar to what was seen in the animals described earlier, that continued to be observed at 8 weeks post virus injection (mean±SEM; baseline: 50.9±2.4%; 3 weeks: 74.5±3.8%, 8 weeks: 81.4±4.5%) (FIG. 4A). There was a significant treatment effect favoring the GM1-treated group ($F(5,84)=19.14$, $P<0.0001$). Animals assigned to the GM1 group had baseline percent ipsilateral limb use (50.0±2.0%) comparable to that of the saline group and an increase in percent ipsilateral forelimb use at week 3 (74.9±2.8%), also comparable to that observed in the saline group. These animals then received daily GM1 administration for the next five weeks and when tested again at week 8, showed a significant decrease in percent ipsilateral forelimb use (i.e, an increase in contralateral limb use) (61.5±2.7%) compared to performance at week 3 just prior to receiving GM1 treatment (P=0.0075 vs. week 3) (FIG. 4B).

Figure 4D:
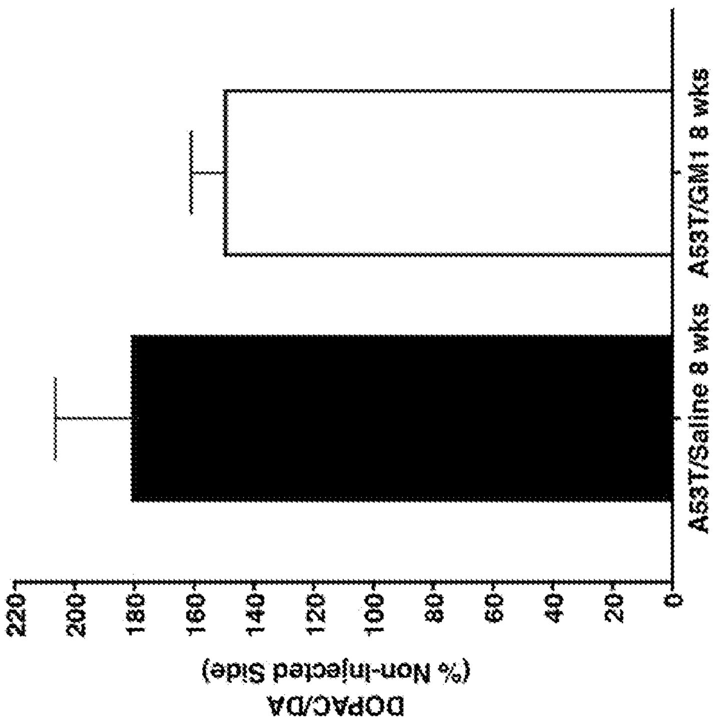
Figure 4C:
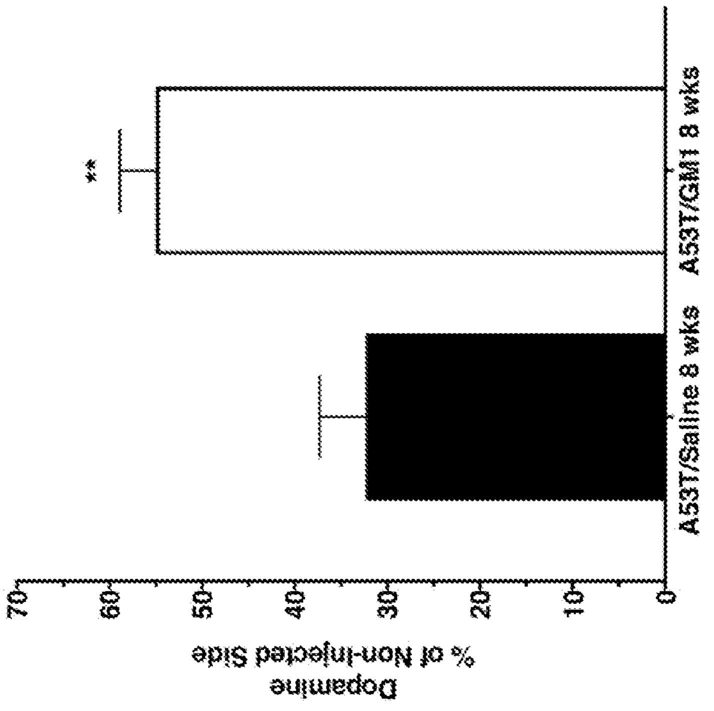

Eight weeks following AAV-A53T α-synuclein injection, striatal DA levels on the virus injected side of the brain in saline-treated animals were 32.3=5.0% of the DA levels on the contralateral (non-injected) side. In animals that began receiving GM1 administration 3 weeks after surgery, striatal DA levels on the virus ipsilateral (injected) side of the brain were 55.0±3.9% of the DA levels on the contralateral side ($t(29)=3.565$, P=0.0013 vs. saline-treated) (FIG. 4C). DOPAC levels on the injected side in the saline-treated animals were 69.4±7.4% of the contralateral side while in GM1 treated animals, DOPAC levels on the injected side were 82.0±8.4% of the non-injected side, an increase but not statistically significantly different from saline-treated animals (FIG. 4D). DOPAC/DA ratios on the side ipsilateral to the injection in the saline-treated animals were 181.1±25.4% of the contralateral side while in GM1-treated animals, DOPAC/DA ratios on the side ipsilateral to the injection were 150.0±10.9% of the contralateral side, although this difference was not statistically significant.

Figure 5B:
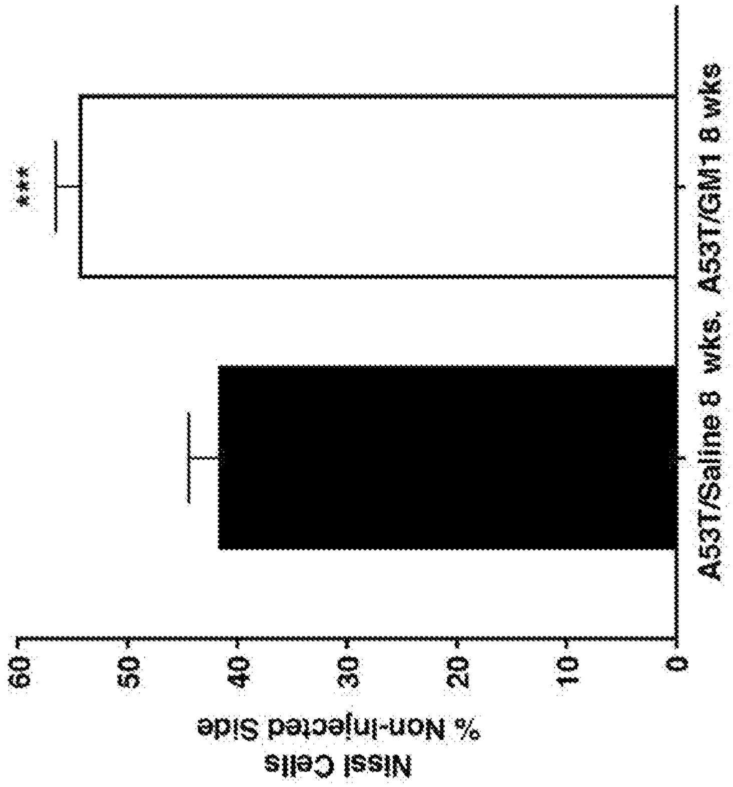
FIGS. 5A-5D illustrate that delayed start GM1 administration partially protected against loss of SNc dopaminergic neurons.
Figure 5A:
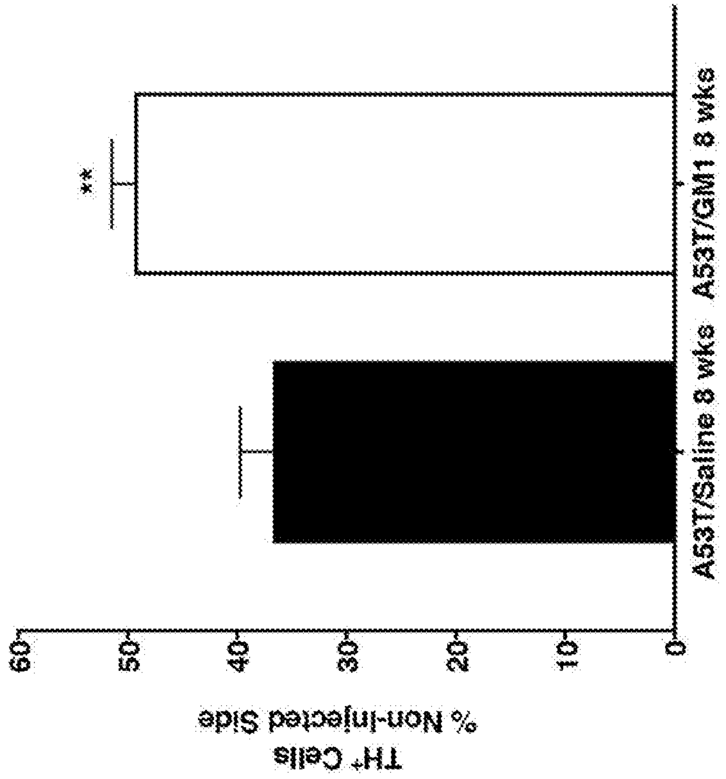
Figure 5D:
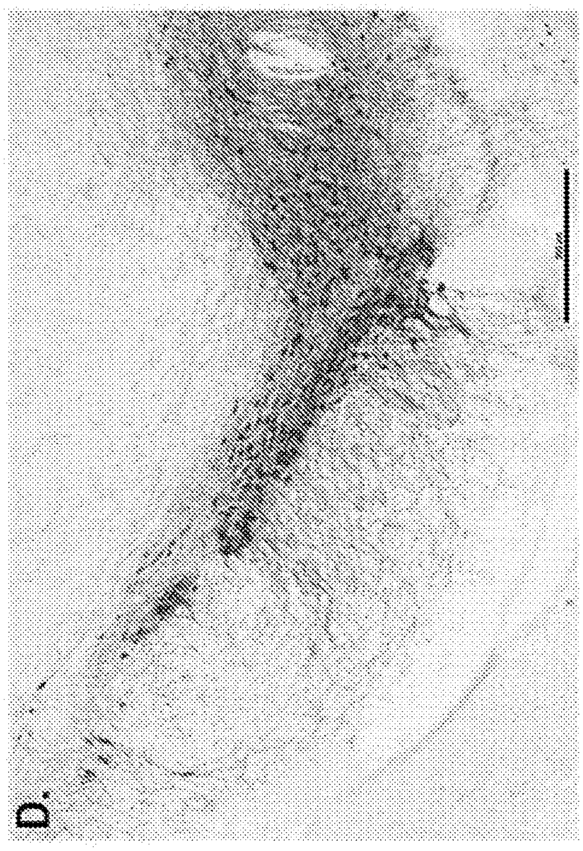
Figure 5C:

Example 4—Delayed Start GM1 Administration Partially Protects SN Neurons Against α-Synuclein-Induced Toxicity The extent to which delayed start administration of GM1 could affect survival of A53T α-synuclein-overexpressing nigral DA neurons was examined. The number of TH+ cells in the SNc was significantly decreased on the side ipsilateral to the injection: AAV-A53T-α-synuclein injection resulted in a 63.3±3.0% loss of TH+ neurons, compared to the contralateral (non-injected) side. Animals that received delayed start GM1 administration had 50.6±2.1% loss of TH+ neurons, compared to the contralateral side ($t(27)=3.58$, P=0.0013) (FIGS. 5A-5B; Table 2). The number of cresyl violet-stained cells in the SNc was also significantly influenced by AAV-A53T-α-synuclein injection and by delayed start GM1 treatment. AAV-A53T-α-synuclein injection caused a 58.2±2.6% loss of cresyl violet-stained neurons, compared to the contralateral side. Delayed start GM1-treated animals had only a 45.5±2.1% loss of cresyl violet-stained neurons, compared to the contralateral side ($t(27)=3.796$, P=0.0008) (Table 2).

Example 5—α-Synuclein Aggregation is Reduced by GM1 Administration

Figure 6A:
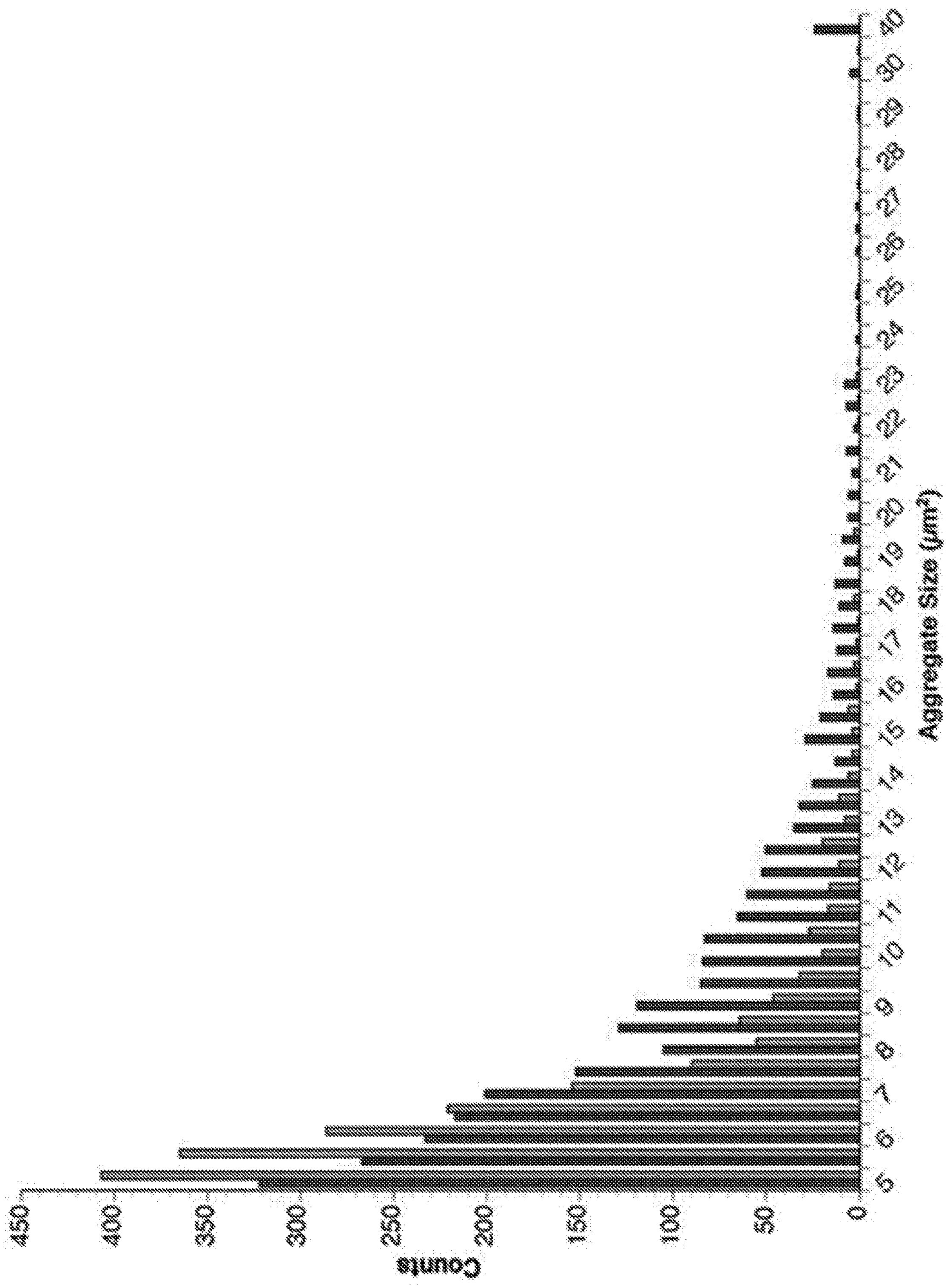
FIGS. 6A-6D illustrate that GM1 treatment reduces the number and size of α-synuclein-positive aggregates in the striatum.
Figure 6B:
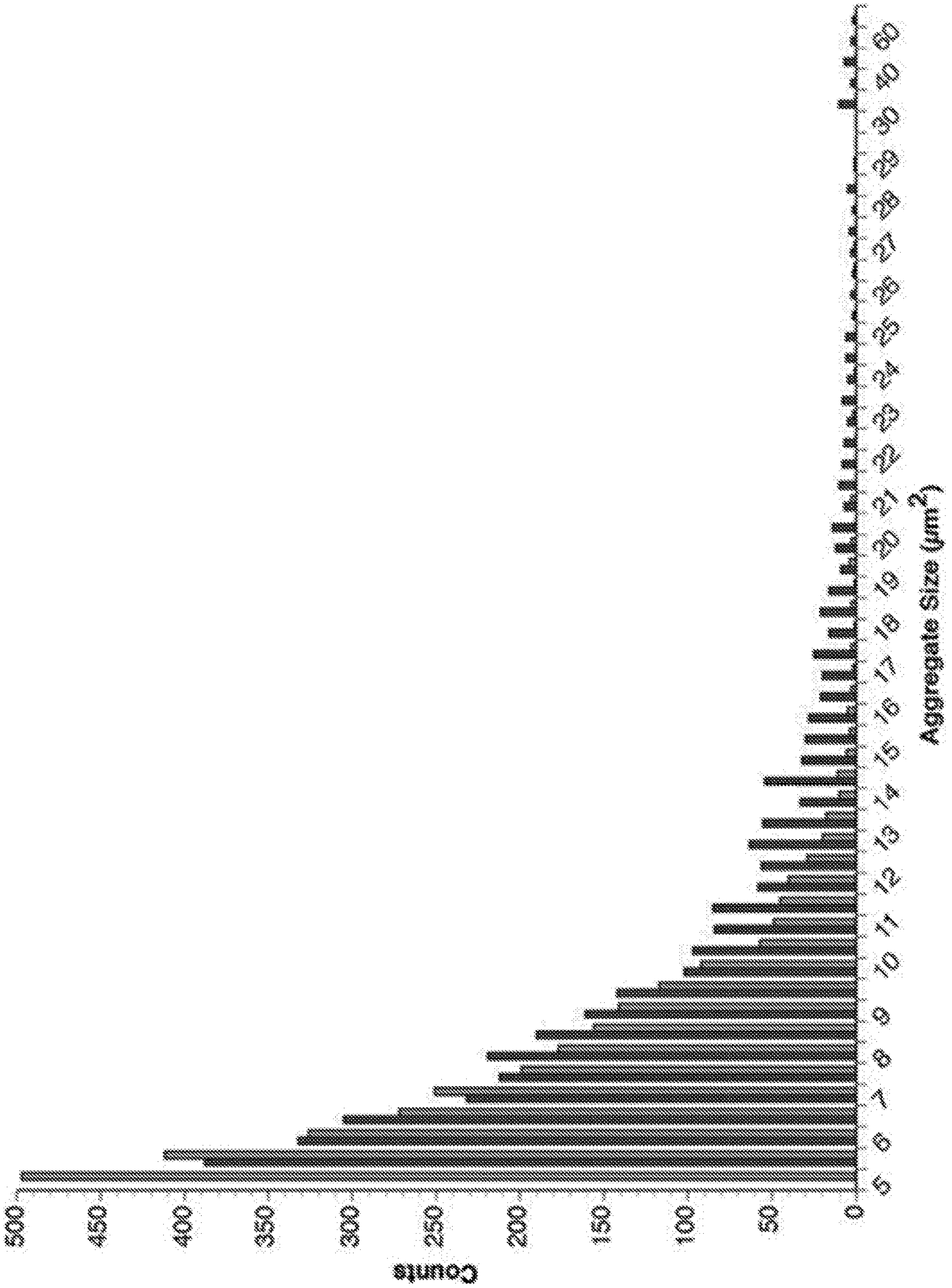
Figure 6D:
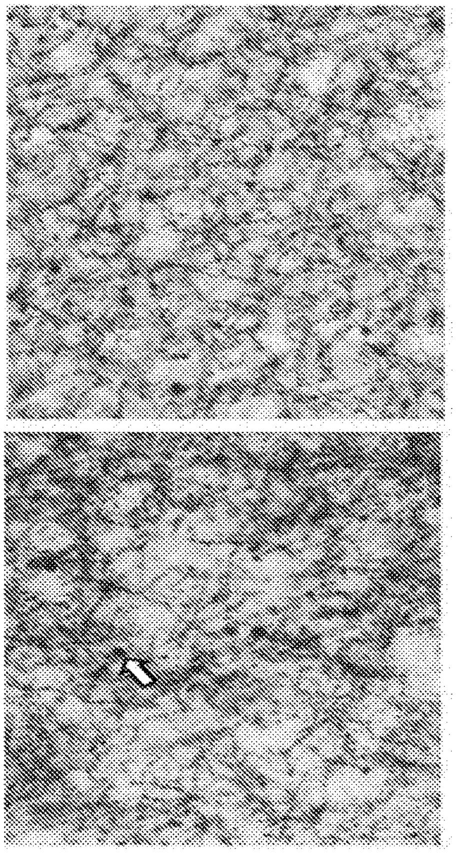
Figure 6C:
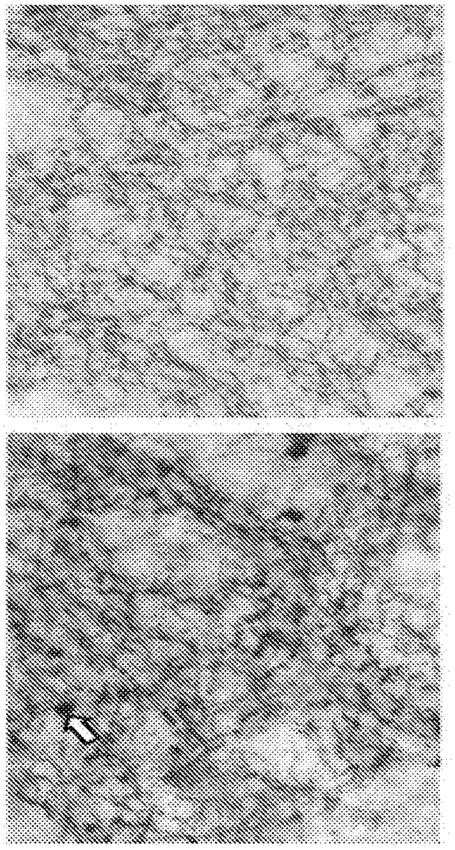
Figure 7B:
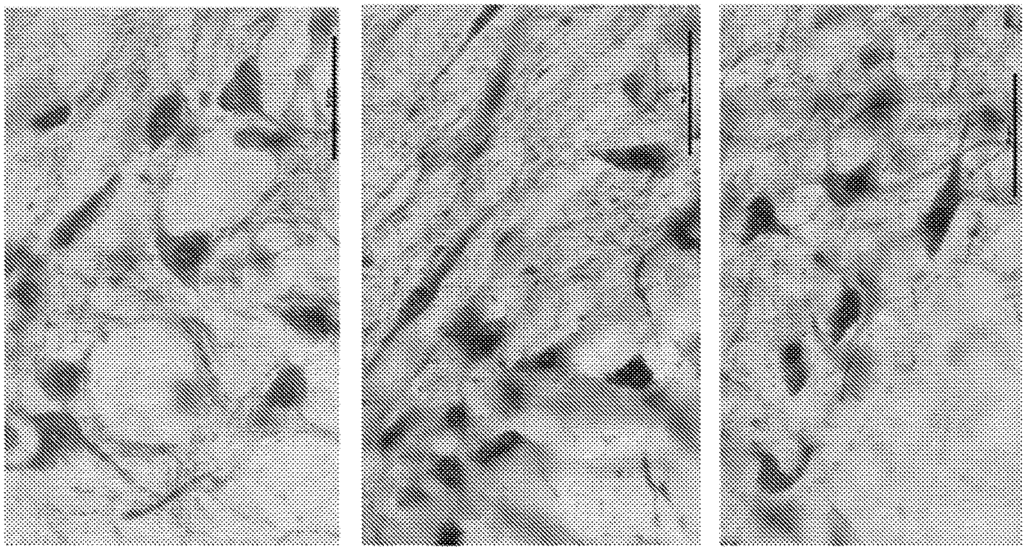
FIGS. 7A-7B illustrate immunohistochemical staining of SN sections for visualization of Ser129 phosphorylated α-synuclein in saline-treated (FIG. 7A) animals 8 weeks after AAV-A53T-α-synuclein injection and in delayed start GM1-treated animals (FIG. 7B). There was more Ser129 phosphorylated α-synuclein staining in saline-treated animals compared to GM1-treated animals and staining appeared more intense and appeared to fill more of the neuron in saline-treated animals compared to GM1-treated animals.
Figure 7A:
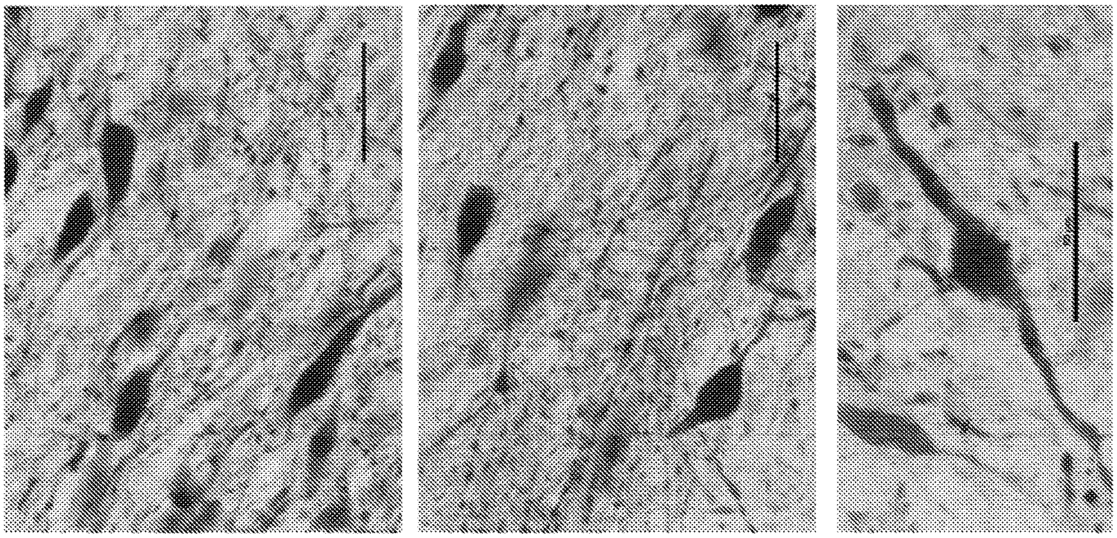
Figure 8:
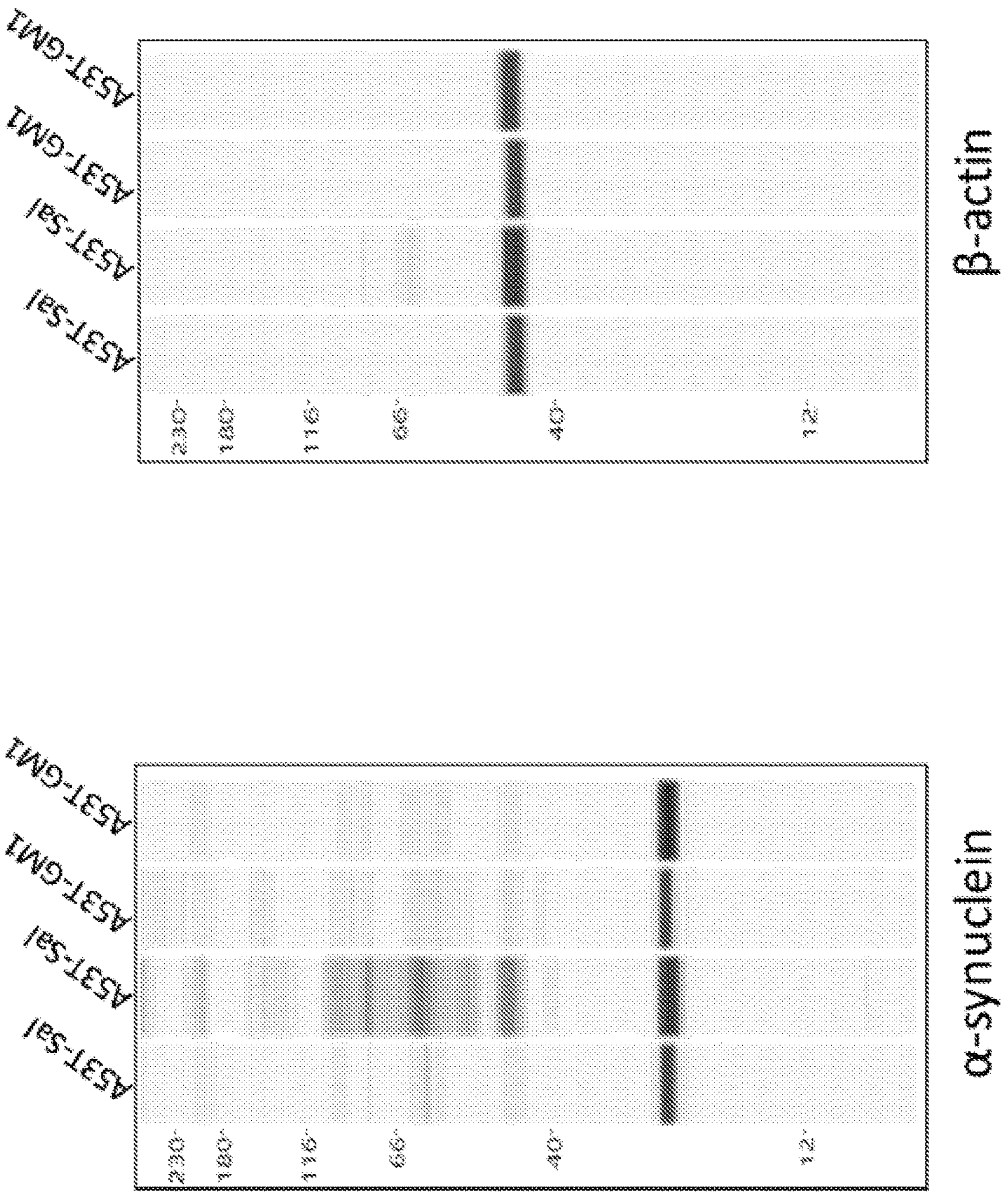
FIG. 8 illustrates full length Wes immunoblots of images presented in FIG. 2.

Since previous in vitro studies suggest that GM1 and α-synuclein (both wildtype and the A53T mutation) interact in a way that potentially inhibits pathogenic aggregation, it was hypothesized that GM1 administration to AAV-A53T overexpressing animals would result in less α-synuclein aggregation and thus smaller sized aggregates. Thus, the effect of early or delayed start GM1 administration on the size of α-synuclein-positive swellings/aggregates in the striatum was examined. The size distributions of striatal α-synuclein-positive aggregates in saline-treated compared to GM1-treated (staring 24 hours after AAV-A53T administration) were significantly different (Kolmogorov-Smirnov D=0.2945, P<0.0001), with a clear shift to larger numbers of smaller sized aggregates and fewer larger sized aggregates in the GM1 groups compared to the saline group (FIGS. 6A-6C). The maximum aggregate size measured in the saline group was 52.5 $\mu m^2$ while the maximum aggregate size measured in the GM1-treated animals was 28.8 $\mu m^2$. Similar results were obtained with measurements of aggregate size distributions in animals with delayed start GM1 administration compared to saline-treated animals. The size distributions of striatal α-synuclein-positive aggregates in saline-treated compared to GM1-treated (starting 3 weeks after AAV-A53T administration) were significantly different (Kolmogorov-Smirnov D=0.154, P<0.0001), with greater numbers of larger sized aggregates in the saline group compared to the GM1 group (FIGS. 6B-6D). The maximum aggregate size measured in the saline group was 66.9 $\mu m^2$ while the maximum aggregate size measured in the GM1-treated animals was 29.3 $\mu m^2$. Compared to animals that started receiving GM1 24 hours after AAV-A53T administration, animals that received GM1 starting 3 weeks after AAV-A53T administration had greater numbers of intermediate-sized aggregates (approximately 7-12 $\mu m^2$), but like the early start GM1 group, had fewer larger sized aggregates than the saline group. Although the accumulation of Ser129-phosphorylated α-synuclein was not quantified, immunohistochemical visualization of Ser129-phosphorylated α-synuclein-positive neurons and neurites in the SN of GM1-treated and saline-treated animals showed less intense cytoplasmic Ser129-phosphorylated α-synuclein staining and fewer/smaller nuclear aggregates in GM1-treated animals compared to saline-treated animals (FIGS. 7A-7B).

Example 6—Discussion

GM1 ganglioside has had beneficial effects on striatal DA levels and behavior and has protected SNc DA neurons against degeneration in neurotoxin (primarily MPTP) models of PD. GM1 has also been shown to have symptomatic effects and with extended use, may slow symptom progression in PD patients. The present results demonstrate that GM1 administration is also able to exert neuroprotective and potentially neurorestorative effects on the nigrostriatal DA system in a PD model characterized by targeted overexpression of human mutated α-synuclein (A53T) in SNc neurons. These data are particularly interesting considering that other compounds that have been found to be neuroprotective in MPTP mouse or nonhuman primate models of PD have not had this preclinical success translated to the α-synuclein model or to the clinic. Although there are several possible reasons why compounds such as GDNF, neurturin, CoQ10, CEP-1347, GPI-1485, pioglitazone, exenatide, and others that showed promising neuroprotective effects in MPTP models failed to demonstrate clear disease-modifying effects in clinical trials, the relevance and translatability of the MPTP (and other toxin-based) models of PD have been called into question, based on the assumption that the toxin models do not faithfully replicate key aspects of the disease. However, clinical translational failures may be as much due to specific characteristics of the compounds tested as to deficiencies in the preclinical models. Here it is shown that unlike these other compounds, GM1 is neuroprotective in mouse and nonhuman primate MPTP models, is neuroprotective in an AAV-α-synuclein model that reproduces DA neuron degeneration and dysfunction based on a core molecular feature of PD (i.e., toxicity associated with accumulation of aberrant α-synuclein, and that these preclinical successes have translated to positive effects in initial clinical trials. In the current study, a behavioral deficit was observed on the cylinder test at 3 weeks following AAV-A53T α-synuclein injection. Although animals were not euthanized in this study at this 3 week period, a previous in-depth characterization of this model, using exactly the same vector and vector concentration as used here, showed that the cylinder test deficit observed at 3 weeks appeared in the absence of significant loss of SN DA neurons or striatal DA levels but in the presence of moderate dystrophic axonal morphology in the striatum. Animals treated with GM1 beginning 24 hours after AAV-A53T α-synuclein injection were already beginning to show reduced use of the forelimb contralateral to the injection when tested at 3 weeks and by 6 weeks following AAV-A53T α-synuclein injection, this effect became statistically significant, with ratio of ipsilateral/contralateral forelimb use approximating that observed at baseline (prior to AAV-A53T α-synuclein injection). At 6 weeks, GM1-treated animals also had significantly higher striatal DA levels than saline-treated animals. The results also showed that early start GM1 treatment did not interfere with the expression or transport of α-synuclein. These results suggest that early start GM1 therapy, while not interfering with the transduction of A53T α-synuclein by the AAV vector and expression/transport of α-synuclein, did interfere with the pathological processes set in motion from the accumulation of α-synuclein. Of considerable interest was the finding that delayed start GM1 treatment could significantly reverse the behavioral deficit observed at 3 weeks following AAV-A53T α-synuclein injection. As suggested by others, the behavioral deficits seen at the 3 week time-point are a result of A53T α-synuclein-induced dysfunction of a relatively anatomically intact nigrostriatal pathway. Starting GM1 therapy at this time-point was able to afford some protection against the degeneration of SNc DA neurons and loss of striatal DA even once the pathological process of α-synuclein accumulation had begun, and was able to reverse the forelimb use deficit observed at 3 weeks, as observed at 8 weeks post AAV-A53T α-synuclein injection. The mechanisms underlying the neuroprotective efficacy of GM1 in this model are not entirely known at this time. It was observed that in animals administered GM1 there was decreased aggregation of α-synuclein and preliminary observations indicate that GM1 may also decrease α-synuclein phosphorylation, potentially decreasing the accumulation of toxic forms of α-synuclein. Phosphorylation of α-synuclein at Ser129 promotes α-synuclein fibril formation and the majority of α-synuclein deposited in Lewy bodies in the PD brain is extensively phosphorylated at Ser129. A53T α-synuclein as well as wild type α-synuclein can form insoluble toxic fibrillary aggregates and mutant α-synuclein may be more prone to aggregation and toxicity than wild type α synuclein. It was observed that both early start and delayed start use of GM1 following AAV-A53T α-synuclein injection reduced the size of α-synuclein aggregates measured in the striatum. In vitro studies have shown a direct association between GM1 and α-synuclein, attributed to interaction between helical-synuclein and both the sialic acid and carbohydrate moieties of GM1, and that this association with GM1 inhibited fibrillation. Decreased expression of GM1 and other complex gangliosides in the SN in PD and decreased expression of genes involved in ganglioside biosynthesis in DAergic neurons in the PD SN. Without wishing to be bound by theory, it is conceivable that reduced levels of gangliosides, and particularly GM1, in the PD SN may promote the accumulation of toxic α-synuclein and that administration of GM1 may provide sufficient amounts of this important sphingolipid so as to at least partially inhibit the toxic aggregation of α-synuclein and provide some level of protection to SN DA neurons. This possibility is supported by studies with B4galnt1 knockout mice, devoid of GM1 and other α-series gangliosides, that reported increased amounts of α-synuclein aggregation in knockout mice devoid of GM1 that could at least be partially reduced by administration of GM1 and the semi-synthetic GM1 derivative LIGA-20.

Another possible mechanism underlying the neuroprotective effects of GM1 observed in the current study may involve influences of GM1 on autophagy and lysosomal function. Dysfunction of the autophagy-lysosomal pathway has been suggested to contribute to PD pathology. Overexpression of A53T-α-synuclein suppresses autophagy and pathogenic A53T-α-synuclein is poorly processed and cleared by chaperone-mediated autophagy. Under conditions of impaired autophagy, GM1, either in vivo or in vitro, increased expression of autophagic markers and enhanced autophagy. Depletion of endogenous gangliosides resulted in compromised lysosomal functions and suppression of autophagy, leading to accumulation of both α-synuclein and P123H β-synuclein in a cellular model of Lewy body disease. It is possible that in the current study, autophagic processes were impaired by A53T-α-synuclein overexpression contributing to enhanced α-synuclein aggregation and DAergic cell loss and that GM1 treatment enhanced lysosomal function and increased autophagic clearance of α-synuclein. Additional studies are now needed to investigate this potential mechanism in regard to the neuroprotective effects of GM1 in this model.

The AAV-A53T α-synuclein model that was used for this study was the same model described previously as producing a specific and progressive degeneration of the nigrostriatal DA system. Animals were not euthanized at early time-points following AAV-A53T α-synuclein injection and thus, the progressive nature of the pathology was not verified. However, in early pilot studies when establishing the model, a steady increase in forelimb use asymmetry was detected over the first 3 weeks post-injection. Although a limited examination of phosphorylated Ser 129 α-synuclein expression by immunohistochemistry was performed, there were not sufficient tissues available for systematic evaluation of levels of phosphorylated Ser 129 α-synuclein. Likewise, the presence of insoluble phosphorylated α-synuclein aggregates was not directly assessed. Striatal α-synuclein aggregates have been shown to be extensively phosphorylated at Ser129 in rats with AAV-mediated A53T-α-synuclein overexpression, however, in the current study, only total α-synuclein positive aggregates in the striatum were assessed, and Ser129-phosphorylated α-synuclein-positive aggregates were not separately analyzed.

The present results showed that GM1 ganglioside, previously shown to be neuroprotective in MPTP models of PD, also has neuroprotective effects in an AAV-A53T α-synuclein overexpression model of PD. Neuroprotective effects in this model, which is presumed to be more pathologically relevant to PD than neurotoxin models, is in agreement with clinical results with GM1 in PD patients, where prolonged use of GM1 produced evidence of a potential disease modifying effect. Development of treatments that directly impact the underlying disease processes in PD and that can slow neuronal cell death and symptom progression remain an unmet need of the PD population. Based on previous work and the current results, GM1 continues to have potential to be such a treatment, with the potential to protect DA neurons form dying as well as rescue and restore function to damaged but viable neurons, and thus continued clinical development of GM1 for PD is indicated.

Example 7: GM1 Treatment Reduces Cellular Transfer of α-Syn

Figure 9:
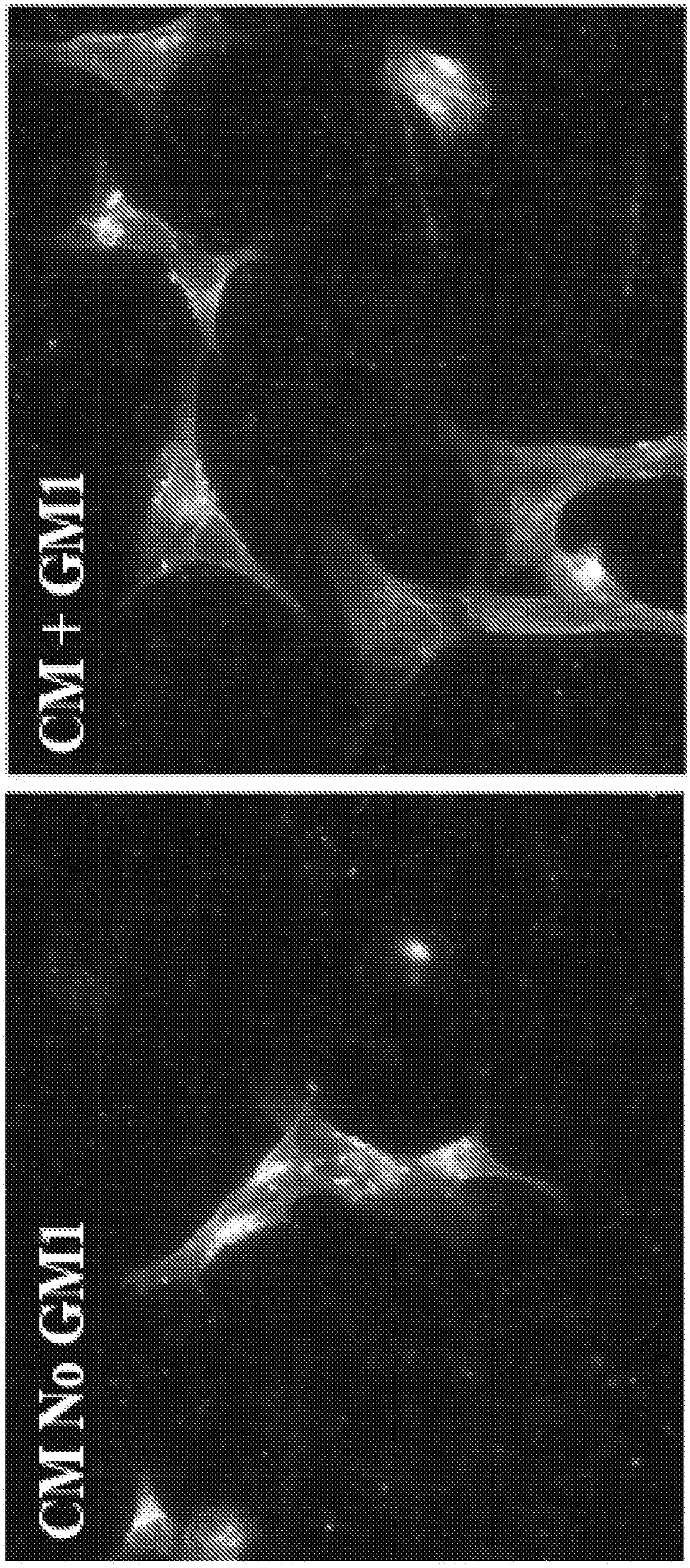
FIG. 9 illustrates reduced uptake of GFP-α-Syn in the presence of GM1. Conditioned media (CM) from MN9D cells stably expressing GFP tagged wild-type human «-Syn was applied to normal, differentiated SH-SY5Y cells for 24 hrs with and without GM1 ganglioside (100 μM) added to the media. GFP-α-Syn was taken up into control SH-SY5Y cells and there was reduced uptake of GFP-α-Syn in the presence of GM1.

It has recently become appreciated that cell-to-cell transfer of α-Syn may be an important factor in the progression of synucelinopathies. Cell-to-cell transfer of α-Syn can occur as free α-Syn or as α-Sy-containing exosomes. Herein, a preliminary study was conducted to assess the extent to which GM1 can influence α-Syn release and/or uptake by neighboring cells. MN9D dopaminergic cells stably expressing human WT α-Syn tagged with GFP were cultured to ~90% confluency and shifted to serum free media for 48 hours to generate conditioned medium (CM), which was collected, spun at 1000 rpm for 10 minutes and filtered through a sterile 40 μm filter. Normal SH-SY5Y cells (ATCC) were plated in 8 well chamber slides and differentiated in 10 μM retinoic acid for 7 days. Sterile CM or regular medium were used to replace 50% of the medium in each well. The cells were grown in the CM for 24 hours in presence or absence of 100 μM GM1, fixed in 4% paraformaldehyde for 10 minutes, and processed for enhanced visualization of GFP using GFP immunofluorescence. GFP-α-Syn was taken up into control SH-SY5Y cells, however, there were reduced levels of GFP-α-Syn in cells cultured in the presence of GM1 (FIG. 9). These results suggest that in the presence of GM1, there is decreased cellular uptake of released α-Syn released in exosomes and/or released free α-Syn.

Example 8: GM1 Influences α-Syn Phosphorylation and Aggregation In Vivo

Figure 10:
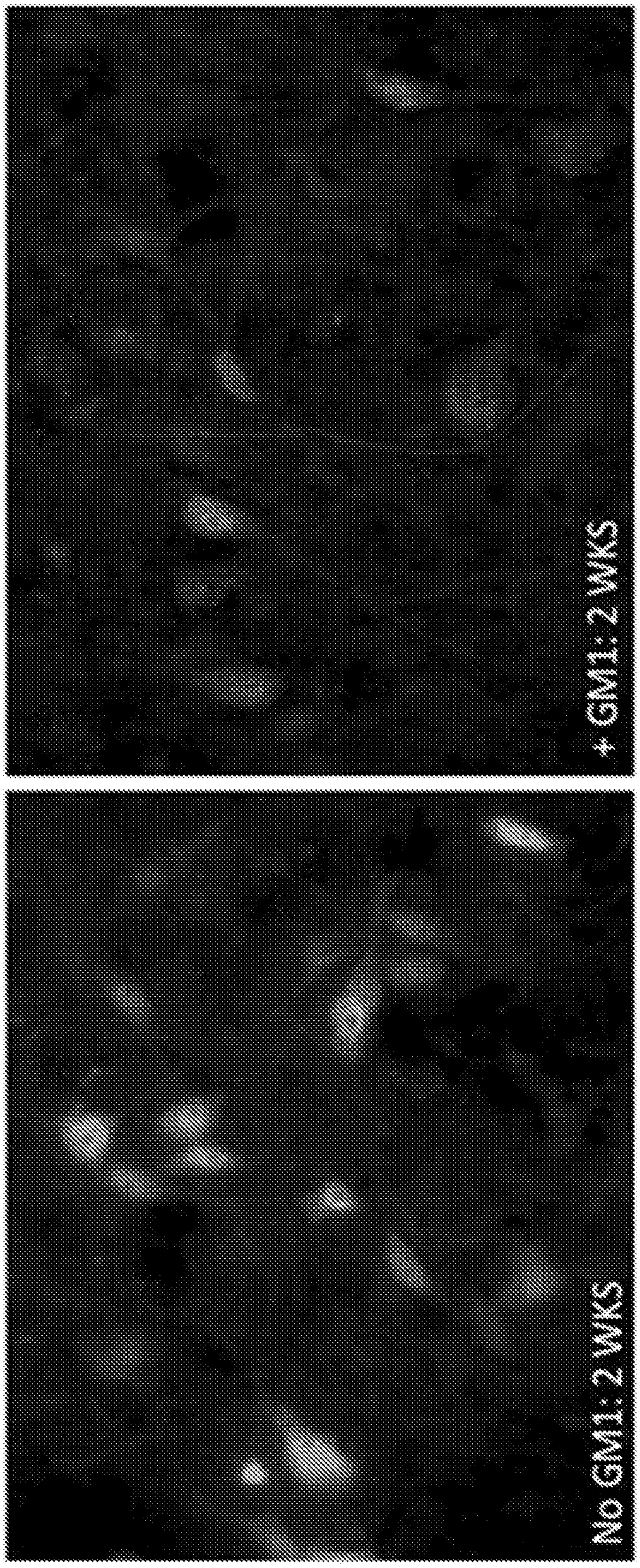
FIG. 10 illustrates the finding that at the early symptomatic stage (2 wks after AAV-A53T vector injection), insoluble pSer29 synuclein (following proteinase K digestion) is highly expressed in the SN in a saline-treated animal. In an animal that received GM1 (30 mg/kg/day) for 2 wks, starting 24 hrs after AAV-A53T injection, there were fewer SN neurons expressing insoluble pSer129 and decreased pSer129 expression per neuron, compared with saline-treated animals. As levels of insoluble pSer129 are taken as an indicator of synuclein aggregation, these data suggest decreased synuclein phosphorylation and aggregation in vivo in the presence of GM1.

Studies thus far do not suggest that GM1 administration decreases α-Syn mRNA or protein expression per se. However, GM1 administration may affect α-Syn phosphorylation and aggregation in vivo. Some studies have reported that in vitro, GM1 and α-Syn interact, resulting in an absence of fibril formation and an increase in helical folding propensity, resulting in GM1-mediated protection against aggregation. The extent to which this could occur in vivo has not been demonstrated prior to our studies. Data also suggest that Ser129 phosphorylation is related to the toxic accumulation of α-Syn and neurodegeneration in PD and other synucleinopathies and pSer129-positive aggregates are increased in rats overexpressing α-Syn. It was proposed herein that a mechanism that underlies the ability of GM1 to reduce α-Syn-related neurotoxicity is that GM1 administration reduces α-Syn phosphorylation and thus aggregation, and toxicity, in vivo. To demonstrate this, rats were prepared for unilateral administration of AAV1/2-A53T into the substantia nigra (SN) as described elsewhere herein. Beginning 24 hours after AAV administration, some animals received daily i.p. injections of saline and others received daily i.p. injections of GM1 (30 mg/kg). Animals were euthanized 2 weeks following initiation of saline or GM1 administration. Brains were subsequently sectioned and SN sections were treated with proteinase K and then processed for pSer129-Syn immunofluorescence. Results showed that there were significantly fewer pSer129 α-Syn-positive cells and less pSer129 α-Syn per cell in the SN of animals that received 2 weeks of GM1 administration, compared to saline-treated animals (FIG. 10).

Figure 11:
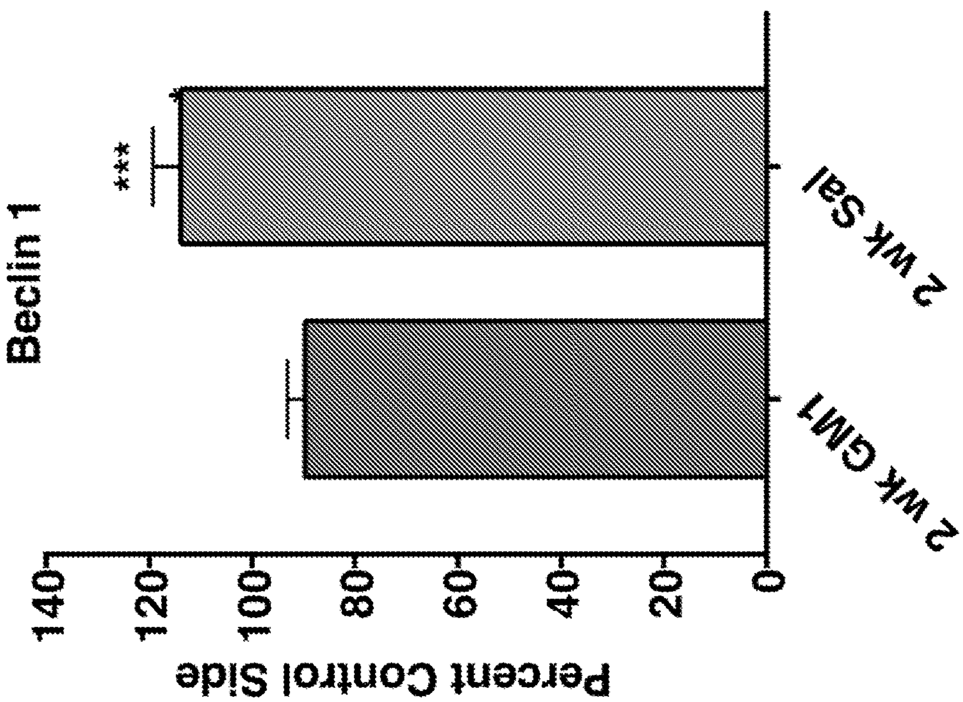
FIG. 11 illustrates the finding that at the early symptomatic stage (2 wks after vector injection), when synucleinopathy is developing but before substantial cell death has occurred, protein expression of Beclin-1 (***P=0.0004) was significantly increased in saline-treated vs. GM1-treated animals (N=8/grp).

Example 9 Assessing the Effects of GM1 on Lysosomal Function/Autophagic Processing In Vivo in the α-Synuclein Over-Expression Model In human PD, the presence of α-Syn-positive aggregates is associated with accumulation of autophagosomes and markers of lysosomal dysfunction, suggesting impaired lysosome-mediated clearance of α-Syn aggregates. The pathological phenotype of various storage disorders comprises increased α-Syn accumulation and aggregation and this increased α-Syn accumulation and aggregation has been linked to lysosomal dyfunction. Also, DA neuron degeneration induced by excess α-Syn in AAV-A53T rats is linked to a progressive decline in autophagic activity and in markers of lysosome function. It was observed that at 2 weeks following AAV-A53T administration to the SN, GM1 treatment reversed increased SN Beclin-1 levels, suggesting a possible early accumulation of autophagosomes and/or a problem with autophagosome clearance that is potentially reversed by GM1 (FIG. 11)

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiment or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of reducing the frequency or severity of at least one sign or symptom of a synucleinopathy in a mammalian subject in need thereof, wherein the synucleinopathy is selected from the group consisting of Lewy body dementia, multi-system atrophy, pure autonomic failure, inherited forms of Parkinson's disease with synuclein gene mutations, lysosomal storage disorders associated with abnormal alpha synuclein deposits in the brain, Sanfilippo syndrome and related Mucopolysaccaridoses, and GlcCerase (GBA) mutations accompanied by abnormal synuclein accumulation, the method comprising administering via intracranial stereotaxic injection an engineered adeno-associated virus (AAV) comprising a nucleic acid encoding sialidase Neu3 to the mammalian subject;
  - wherein expression of sialidase Neu3 is under the control of a neuron-specific promoter;
  - wherein the engineered AAV comprises a nucleotide sequence that is at least 85%, 90%, 91%, 92%, 93%, 94%, 95%, 96%, 97%, 98%, 99%, or 100% identical to a nucleotide sequence comprising nucleotides 1-3488 and 5309-8046 of SEQ ID NO: 2; and
  - wherein the method reduces the size of alpha-synuclein-positive aggregates in the striatum of the mammalian subject.

* * * * *